(12) United States Patent
Hitchcock et al.

(10) Patent No.: US 9,643,953 B2
(45) Date of Patent: May 9, 2017

(54) SUBSTITUTED BENZYLPYRAZOLES

(71) Applicants: Bayer Intellectual Property GmbH, Monheim (DE); BAYER PHARMA AKTIENGESELLSCHAFT, Berlin (DE)

(72) Inventors: Marion Hitchcock, Berlin (DE); Anne Mengel, Berlin (DE); Anja Richter, Berlin (DE); Hans Briem, Berlin (DE); Knut Eis, Berlin (DE); Vera Pütter, Berlin (DE); Gerhard Siemeister, Berlin (DE); Stefan Prechtl, Berlin (DE); Amaury Ernesto Fernández-Montalván, Berlin (DE); Christian Stegmann, Berlin (DE); Simon Holton, Berlin (DE); Mark Jean Gnoth, Mettmann (DE); Cornelia Preuβe, Berlin (DE)

(73) Assignees: BAYER INTELLECTUAL PROPERTY GMBH, Monheim (DE); BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/365,895

(22) PCT Filed: Dec. 17, 2012

(86) PCT No.: PCT/EP2012/075834
§ 371 (c)(1),
(2) Date: Jun. 16, 2014

(87) PCT Pub. No.: WO2013/092512
PCT Pub. Date: Jun. 27, 2013

(65) Prior Publication Data
US 2014/0315934 A1    Oct. 23, 2014

(30) Foreign Application Priority Data
Dec. 21, 2011 (EP) ...................................... 11194896

(51) Int. Cl.
*C07D 401/14* (2006.01)
*A61K 31/506* (2006.01)
*C07D 405/14* (2006.01)

(52) U.S. Cl.
CPC .......... *C07D 401/14* (2013.01); *A61K 31/506* (2013.01); *C07D 405/14* (2013.01)

(58) Field of Classification Search
CPC ... C07D 401/14; C07D 405/14; A61K 31/506
USPC .......... 544/298, 328; 514/256, 269
See application file for complete search history.

(56) References Cited

U.S. PATENT DOCUMENTS 5,470,862 A * 11/1995 Lin et al. ........ 514/341
2012/0184516 A1* 7/2012 Kim et al. .......... 514/171

FOREIGN PATENT DOCUMENTS

| WO | 03/051833 A2 | 6/2003 |
|---|---|---|
| WO | 03/082274 A1 | 10/2003 |
| WO | 2011/049988 A2 | 4/2011 |
| WO | 2011/115804 A1 | 9/2011 |
| WO | 2011/126903 A2 | 10/2011 |
| WO | 2012/003405 A1 | 1/2012 |
| WO | 2013/050438 A1 | 4/2013 |
| WO | 2013/101830 A1 | 7/2013 |
| WO | 2013/167698 A1 | 11/2013 |
| WO | 2014/047111 A1 | 3/2014 |
| WO | 2014/047325 A1 | 3/2014 |
| WO | 2014/047662 A2 | 3/2014 |
| WO | 2014/147144 A1 | 9/2014 |
| WO | 2014/147203 A1 | 9/2014 |
| WO | 2014/147204 A1 | 9/2014 |
| WO | 2014/202584 A1 | 12/2014 |
| WO | 2014/202586 A1 | 12/2014 |
| WO | 2014/202588 A1 | 12/2014 |
| WO | 2014/202590 A1 | 12/2014 |
| WO | 2014202583 A1 | 12/2014 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Krenn et al., Structural analysis reveals features of the spindle checkpoint kinase Bub1-kinetochore subunit Knl1 interaction, J Cell Biol. vol. 196, No. 4, pp. 451-467, Feb. 2012.*
Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*

(Continued)

*Primary Examiner* — Deepak Rao
(74) *Attorney, Agent, or Firm* — Morrison & Foerster LLP

(57) ABSTRACT

Compounds of formula (I) and their use as pharmaceutical.

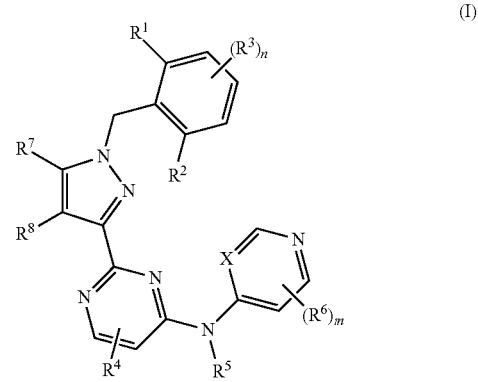

10 Claims, No Drawings

(56) References Cited

OTHER PUBLICATIONS

Johnson et al., Relationships between drug activity in NCI preclinical in vitro and in vivo models and early clinical trials, British Journal of Cancer (2001) 64(10): 1424-1431.*

Kops et al., On the road to cancer: Aneuploidy and the mitotic checkpoint, Nature Reviews Cancer, vol. 5, No. 10, pp. 773-785 (2005).*

Bolanos-Garcia et al., "BUB1 and BUBR1: multifaceted kinases of the cell cycle," Trends in Biochem. Sciences, Mar. 2011, 36(3):141-150.

Elowe, S., "Bub1 and BubR1: at the Interface between Chromosome Attachment and the Spindle Checkpoint," Molecular and Cellular Biology, Aug. 2011, 31(15):3085-3093.

Hanahan et al., "Hallmarks of Cancer: The Next Generation," Cell, Mar. 4, 2011, 144:646-674.

Hanahan et al., "The Hallmarks of Cancer," Cell, Jan. 7, 2000, 100:57-70.

Kawashima et al., "Phosphorylation of H2A by Bub1 Prevents Chromosomal Instability Through Localizing Shugoshin," Science, Jan. 8, 2010, 327:172-177.

King, R. W., "When 2+2=5: The origins and fates of aneuploid and tetraploid cells," Biochimica et Biophys. Acta 1786, 2008:4-14.

Kops et al., "On the Road to Cancer: Aneuploidy and the Mitotic Checkpoint," Nature Reviews/Cancer, Oct. 2005, 5:773-785.

Musacchio et al., "The spindle-assembly checkpoint in space and time," Nature Reviews/Molecular Cell Biology, May 2007, 8:379-393.

Rieder et al., "Stuck in Division or Passing through: Review What Happens When Cells Cannot Satisfy the Spindle Assembly Checkpoint," Developmental Cell, Nov. 2004, 7:637-651.

Roberts et al., "The Saccharomyces cerevisiae Checkpoint Gene BUB1 Encodes a Novel Protein Kinase," Molecular and Cellular Biology, Dec. 1994, 14:(12)8282-8291.

Schmidt et al., "Exploiting the Compromised Spindle Assembly Checkpoint Function of Tumor Cells" Cell Cycle, Jan. 16, 2006, 5(2):159-163.

Schmidt et al., "Mitotic drug targets and the development of novel anti-mitotic anticancer drugs," Drug Resistance Updates, 2007, 10:162-181.

Suijkerbuijk et al., "Preventing aneuploidy: The contribution of mitotic checkpoint proteins," Biochmica et Biophysica Acta 1786, 2008, 24-31.

Watanabe, Y., "Temporal and Spatial Regulation of Targeting Aurora B to the Inner Centromere," Cold Springs Harbor Symp. on Quantitative Biol., 75, 2010 Pub. Cold Spg. Harbor Lab. Press, 419-423.

Weaver et al., "Aneuploidy: Instigator and Inhibitor of Tumorigenesis," Cancer Res., Nov. 1, 2007, 67 (21):10103-10105.

Yuan et al., "Increased Expression ofMitotic Checkpoint Genes in Breast Cancer Cellswith Chromosomal Instability," Clin. Cancer Res., Jan. 15, 2006, 12(2):405-410.

Related co-pending U.S. Appl. No. 14/350,160, filed Apr. 7, 2014 (allowed).
Related co-pending U.S. Appl. No. 14/400,315, filed Nov. 10, 2014 (allowed).
Related co-pending U.S. Appl. No. 14/778,604, filed Sep. 20, 2015.
Related co-pending U.S. Appl. No. 14/899,469, filed Dec. 21, 2015.
Related co-pending U.S. Appl. No. 14/778,975, filed Sep. 21, 2015.
Related co-pending U.S. Appl. No. 14/778,733, filed Sep. 21, 2015.
Related co-pending U.S. Appl. No. 14/900,599, filed Dec. 21, 2015.
Related co-pending U.S. Appl. No. 14/899,418, filed Dec. 17, 2015.
Related co-pending U.S. Appl. No. 14/900,548, filed Dec. 21, 2015.
Related co-pending U.S. Appl. No. 14/900,575, filed Dec. 21, 2015.
Related co-pending U.S. Appl. No. 15/032,957, filed Apr. 28, 2016.

* cited by examiner

SUBSTITUTED BENZYLPYRAZOLES

FIELD OF APPLICATION OF THE INVENTION

The invention relates to substituted benzylpyrazole compounds, a process for their production and the use thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast *S. cerevisiae* with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which, have been reviewed by Elowe [Elowe S, Mol. Cell. Biol. 31, 3085, 2011. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as vinca alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004]. In contrast, inhibitors of Bub1 prevent the establishment and/or functionality of the mitotic checkpoint, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options.

In the field of bub1 kinase inhibitors no state of the art is published so far. However in the field of sGC stimulators which is entirely unrelated to the field of oncology exists prior art, e.g. WO1012/003405, disclosing structurally related compounds for a completely different purpose relying on the effect of prevention, management and treatment of disorders such as pulmonary hypertension, arterial hypertension, heart failure, atherosclerosis, inflammation, thrombosis, renal fibrosis and failure, liver cirrhosis, erectile dysfunction and other cardiovascular disorders.

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I)

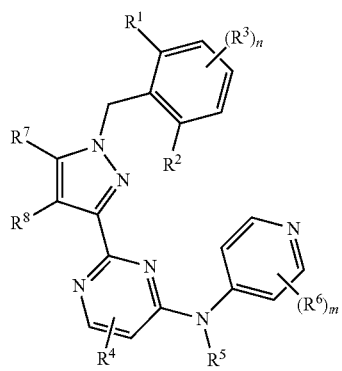

in which
$R^1/R^2$ are independently from each other hydrogen, halogen or phenyl-S—,
$R^3$ is independently from each other hydrogen, 1-6C-alkoxy, halogen, 2-6C-alkenyl, 3-6C-cycloalkyl, 1-6C-haloalkoxy or C(O)OH,
n is 1-3,
$R^4$ is
  (a) hydrogen,
  (b) hydroxy,
  (c) 1-6C-alkoxy opt. subst. with
    (c1) 1-2 OH,
    (c2) $NR^9R^{10}$,
    (c3) 1-4C-alkyl-S—,
    (c4) 1-4C-alkyl-S(O)—,
    (c5) 1-4C-alkyl-S(O)$_2$—,
    (c6) —S(O)$_2NR^9R^{10}$,
  (d)

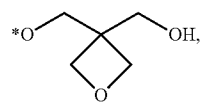

whereby the * is the point of attachment,
  (e)

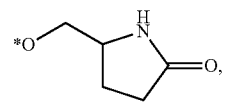

whereby the * is the point of attachment,
  (f) cyano,
  (g) 1-4C-alkyl-S(O)$_2$—,
$R^5$ is
  (a) hydrogen,
  (b) 2-6C-hydroxyalkyl,
  (c)

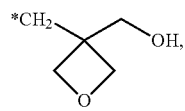

whereby the * is the point of attachment,
  (d) —C(O)-(1-6C-alkyl),
  (e) —C(O)-(1-6C-alkylen)-O-(1-6C-alkyl),
  (f) —C(O)-(1-6C-alkylen)-O-(1-6C-alkylen)-O-(1-6C-alkyl),
$R^6$ is hydrogen, halogen, cyano, $C(O)NR^{11}R^{12}$, $C(O)OR^{13}$ or C(O)NHOH,
$R^7$ is hydrogen, 1-6C-alkyl, 2-6C-alkenyl, 1-6C-alkoxy, 3-6C-cycloalkyl, or $NR^9R^{10}$,
$R^8$ is hydrogen or 1-6C-alkyl,
m is 1-4,
$R^9$, $R^{10}$ are independently from each other hydrogen or 1-6C-alkyl,
$R^{11}$, $R^{12}$ are independently from each other hydrogen, 1-6C-alkyl, 2-6C-hydroxyalkyl or (1-4C-alkyl)-SO$_2$-(1-4C-alkyl),
$R^{13}$ is hydrogen or 1-4C-alkyl,
or an N-oxide, a salt, a tautomer or a stereoisomer of said compound, or a salt of said N-oxide, tautomer or stereoisomer.

In accordance with a second aspect, the invention relates to compounds of formula (I)
in which
$R^1/R^2$ are independently from each other hydrogen, halogen,
$R^3$ is independently from each other hydrogen, 1-6C-alkoxy, halogen, 2-6C-alkenyl, 3-6C-cycloalkyl, 1-6C-haloalkoxy
n 1-3,
$R^4$ is
(a) hydrogen; (b) hydroxy; (c) 1-4C-alkoxy (opt. subst. with (c1) 1-2 OH, (c2) $NR^9R^{10}$), (d)

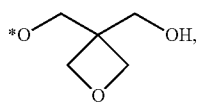

whereby the * is the point of attachment,
R⁵ is (a) hydrogen, (b) 2-6C-hydroxyalkyl, (c)

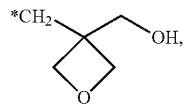

whereby the * is the point of attachment,
(d) —C(O)-(1-6C-alkyl)
(e) —C(O)-(1-6C-alkylen)-O-(1-6C-alkyl)
(f) —C(O)-(1-46C-alkylen)-O-(1-6C-alkylen)-O-(1-6C-alkyl)
$R^6$ is hydrogen, halogen, cyano, $C(O)NR^{11}R^{12}$,
$R^7$ is hydrogen, 1-6C-alkyl, 2-6C-alkenyl, 1-6C-alkoxy, 3-6C-cycloalkyl, $NR^9R^{10}$,
$R^8$ is hydrogen, 1-6C-alkyl,
m is 1-4
$R^9$, $R^{10}$ are independently from each other hydrogen, 1-6C-alkyl,
$R^{11}$, $R^{12}$ are independently from each other hydrogen, 1-6C-alkyl,
or an N-oxide, a salt, a tautomer or a stereoisomer of said compound, or a salt of said N-oxide, tautomer or stereoisomer.

A further aspect of the invention are compounds of formula (I) according to claim 1,
wherein
$R^1/R^2$ are independently from each other hydrogen, halogen or phenyl-S—,
$R^3$ is independently hydrogen, halogen, 1-4C-alkoxy, 3-6C-cycloalkyl, 1-4C-haloalkoxy or C(O)OH,
n is 1-3,
$R^4$ is
(a) hydrogen,
(b) hydroxy,
(c) 1-4C-alkoxy opt. subst. with
    (c1) 1-2 OH,
    (c2) $NR^9R^{10}$,
    (c3) 1-4C-alkyl-S—,
    (c4) 1-4C-alkyl-S(O)—,
    (c5) 1-4C-alkyl-S(O)₂—,
    (c6) $S(O)_2NR^9R^{10}$,
(d)

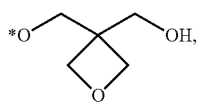

whereby the * is the point of attachment,
(e)

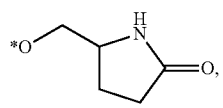

whereby the * is the point of attachment,
(f) cyano,
(g) 1-4C-alkyl-S(O)₂—,
$R^5$ is hydrogen,
$R^6$ is hydrogen, cyano, $C(O)NR^{11}R^{12}$, $C(O)OR^{13}$ or C(O)NHOH,
$R^7$ is 2-4C-alkenyl, 1-4C-alkoxy, 3-6C-cycloalkyl or $NR^9R^{10}$,
$R^8$ is hydrogen or 1-4C-alkyl,
m is 1-4,
$R^9$, $R^{10}$ are independently from each other hydrogen or 1-4C-alkyl,
$R^{11}$, $R^{12}$ are independently from each other hydrogen, 1-4C-alkyl, 2-6C-hydroxyalkyl or (1-4C-alkyl)-SO₂-(1-4C-alkyl),
$R^{13}$ is hydrogen or 1-4C-alkyl,
or an N-oxide, a salt, a tautomer or a stereoisomer of said compound, or a salt of said N-oxide, tautomer or stereoisomer.

Another aspect of the invention are compounds of formula (I) according to claim 1,
wherein
$R^1/R^2$ are independently from each other hydrogen, halogen or phenyl-S—,
$R^3$ is independently hydrogen, halogen, 1-4C-alkoxy, 3-6C-cycloalkyl, 1-4C-haloalkoxy or C(O)OH,
n is 1-3,
$R^4$ is
(a) hydrogen;
(b) hydroxy;
(c) 1-4C-alkoxy opt. subst. with
    (c1) OH,
    (c2) $NR^9R^{10}$,
    (c3) 1-4C-alkyl-S—,
    (c4) 1-4C-alkyl-S(O)—,
    (c5) 1-4C-alkyl-S(O)₂—,
    (c6) $S(O)_2NR^9R^{10}$,
(d)

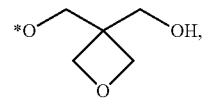

whereby the * is the point of attachment,
(e)

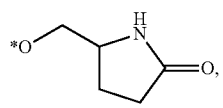

whereby the * is the point of attachment,
(f) cyano,
(g) 1-4C-alkyl-S(O)₂—,
$R^5$ is hydrogen,
$R^6$ is hydrogen, cyano, $C(O)NR^{11}R^{12}$, $C(O)OR^{13}$ or C(O)NHOH,
$R^7$ is 2-4C-alkenyl, 1-4C-alkoxy, 3-6C-cycloalkyl or $NR^9R^{10}$,
$R^8$ is hydrogen or 1-4C-alkyl,
m is 1
$R^9$, $R^{10}$ are independently from each other hydrogen or 1-4C-alkyl,
$R^{11}$, $R^{12}$ are independently from each other 1-4C-alkyl, 2-4C-hydroxyalkyl or (1-4C-alkyl)-SO₂-(1-4C-alkyl),
$R^{13}$ is hydrogen or 1-4C-alkyl,
or an N-oxide, a salt, a tautomer or a stereoisomer of said compound, or a salt of said N-oxide, tautomer or stereoisomer.

A further aspect of the invention relates to compounds of formula (I)

$R^1/R^2$ are independently from each other hydrogen, halogen or phenyl-S—, $R^3$ is independently from each other hydrogen, 1-4C-alkoxy, halogen, 2-4C-alkenyl, 3-6C-cycloalkyl, 1-4C-haloalkoxy or C(O)OH, n is 1-3, $R^4$ is
(a) hydrogen,
(b) hydroxy,
(c) 1-4C-alkoxy opt. subst. with
  (c1) 1-2 OH,
  (c2) $NR^9R^{10}$,
  (c3) 1-4C-alkyl-S—,
  (c4) 1-4C-alkyl-S(O)—,
  (c5) 1-4C-alkyl-S(O)$_2$—,
  (c6) —S(O)$_2NR^9R^{10}$,
(d)

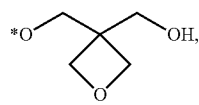

whereby the * is the point of attachment,
(e)

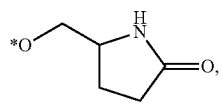

whereby the * is the point of attachment,
(f) cyano,
(g) 1-4C-alkyl-S(O)$_2$—, $R^5$ is
(a) hydrogen,
(b) 2-4C-hydroxyalkyl,
(c)

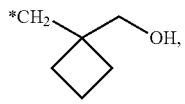

whereby the * is the point of attachment,
(d) —C(O)-(1-4C-alkyl),
(e) —C(O)-(1-4C-alkylen)-O-(1-4C-alkyl),
(f) —C(O)-(1-4C-alkylen)-O-(1-4C-alkylen)-O-(1-4C-alkyl), $R^6$ is hydrogen, halogen, cyano, $C(O)NR^{11}R^{12}$, $C(O)OR^{13}$ or C(O)NHOH, $R^7$ is hydrogen, 1-4C-alkyl, 2-4C-alkenyl, 1-4C-alkoxy, 3-4C-cycloalkyl, or $NR^9R^{10}$, $R^8$ is hydrogen or 1-4C-alkyl, m is 1-4, $R^9$, $R^{10}$ are independently from each other hydrogen or 1-4C-alkyl, $R^{11}$, $R^{12}$ are independently from each other hydrogen, 1-4C-alkyl, 2-4C-hydroxyalkyl or (1-4C-alkyl)-SO$_2$-(1-4C-alkyl), $R^{13}$ is hydrogen or 1-4C-alkyl, or an N-oxide, a salt, a tautomer or a stereoisomer of said compound, or a salt of said N-oxide, tautomer or stereoisomer.

A further aspect of the invention relates to compounds of formula (I)
wherein $R^1/R^2$ are independently from each other hydrogen, halogen, $R^3$ is independently from each other hydrogen, 1-4C-alkoxy, halogen, 2-4C-alkenyl, 3-6C-cycloalkyl, haloalkoxy n 1-3, $R^4$ is
(a) hydrogen; (b) hydroxy; (c) 1-4C-alkoxy (opt. subst. with (c1) 1-2 OH, (c2) $NR^9R^{10}$, (d)

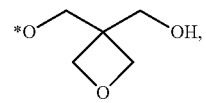

whereby the * is the point of attachment, $R^5$ is (a) hydrogen, (b) 2-4C-hydroxyalkyl, (c)

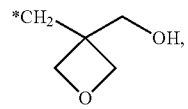

whereby the * is the point of attachment,
(d) —C(O)-(1-4C-alkyl)
(e) —C(O)-(1-4C-alkylen)-O-(1-4C-alkyl)
(f) —C(O)-(1-4C-alkylen)-O-(1-4C-alkylen)-O-(1-4C-alkyl)

$R^6$ is hydrogen, halogen, cyano, $C(O)NR^{11}R^{12}$, $R^7$ is hydrogen, 1-4C-alkyl, 2-4C-alkenyl, 1-4C-alkoxy, 3-6C-cycloalkyl, $NR^9R^{10}$, $R^8$ is hydrogen, 1-4C-alkyl, m is 1-4

$R^9$, $R^{10}$ are independently from each other hydrogen, 1-4C-alkyl, $R^{11}$, $R^{12}$ are independently from each other hydrogen, 1-4C-alkyl, or an N-oxide, a salt, a tautomer or a stereoisomer of said compound, or a salt of said N-oxide, tautomer or stereoisomer.

A further aspect of the invention relates to compounds of formula (I)
wherein $R^1/R^2$ are independently from each other hydrogen, halogen $R^3$ is independently hydrogen, 1-4C-alkoxy, n 1-3, $R^4$ is (b) hydroxy; (c) 1-4C-alkoxy opt. subst. with (c1) 1-2 OH, (c2) $NR^9R^{10}$, (d)

whereby the * is the point of attachment, $R^5$ is hydrogen, $R^6$ is hydrogen, cyano, $C(O)NR^{11}R^{12}$, $R^7$ is 2-4C-alkenyl, 1-4C-alkoxy, 3-6C-cycloalkyl, $NR^9R^{10}$, $R^8$ is hydrogen, 1-4C-alkyl, m is 1-4

$R^9$, $R^{10}$ are independently from each other hydrogen, 1-4C-alkyl, $R^{11}$, $R^{12}$ are hydrogen, or an N-oxide, a salt, a tautomer or a stereoisomer of said compound, or a salt of said N-oxide, tautomer or stereoisomer.

Another aspect of the invention relates to compounds of formula (I)
wherein
$R^1/R^2$ are independently from each other hydrogen, halogen,
$R^3$ is independently hydrogen, 1-4C-alkoxy,
n is 1,
$R^4$ is (b) hydroxy; (c) 1-4C-alkoxy (opt. subst. with (c1) OH, (c2) $NR^9R^{10}$,) (d)

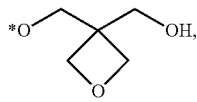

whereby the * is the point of attachment,
$R^5$ is hydrogen,
$R^6$ is hydrogen, cyano, $C(O)NR^{11}R^{12}$,
$R^7$ is 2-4C-alkenyl, 1-4C-alkoxy, 3-6C-cycloalkyl, $NR^9R^{10}$,
$R^8$ is hydrogen, 1-4C-alkyl,
m is 1
$R^9, R^{10}$ are independently from each other hydrogen, 1-4C-alkyl,
$R^{11}, R^{12}$ are hydrogen,
or an N-oxide, a salt, a tautomer or a stereoisomer of said compound, or a salt of said N-oxide, tautomer or stereoisomer.

A further aspect of the invention are compounds of formula (I) according to claim 1,
wherein,
$R^1/R^2$ are independently from each other hydrogen, fluorine, chlorine or phenyl-S—,
$R^3$ is hydrogen, fluorine, methoxy, ethoxy, cyclopropyl, difluoromethoxy, 2,2,2-trifluoroethoxy or C(O)OH,
n is 1-3,
$R^4$ is
(a) hydrogen,
(b) hydroxy,
(c) methoxy which is optionally substituted with —S(O)$_2NH_2$,
(d) ethoxy which is optionally substituted with hydroxy or —N(CH$_3$)$_2$, —SCH$_3$, —S(O)CH$_3$ or —S(O)$_2$CH$_3$,
(e) propoxy which is substituted with —SCH$_3$, —S(O)CH$_3$ or —S(O)$_2$CH$_3$,
(f)

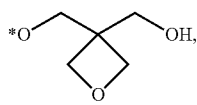

whereby the * is the point of attachment,
(g)

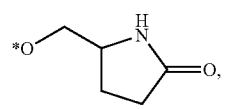

whereby the * is the point of attachment,
(h) cyano,
(i) —S(O)$_2$CH$_3$,
(k) —S(O)$_2$CH(CH$_3$)$_2$,
$R^5$ is hydrogen,
$R^6$ is hydrogen, cyano, C(O)NH$_2$, $C(O)NR^{11}R^{12}$, $C(O)OR^{13}$ or C(O)NHOH,
$R^7$ is vinyl, methoxy, ethoxy, cyclopropyl or —N(CH$_3$)$_2$, $R^8$ is hydrogen, methyl or ethyl,
m is 1,
$R^9, R^{10}$ are hydrogen or methyl,
$R^{11}$ is hydrogen,
$R^{12}$ is methyl, —CH$_2$—CH$_2$—OH, —CH$_2$—CH$_2$—SO$_2$—CH$_3$,
$R^{13}$ is hydrogen or ethyl,
or an N-oxide, a salt, a tautomer or a stereoisomer of said compound, or a salt of said N-oxide, tautomer or stereoisomer.

Another aspect of the invention relates to compounds of formula (I)
wherein,
$R^1/R^2$ are independently from each other hydrogen, fluorine or chlorine,
$R^3$ is hydrogen, methoxy or ethoxy,
n is 1,
$R^4$ is (a) hydroxy, (b) methoxy, or (c) ethoxy (which is optionally substituted with hydroxy or —N(CH$_3$)$_2$), (d)

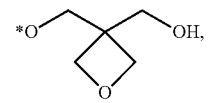

whereby the * is the point of attachment,
$R^5$ is hydrogen,
$R^6$ is hydrogen, cyano, C(O)NH$_2$,
$R^7$ is vinyl,
methoxy, ethoxy, cyclopropyl,
$R^8$ is hydrogen, methyl,
m is 1
$R^9, R^{10}$ are methyl,
or an N-oxide, a salt, a tautomer or a stereoisomer of said compound, or a salt of said N-oxide, tautomer or stereoisomer.

In a further aspect of the invention relates to compounds of formula (I), wherein
$R^1/R^2$ are independently from each other hydrogen, halogen or phenyl-S—,
$R^3$ is independently from each other hydrogen, 1-6C-alkoxy, halogen, 2-6C-alkenyl, 3-6C-cycloalkyl, 1-6C-haloalkoxy or C(O)OH,
n is 1-3,
$R^4$ is
(c) 1-6C-alkoxy opt. subst. with
(c3) 1-4C-alkyl-S—,
(c4) 1-4C-alkyl-S(O)—,
(c5) 1-4C-alkyl-S(O)$_2$—,
(c6) S(O)$_2NR^9R^{10}$,
(e)

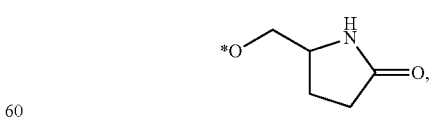

whereby the * is the point of attachment,
(f) cyano,
(g) 1-4C-alkyl-S(O)$_2$—,
$R^5$ is
(a) hydrogen,
(b) 2-6C-hydroxyalkyl, (c)

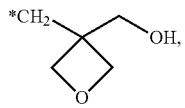

whereby the * is the point of attachment,
(d) —C(O)-(1-6C-alkyl),
(e) —C(O)-(1-6C-alkylen)-O-(1-6C-alkyl),
(f) —C(O)-(1-6C-alkylen)-O-(1-6C-alkylen)-O-(1-6C-alkyl), $R^8$ is hydrogen, halogen, cyano, C(O)$NR^{11}R^{12}$, C(O)$OR^{13}$ or C(O)NHOH,
$R^7$ is hydrogen, 1-6C-alkyl, 2-6C-alkenyl, 1-6C-alkoxy, 3-6C-cycloalkyl, or $NR^9R^{10}$,
$R^8$ is hydrogen or 1-6C-alkyl,
m is 1-4,
$R^9$, $R^{10}$ are independently from each other hydrogen or 1-6C-alkyl,
$R^{11}$, $R^{12}$ are independently from each other hydrogen, 1-6C-alkyl, 2-6C-hydroxyalkyl or 2-(methylsulfonyl)ethyl,
$R^{13}$ is hydrogen or 1-4C-alkyl,
or an N-oxide, a salt, a tautomer or a stereoisomer of said compound, or a salt of said N-oxide, tautomer or stereoisomer.

In still another aspect of the invention relates to compounds of formula (I),
wherein
$R^1/R^2$ are independently from each other hydrogen, halogen or phenyl-S—,
$R^3$ is independently from each other hydrogen, 1-6C-alkoxy, halogen, 2-6C-alkenyl, 3-6C-cycloalkyl, 1-6C-haloalkoxy or C(O)OH,
n is 1-3,
$R^4$ is (a) hydrogen,
(c) 1-6C-alkoxy opt. subst. with
(c1) 1-2 OH,
(c2) $NR^9R^{10}$,
(c3) 1-4C-alkyl-S—,
(c4) 1-4C-alkyl-S(O)—,
(c5) 1-4C-alkyl-S(O)$_2$—,
(c6) S(O)$_2NR^9R^{10}$,
(d)

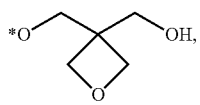

whereby the * is the point of attachment,
(e)

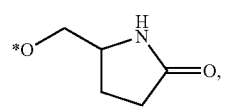

whereby the * is the point of attachment,
$R^5$ is
(a) hydrogen,
(b) 2-6C-hydroxyalkyl, (c)

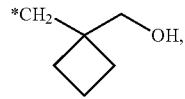

whereby the * is the point of attachment,
(d) —C(O)-(1-6C-alkyl),
(e) —C(O)-(1-6C-alkylen)-O-(1-6C-alkyl),
(f) —C(O)-(1-6C-alkylen)-O-(1-6C-alkylen)-O-(1-6C-alkyl), $R^6$ is hydrogen, halogen, cyano, C(O)$NR^{11}R^{12}$, C(O)$OR^{13}$ or C(O)NHOH,
$R^7$ is hydrogen, 1-6C-alkyl, 2-6C-alkenyl, 1-6C-alkoxy, 3-6C-cycloalkyl, or $NR^9R^{10}$,
$R^8$ is hydrogen or 1-6C-alkyl,
m is 1-4,
$R^9$, $R^{10}$ are independently from each other hydrogen or 1-6C-alkyl,
$R^{11}$, $R^{12}$ are independently from each other hydrogen, 1-6C-alkyl, 2-6C-hydroxyalkyl or 2-(methylsulfonyl)ethyl,
$R^{13}$ is hydrogen or 1-4C-alkyl,
or an N-oxide, a salt, a tautomer or a stereoisomer of said compound, or a salt of said N-oxide, tautomer or stereoisomer.

In a further aspect of the invention relates to compounds of formula (I), wherein
$R^1/R^2$ are independently from each other hydrogen, halogen or phenyl-S—,
$R^3$ is independently from each other hydrogen, 1-6C-alkoxy, halogen, 2-6C-alkenyl, 3-6C-cycloalkyl, 1-6C-haloalkoxy or C(O)OH,
n is 1-3,
$R^4$ is
(a) hydrogen,
(b) hydroxy,
(c) 1-6C-alkoxy opt. subst. with
(c1) 1-2 OH,
(c2) $NR^9R^{10}$,
(c3) 1-4C-alkyl-S—,
(c4) 1-4C-alkyl-S(O)—,
(c5) 1-4C-alkyl-S(O)$_2$—,
(c6) S(O)$_2NR^9R^{10}$,
(d)

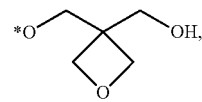

whereby the * is the point of attachment,
(e)

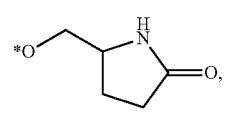

whereby the * is the point of attachment,
(f) cyano,
(g) 1-4C-alkyl-S(O)$_2$—, $R^5$ is
(c)

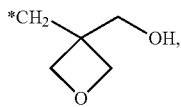

whereby the * is the point of attachment,
(e) —C(O)-(1-6C-alkylen)-O-(1-6C-alkyl),
(f) —C(O)-(1-6C-alkylen)-O-(1-6C-alkylen)-O-(1-6C-alkyl), $R^6$ is hydrogen, halogen, cyano, C(O)NR$^{11}$R$^{12}$, C(O)OR$^{13}$ or C(O)NHOH, $R^7$ is hydrogen, 1-6C-alkyl, 2-6C-alkenyl, 1-6C-alkoxy, 3-6C-cycloalkyl, or NR$^9$R$^{10}$, $R^8$ is hydrogen or 1-6C-alkyl, m is 1-4, $R^9$, $R^{10}$ are independently from each other hydrogen or 1-6C-alkyl, $R^{11}$, $R^{12}$ are independently from each other hydrogen, 1-6C-alkyl, 2-6C-hydroxyalkyl or 2-(methylsulfonyl)ethyl, $R^{13}$ is hydrogen or 1-4C-alkyl, or an N-oxide, a salt, a tautomer or a stereoisomer of said compound, or a salt of said N-oxide, tautomer or stereoisomer.

Another aspect of the invention relates to compounds of formula (I) according to claim 1,
wherein $R^1/R^2$ are independently from each other hydrogen, halogen or phenyl-S—, $R^3$ is independently from each other hydrogen, 1-6C-alkoxy, halogen, 2-6C-alkenyl, 3-6C-cycloalkyl, 1-6C-haloalkoxy or C(O)OH, n is 1-3, $R^4$ is
(a) hydrogen,
(c) 1-6C-alkoxy opt. subst. with
(c1) 1-2 OH,
(c2) NR$^9$R$^{10}$,
(c3) 1-4C-alkyl-S—,
(c4) 1-4C-alkyl-S(O)—,
(c5) 1-4C-alkyl-S(O)$_2$—,
(c6) —S(O)$_2$NR$^9$R$^{10}$,
(d)

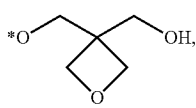

whereby the * is the point of attachment,
(e)

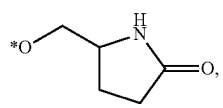

whereby the * is the point of attachment,
$R^5$ is
(c)

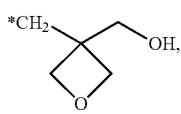

whereby the * is the point of attachment,
(e) —C(O)-(1-6C-alkylen)-O-(1-6C-alkyl),
(f) —C(O)-(1-6C-alkylen)-O-(1-6C-alkylen)-O-(1-6C-alkyl), $R^6$ is hydrogen, —C(O)NH-(1-3C-alkyl)-OH, —C(O)NH-(1-3Calkyl)-SO$_2$-(1-3C-alkyl), or C(O)NHOH, $R^7$ is hydrogen, 1-6C-alkyl, 2-6C-alkenyl, 1-6C-alkoxy, 3-6C-cycloalkyl, or NR$^9$R$^{10}$, $R^8$ is hydrogen or 1-6C-alkyl, m is 1-4, $R^9$, $R^{10}$ are independently from each other hydrogen or 1-6C-alkyl, $R^{13}$ is hydrogen or 1-4C-alkyl, or an N-oxide, a salt, a tautomer or a stereoisomer of said compound, or a salt of said N-oxide, tautomer or stereoisomer.

In a further aspect of the invention relates to compounds of formula (I) selected from the group consisting of:

2-[1-(4-ethoxy-2,6-difluorobenzyl)-5-methoxy-4-methyl-1H-pyrazol-3-yl]-5-methoxy-N-(pyridin-4-yl)pyrimidin-4-amine, 2-[5-(dimethylamino)-1-(2-fluorobenzyl)-1H-pyrazol-3-yl]-5-methoxy-N-(pyridin-4-yl)pyrimidin-4-amine, 2-[1-(2-fluorobenzyl)-5-methoxy-1H-pyrazol-3-yl]-5-methoxy-N-(pyridin-4-yl)pyrimidin-4-amine, 2-[5-ethoxy-1-(2-fluorobenzyl)-1H-pyrazol-3-yl]-5-methoxy-N-(pyridin-4-yl)pyrimidin-4-amine, 2-(1-benzyl-5-cyclopropyl-1H-pyrazol-3-yl)-5-methoxy-N-(pyridin-4-yl)pyrimidin-4-amine, 2-(1-benzyl-5-ethenyl-1H-pyrazol-3-yl)-5-methoxy-N-(pyridin-4-yl)pyrimidin-4-amine, 4-({2-[1-(2-fluorobenzyl)-5-methoxy-1H-pyrazol-3-yl]-5-methoxypyrimidin-4-yl}amino)pyridine-3-carbonitrile, 2-[5-cyclopropyl-1-(4-methoxybenzyl)-1H-pyrazol-3-yl]-5-methoxy-N-(pyridin-4-yl)pyrimidin-4-amine, 2-[5-cyclopropyl-1-(2,6-dichlorobenzyl)-4-methyl-1H-pyrazol-3-yl]-5-methoxy-N-(pyridin-4-yl)pyrimidin-4-amine, 2-[5-cyclopropyl-1-(2-fluorobenzyl)-4-methyl-1H-pyrazol-3-yl]-5-methoxy-N-(pyridin-4-yl)pyrimidin-4-amine, 2-[1-(2,6-dichlorobenzyl)-5-methoxy-4-methyl-1H-pyrazol-3-yl]-5-methoxy-N-(pyridin-4-yl)pyrimidin-4-amine, 2-[5-cyclopropyl-1-(4-ethoxy-2,6-difluorobenzyl)-4-methyl-1H-pyrazol-3-yl]-5-methoxy-N-(pyridin-4-yl)pyrimidin-4-amine, 2-[5-cyclopropyl-1-(4-ethoxy-2,6-difluorobenzyl)-4-methyl-1H-pyrazol-3-yl]-4-(pyridin-4-ylamino)pyrimidin-5-ol, 2-[5-cyclopropyl-1-(4-ethoxy-2,6-difluorobenzyl)-4-methyl-1H-pyrazol-3-yl]-5-[2-(dimethylamino)ethoxy]-N-(pyridin-4-yl)pyrimidin-4-amine, {3-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]oxetan-3-yl}methanol, 2-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)ethanol, 4-({2-[1-(2-fluorobenzyl)-5-methoxy-1H-pyrazol-3-yl]-5-methoxypyrimidin-4-yl}amino)pyridine-3-carboxamide, 2,4-dichloro-3-({5-cyclopropyl-3-[5-methoxy-4-(pyridin-4-ylamino) pyrimidin-2-yl]-4-methyl-1H-pyrazol-1-yl}methyl)benzoic acid.

or an N-oxide, a salt, a tautomer or a stereoisomer of said compound, or a salt of said N-oxide, tautomer or stereoisomer.

Another aspect of the invention are compounds of formula (I) selected from the group consisting of:

2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol, 2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine,
1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methanesulfonamide,
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 1,
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 2,
2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)pyrimidin-4-amine,
[3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}methyl)oxetan-3-yl]-methanol,
2-[5-cyclopropyl-1-(4-ethoxy-2,6-difluorobenzyl)-4-methyl-1H-pyrazol-3-yl]-5-[3-(methylsulfonyl)propoxy]-N-(pyridin-4-yl)pyrimidin-4-amine,
4-({2-[5-cyclopropyl-1-(4-ethoxy-2,6-difluorobenzyl)-4-methyl-1H-pyrazol-3-yl]-5-methoxypyrimidin-4-yl}amino)nicotinamide,
4-({2-[5-cyclopropyl-1-(4-ethoxy-2,6-difluorobenzyl)-4-methyl-1H-pyrazol-3-yl]pyrimidin-4-yl}amino)nicotinamide,
2-[5-cyclopropyl-1-(4-methoxybenzyl)-4-methyl-1H-pyrazol-3-yl]-5-methoxy-N-(pyridin-4-yl)pyrimidin-4-amine,
2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-4-(pyridin-4-ylamino)pyrimidine-5-carbonitrile,
4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile,
ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate,
4-({2-[5-cyclopropyl-1-(4-ethoxy-2,6-difluorobenzyl)-4-methyl-1H-pyrazol-3-yl]pyrimidin-4-yl}amino)nicotinonitrile,
2-[5-cyclopropyl-1-(4-ethoxy-2,6-difluorobenzyl)-4-methyl-1H-pyrazol-3-yl]-5-(methylsulfonyl)-N-(pyridin-4-yl)pyrimidin-4-amine,
2-[5-cyclopropyl-1-(4-ethoxy-2,6-difluorobenzyl)-4-methyl-1H-pyrazol-3-yl]-5-(isopropylsulfonyl)-N-(pyridin-4-yl)pyrimidin-4-amine,
ethyl 4-({2-[5-cyclopropyl-1-(4-ethoxy-2,6-difluorobenzyl)-4-methyl-1H-pyrazol-3-yl]pyrimidin-4-yl}amino)nicotinate,
2-[4-ethyl-1-(2-fluorobenzyl)-5-methoxy-1H-pyrazol-3-yl]-5-methoxy-N-(pyridin-4-yl)pyrimidin-4-amine,
ethyl 4-({2-[4-ethyl-1-(2-fluorobenzyl)-5-methoxy-1H-pyrazol-3-yl]-5-methoxypyrimidin-4-yl}amino)nicotinate,
2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 1,
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 2,
2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine,
2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine,
2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine,
4-({2-[5-cyclopropyl-1-(4-ethoxy-2,6-difluorobenzyl)-4-methyl-1H-pyrazol-3-yl]-5-methoxypyrimidin-4-yl}amino)nicotinic acid,
4-({2-[5-cyclopropyl-1-(4-ethoxy-2,6-difluorobenzyl)-4-methyl-1H-pyrazol-3-yl]pyrimidin-4-yl}amino)nicotinic acid,
4-({2-[4-ethyl-1-(2-fluorobenzyl)-5-methoxy-1H-pyrazol-3-yl]-5-methoxypyrimidin-4-yl}amino)nicotinic acid,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-methylnicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-hydroxynicotinamide,
4-({2-[4-ethyl-1-(2-fluorobenzyl)-5-methoxy-1H-pyrazol-3-yl]-5-methoxypyrimidin-4-yl}amino)nicotinamide.
or an N-oxide, a salt, a tautomer or a stereoisomer of said compound, or a salt of said N-oxide, tautomer or stereoisomer.

Another aspect of the invention are compounds of formula (I) selected from the group consisting of:
2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol,
2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine,
1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methanesulfonamide,
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 1, 5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 2,
2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)pyrimidin-4-amine,
[3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}methyl)oxetan-3-yl]-methanol,
2-[5-cyclopropyl-1-(4-ethoxy-2,6-difluorobenzyl)-4-methyl-1H-pyrazol-3-yl]-5-[3-(methylsulfonyl)propoxy]-N-(pyridin-4-yl)pyrimidin-4-amine,
4-({2-[5-cyclopropyl-1-(4-ethoxy-2,6-difluorobenzyl)-4-methyl-1H-pyrazol-3-yl]-5-methoxypyrimidin-4-yl}amino)nicotinamide,
4-({2-[5-cyclopropyl-1-(4-ethoxy-2,6-difluorobenzyl)-4-methyl-1H-pyrazol-3-yl]pyrimidin-4-yl}amino)nicotinamide,
2-[5-cyclopropyl-1-(4-methoxybenzyl)-4-methyl-1H-pyrazol-3-yl]-5-methoxy-N-(pyridin-4-yl)pyrimidin-4-amine,
2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-4-(pyridin-4-ylamino)pyrimidine-5-carbonitrile,
4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile,
ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate,
4-({2-[5-cyclopropyl-1-(4-ethoxy-2,6-difluorobenzyl)-4-methyl-1H-pyrazol-3-yl]pyrimidin-4-yl}amino)nicotinonitrile,
ethyl 4-({2-[5-cyclopropyl-1-(4-ethoxy-2,6-difluorobenzyl)-4-methyl-1H-pyrazol-3-yl]pyrimidin-4-yl}amino)nicotinate,
2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine,
2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine,
2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine,
4-({2-[5-cyclopropyl-1-(4-ethoxy-2,6-difluorobenzyl)-4-methyl-1H-pyrazol-3-yl]-5-methoxypyrimidin-4-yl}amino)nicotinic acid,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-methylnicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-hydroxynicotinamide.

or an N-oxide, a salt, a tautomer or a stereoisomer of said compound, or a salt of said N-oxide, tautomer or stereoisomer.

Another aspect of the invention are compounds of formula (I) selected from the group consisting of:
2-[1-(4-ethoxy-2,6-difluorobenzyl)-5-methoxy-4-methyl-1H-pyrazol-3-yl]-5-methoxy-N-(pyridin-4-yl)pyrimidin-4-amine,
2-[5-(dimethylamino)-1-(2-fluorobenzyl)-1H-pyrazol-3-yl]-5-methoxy-N-(pyridin-4-yl)pyrimidin-4-amine,
2-[1-(2-fluorobenzyl)-5-methoxy-1H-pyrazol-3-yl]-5-methoxy-N-(pyridin-4-yl)pyrimidin-4-amine,
2-[5-ethoxy-1-(2-fluorobenzyl)-1H-pyrazol-3-yl]-5-methoxy-N-(pyridin-4-yl)pyrimidin-4-amine,
2-(1-benzyl-5-cyclopropyl-1H-pyrazol-3-yl)-5-methoxy-N-(pyridin-4-yl)pyrimidin-4-amine,
2-(1-benzyl-5-ethenyl-1H-pyrazol-3-yl)-5-methoxy-N-(pyridin-4-yl)pyrimidin-4-amine,
4-({2-[1-(2-fluorobenzyl)-5-methoxy-1H-pyrazol-3-yl]-5-methoxypyrimidin-4-yl}amino)pyridine-3-carbonitrile,
2-[5-cyclopropyl-1-(4-methoxybenzyl)-1H-pyrazol-3-yl]-5-methoxy-N-(pyridin-4-yl)pyrimidin-4-amine,
2-[5-cyclopropyl-1-(2,6-dichlorobenzyl)-4-methyl-1H-pyrazol-3-yl]-5-methoxy-N-(pyridin-4-yl)pyrimidin-4-amine,
2-[5-cyclopropyl-1-(2-fluorobenzyl)-4-methyl-1H-pyrazol-3-yl]-5-methoxy-N-(pyridin-4-yl)pyrimidin-4-amine,
2-[1-(2,6-dichlorobenzyl)-5-methoxy-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-4-(pyridin-4-ylamino)pyrimidin-5-ol,
2-[5-cyclopropyl-1-(4-ethoxy-2,6-difluorobenzyl)-4-methyl-1H-pyrazol-3-yl]-5-[2-(dimethylamino)ethoxy]-N-(pyridin-4-yl)pyrimidin-4-amine,
{3-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]oxetan-3-yl}methanol,
2-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)ethanol,
4-({2-[1-(2-fluorobenzyl)-5-methoxy-1H-pyrazol-3-yl]-5-methoxypyrimidin-4-yl}amino)pyridine-3-carboxamide,
2,4-dichloro-3-({5-cyclopropyl-3-[5-methoxy-4-(pyridin-4-ylamino)pyrimidin-2-yl]-4-methyl-1H-pyrazol-1-yl}methyl)benzoic acid,
2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol, 2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine, 1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methanesulfonamide, 5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 1, 5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 2, 2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)pyrimidin-4-amine,

[3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}methyl)oxetan-3-yl]-methanol, 2-[5-cyclopropyl-1-(4-ethoxy-2,6-difluorobenzyl)-4-methyl-1H-pyrazol-3-yl]-5-[3-(methylsulfonyl)propoxy]-N-(pyridin-4-yl)pyrimidin-4-amine, 4-({2-[5-cyclopropyl-1-(4-ethoxy-2,6-difluorobenzyl)-4-methyl-1H-pyrazol-3-yl]-5-methoxypyrimidin-4-yl}amino)nicotinamide, 4-({2-[5-cyclopropyl-1-(4-ethoxy-2,6-difluorobenzyl)-4-methyl-1H-pyrazol-3-yl]pyrimidin-4-yl}amino)nicotinamide, 2-[5-cyclopropyl-1-(4-methoxybenzyl)-4-methyl-1H-pyrazol-3-yl]-5-methoxy-N-(pyridin-4-yl)pyrimidin-4-amine, 2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine, 2-[5-cyclopropyl-1-(4-ethoxy-2,6-difluorobenzyl)-4-methyl-1H-pyrazol-3-yl]-4-(pyridin-4-ylamino)pyrimidine-5-carbonitrile, 4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile, ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate, 4-({2-[5-cyclopropyl-1-(4-ethoxy-2,6-difluorobenzyl)-4-methyl-1H-pyrazol-3-yl]pyrimidin-4-yl}amino)nicotinonitrile, 2-[5-cyclopropyl-1-(4-ethoxy-2,6-difluorobenzyl)-4-methyl-1H-pyrazol-3-yl]-5-(methylsulfonyl)-N-(pyridin-4-yl)pyrimidin-4-amine, 2-[5-cyclopropyl-1-(4-ethoxy-2,6-difluorobenzyl)-4-methyl-1H-pyrazol-3-yl]-5-(isopropylsulfonyl)-N-(pyridin-4-yl)pyrimidin-4-amine, ethyl 4-({2-[5-cyclopropyl-1-(4-ethoxy-2,6-difluorobenzyl)-4-methyl-1H-pyrazol-3-yl]pyrimidin-4-yl}amino)nicotinate, 2-[4-ethyl-1-(2-fluorobenzyl)-5-methoxy-1H-pyrazol-3-yl]-5-methoxy-N-(pyridin-4-yl)pyrimidin-4-amine, ethyl 4-({2-[4-ethyl-1-(2-fluorobenzyl)-5-methoxy-1H-pyrazol-3-yl]-5-methoxypyrimidin-4-yl}amino)nicotinate, 2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine, 2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine, 2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 1, 2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 2, 2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine, 2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine, 2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine, 2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine, 4-({2-[5-cyclopropyl-1-(4-ethoxy-2,6-difluorobenzyl)-4-methyl-1H-pyrazol-3-yl]-5-methoxypyrimidin-4-yl}amino)nicotinic acid, 4-({2-[5-cyclopropyl-1-(4-ethoxy-2,6-difluorobenzyl)-4-methyl-1H-pyrazol-3-yl]pyrimidin-4-yl}amino)nicotinic acid, 4-({2-[4-ethyl-1-(2-fluorobenzyl)-5-methoxy-1H-pyrazol-3-yl]-5-methoxypyrimidin-4-yl}amino)nicotinic acid, 4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide, 4-({2-[5-cyclopropyl-1-(4-ethoxy-2,6-difluorobenzyl)-4-methyl-1H-pyrazol-3-yl]pyrimidin-4-yl}amino)-N-methylnicotinamide, 4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide, 4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide, 4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide, 4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide, 4-({2-[5-cyclopropyl-1-(4-ethoxy-2,6-difluorobenzyl)-4-methyl-1H-pyrazol-3-yl]-5-methoxypyrimidin-4-yl}amino)-N-hydroxynicotinamide, 4-({2-[4-ethyl-1-(2-fluorobenzyl)-5-methoxy-1H-pyrazol-3-yl]-5-methoxypyrimidin-4-yl}amino)nicotinamide or an N-oxide, a salt, a tautomer or a stereoisomer of said compound, or a salt of said N-oxide, tautomer or stereoisomer.

Another aspect of the invention are compounds of formula (I) selected from the group consisting of:

2-[1-(4-ethoxy-2,6-difluorobenzyl)-5-methoxy-4-methyl-1H-pyrazol-3-yl]-5-methoxy-N-(pyridin-4-yl)pyrimidin-4-amine, 2-[5-(dimethylamino)-1-(2-fluorobenzyl)-1H-pyrazol-3-yl]-5-methoxy-N-(pyridin-4-yl)pyrimidin-4-amine, 2-[1-(2-fluorobenzyl)-5-methoxy-1H-pyrazol-3-yl]-5-methoxy-N-(pyridin-4-yl)pyrimidin-4-amine, 2-[5-ethoxy-1-(2-fluorobenzyl)-1H-pyrazol-3-yl]-5-methoxy-N-(pyridin-4-yl)pyrimidin-4-amine, 2-(1-benzyl-5-cyclopropyl-1H-pyrazol-3-yl)-5-methoxy-N-(pyridin-4-yl)pyrimidin-4-amine, 2-(1-benzyl-5-ethenyl-1H-pyrazol-3-yl)-5-methoxy-N-(pyridin-4-yl)pyrimidin-4-amine, 4-({2-[1-(2-fluorobenzyl)-5-methoxy-1H-pyrazol-3-yl]-5-methoxypyrimidin-4-yl}amino)pyridine-3-carbonitrile,
2-[5-cyclopropyl-1-(4-methoxybenzyl)-1H-pyrazol-3-yl]-5-methoxy-N-(pyridin-4-yl)pyrimidin-4-amine,
2-[5-cyclopropyl-1-(2,6-dichlorobenzyl)-4-methyl-1H-pyrazol-3-yl]-5-methoxy-N-(pyridin-4-yl)pyrimidin-4-amine,
2-[5-cyclopropyl-1-(2-fluorobenzyl)-4-methyl-1H-pyrazol-3-yl]-5-methoxy-N-(pyridin-4-yl)pyrimidin-4-amine,
2-[1-(2,6-dichlorobenzyl)-5-methoxy-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-4-(pyridin-4-ylamino)pyrimidin-5-ol,
2-[5-cyclopropyl-1-(4-ethoxy-2,6-difluorobenzyl)-4-methyl-1H-pyrazol-3-yl]-5-[2-(dimethylamino)ethoxy]-N-(pyridin-4-yl)pyrimidin-4-amine,
{3-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]oxetan-3-yl}methanol,
2-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)ethanol,
4-({2-[1-(2-fluorobenzyl)-5-methoxy-1H-pyrazol-3-yl]-5-methoxypyrimidin-4-yl}amino)pyridine-3-carboxamide,
2,4-dichloro-3-({5-cyclopropyl-3-[5-methoxy-4-(pyridin-4-ylamino)pyrimidin-2-yl]-4-methyl-1H-pyrazol-1-yl}methyl)benzoic acid,
2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol,
2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine,
1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methanesulfonamide,
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 1,
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 2,
2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)pyrimidin-4-amine,
[3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}methyl)oxetan-3-yl]-methanol,
2-[5-cyclopropyl-1-(4-ethoxy-2,6-difluorobenzyl)-4-methyl-1H-pyrazol-3-yl]-5-[3-(methylsulfonyl)propoxy]-N-(pyridin-4-yl)pyrimidin-4-amine,
4-({2-[5-cyclopropyl-1-(4-ethoxy-2,6-difluorobenzyl)-4-methyl-1H-pyrazol-3-yl]-5-methoxypyrimidin-4-yl}amino)nicotinamide,
4-({2-[5-cyclopropyl-1-(4-ethoxy-2,6-difluorobenzyl)-4-methyl-1H-pyrazol-3-yl]pyrimidin-4-yl}amino)nicotinamide,
2-[5-cyclopropyl-1-(4-methoxybenzyl)-4-methyl-1H-pyrazol-3-yl]-5-methoxy-N-(pyridin-4-yl)pyrimidin-4-amine,
2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-4-(pyridin-4-ylamino)pyrimidine-5-carbonitrile,
4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile,
ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate,
4-({2-[5-cyclopropyl-1-(4-ethoxy-2,6-difluorobenzyl)-4-methyl-1H-pyrazol-3-yl]pyrimidin-4-yl}amino)nicotinonitrile,
ethyl 4-({2-[5-cyclopropyl-1-(4-ethoxy-2,6-difluorobenzyl)-4-methyl-1H-pyrazol-3-yl]pyrimidin-4-yl}amino)nicotinate,
2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine,
2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine,
2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine,
2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine
4-({2-[5-cyclopropyl-1-(4-ethoxy-2,6-difluorobenzyl)-4-methyl-1H-pyrazol-3-yl]-5-methoxypyrimidin-4-yl}amino)nicotinic acid,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-methylnicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide,
4-({2-[5-cyclopropyl-1-(4-ethoxy-2,6-difluorobenzyl)-4-methyl-1H-pyrazol-3-yl]-5-methoxypyrimidin-4-yl}amino)-N-hydroxynicotinamide
or an N-oxide, a salt, a tautomer or a stereoisomer of said compound, or a salt of said N-oxide, tautomer or stereoisomer.

Still another aspect of the invention are
2-[1-(2-fluorobenzyl)-5-methoxy-1H-pyrazol-3-yl]-5-methoxy-N-(pyridin-4-yl)pyrimidin-4-amine and
4-({2-[1-(2-fluorobenzyl)-5-methoxy-1H-pyrazol-3-yl]-5-methoxypyrimidin-4-yl}amino)pyridine-3-carbonitrile.

One aspect of the invention are compounds of formula (I) as described in the examples as characterized by their names in the title as claimed in claim 5 and their structures as well as the subcombinations of all residues specifically disclosed in the compounds of the examples.

Another aspect of the present invention are the intermediates as used for their synthesis.

If embodiments of the invention as disclosed herein relate to compounds of formula (I), it is understood that those embodiments refer to the compounds of formula (I) as disclosed in any of the claims and the examples.

Another aspect of the invention are compounds of formula (I), wherein
$R^1$, $R^2$ is independently from one another hydrogen or halogen (especially fluorine, chlorine, bromine).

Another aspect of the invention are compounds of formula (I), wherein
$R^1$, $R^2$ is fluorine or chlorine.

Another aspect of the invention are compounds of formula (I), wherein
$R^1$, $R^2$ is fluorine.

Another aspect of the invention are compounds of formula (I), wherein
$R^1$, $R^2$ is —S-phenyl.

A further aspect of the invention are compounds of formula (I), wherein
$R^3$ is hydrogen, 1-4C-alkoxy, halogen, 1-4C-alkyl, 2-4C-alkenyl or 3-6C-cycloalkyl.

Still another aspect of the invention are compounds of formula (I), wherein
$R^3$ is hydrogen or 1-4C-alkoxy.

Still another aspect of the invention are compounds of formula (I), wherein
$R^3$ is —C(O)OH.

Another aspect of the invention are compounds of formula (I), wherein
$R^3$ is halogen, 1-4C-alkyl, 2-4C-alkenyl or 3-6C-cycloalkyl.

A further aspect of the invention are compounds of formula (I), wherein
$R^3$ is either in the ortho position or in the meta position in relation to $R^1$ or $R^2$.

Another aspect of the invention are compounds of formula (I), wherein
$R^3$ is in the ortho position in relation to $R^1$ or $R^2$.

Another aspect of the invention are compounds of formula (I), wherein
$R^3$ is in the para position in relation to the point of attachment of the phenyl ring to the benzylic methylene group.

A further aspect of the invention are compounds of formula (I), wherein
$R^1$, $R^2$ is fluorine and $R^3$ is 1-4C-alkoxy.

Still a further aspect of the invention are compounds of formula (I), wherein
n is 1.

A further aspect of the invention are compounds of formula (I), wherein
n is 3.

A further aspect of the invention are compounds of formula (I), wherein
m is 1.

Still another aspect of the invention are compounds of formula (I), wherein
$R^4$ is hydroxy, 1-4Calkoxy (which is optionally substituted with hydroxy or $NR^9R^{10}$), —S-(1-4C-alkyl), —S(O)-(1-4C-alkyl), —SO$_2$-(1-4C-alkyl) or

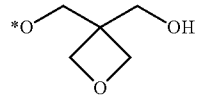

whereby the * is the point of attachment.

A further aspect of the invention are compounds of formula (I), wherein
$R^4$ is —S-(1-4C-alkyl), —S(O)-(1-4C-alkyl), —SO$_2$-(1-4C-alkyl).

Still another aspect of the invention are compounds of formula (I), wherein
$R^4$ is hydroxy, 1-4Calkoxy (which is optionally substituted with hydroxy or $NR^9R^{10}$, or

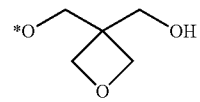

whereby the * is the point of attachment.

Another aspect of the invention are compounds of formula (I), wherein
$R^4$ is hydrogen,
(c) 1-6C-alkoxy opt. subst. with
  1-2 OH, $NR^9R^{10}$, 1-4C-alkyl-S—, 1-4C-alkyl-S(O)—, 1-4C-alkyl-S(O)$_2$—, S(O)$_2NR^9R^{10}$,
(d)

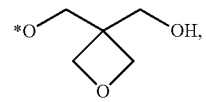

whereby the * is the point of attachment,
(e)

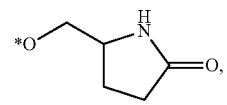

whereby the * is the point of attachment,

Another aspect of the invention are compounds of formula (I), wherein
$R^4$ is hydrogen, 1-6C-alkoxy which is opt. subst. with 1-4C-alkyl-S—, 1-4C-alkyl-S(O)—, 1-4C-alkyl-S(O)$_2$—, S(O)$_2NR^9R^{10}$.

Another aspect of the invention are compounds of formula (I), wherein
$R^4$ is hydrogen.

Another aspect of the invention are compounds of formula (I), wherein
$R^5$ is (c)

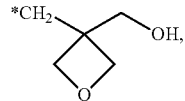

whereby the * is the point of attachment,
(e) —C(O)-(1-6C-alkylen)-O-(1-6C-alkyl),
(f) —C(O)-(1-6C-alkylen)-O-(1-6C-alkylen)-O-(1-6C-alkyl).

Another aspect of the invention are compounds of formula (I), wherein
$R^5$ is hydrogen.

A further aspect of the invention are compounds of formula (I), wherein
$R^6$ is hydrogen, cyano or $(CO)NR^{11}R^{12}$.

A further aspect of the invention are compounds of formula (I), wherein
$R^6$ is hydrogen, cyano, $C(O)NR^{11}R^{12}$, $C(O)OR^{13}$ or $C(O)NHOH$.

Another aspect of the invention are compounds of formula (I), wherein
$R^6$ $C(O)NR^{11}R^{12}$.

Still a further aspect of the invention are compounds of formula (I), wherein
$R^6$ is $C(O)OR^{13}$.

Still another aspect of the invention are compounds of formula (I), wherein
$R^6$ is hydrogen or —C(O)NH—OH, —C(O)NH-(1-3C-alkyl)-OH or —C(O)NH-(1-3C-alkyl)-SO$_2$-(1-3C-alkyl), especially hydrogen or —C(O)NH—OH, —C(O)NH—(CH$_2$)$_2$—OH, —C(O)NH—(CH$_2$—)$_2$—SO$_2$—CH$_3$.

Still a further aspect of the invention are compounds of formula (I), wherein
$R^6$ is in 3-position of the pyridine.

Another aspect of the invention are compounds of formula (I), wherein
$R^7$ is 1-4C-alkyl.

One aspect of the invention are compounds of formula (I), wherein
$R^7$ is 2-4C-alkenyl, 1-4C-alkoxy, 3-6C-cycloalkyl, $NR^9R^{10}$, especially is vinyl, methoxy, ethoxy, cyclopropyl or —N(CH$_3$)$_2$.

One aspect of the invention are compounds of formula (I), wherein
$R^7$ is hydrogen.

A further aspect of the invention are compounds of formula (I), wherein
$R^8$ is hydrogen or methyl and $R^7$ is not hydrogen.

A further aspect of the invention are compounds of formula (I), wherein
$R^8$ is hydrogen or methyl, ethyl and $R^7$ is not hydrogen.
$R^9$, $R^{10}$ are hydrogen or methyl.

Another aspect of the invention are compounds of formula (I), wherein
$R^{11}$ is hydrogen and $R^{12}$ is hydrogen, (1-3C-alkyl), 1-3C-hydroxyalkyl or (1-3C-alkyl)-SO$_2$-(1-3C-alkyl), especially hydrogen, methyl, hydroxyethyl or 2-methylsulfonylethyl.

A further aspect of the invention are compounds of formula (I), wherein
$R^{13}$ is hydrogen or ethyl.

A further aspect of the invention are compounds of formula (I), wherein
$R^{13}$ is hydrogen.

Still a further aspect of the invention are compounds of formula (I), wherein
$R^{13}$ is 1-3C-alkyl, especially ethyl.

DEFINITIONS

Constituents which are optionally substituted as stated herein, may be substituted, unless otherwise noted, one or more times, independently from one another at any possible position. When any variable occurs more than one time in any constituent, each definition is independent.

Unless defined otherwise in the claims the constituents defined below can optionally be substituted, one or more times, identically or differently, with a substituent selected from:
hydroxy, halogen, cyano, 1-6C-alkyl, 1-4C-haloalkyl, 1-6C-alkoxy, —NR$^9$R$^{10}$, cyano, (=O), —C(O)NR$^{11}$R$^{12}$, —C(O)OR$^{13}$, —NHC(O)R$^{12}$, —NHS(O)$_2$R$^{12}$. An alkyl constituent being substituted more times by halogen includes also a completely halogenated alkyl moiety such as e.g. CF$_3$.

Should a constituent be composed of more than one part, e.g. —O-(1-6Calkyl)-(3-7C-cycloalkyl), the position of a possible substituent can be at any of these parts at any suitable position. A hyphen at the beginning of the constituent marks the point of attachment to the rest of the molecule. Should a ring be substituted the substitutent could be at any suitable position of the ring, also on a ring nitrogen atom if suitable.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

"1-6C-alkyl" is a straight-chain or branched alkyl group having 1 to 6 carbon atoms. Examples are methyl, ethyl, n propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Those parts of constituents containing an alkyl chain as a bridging moiety between two other parts of the constituent which usually is called an "alkylene" moiety is defined in line with the definition for alkyl above including the preferred length of the chain e.g. methylen, ethylene, n-propylen, iso-propylen, n-butylen, isobutylene, tert-butylen.

"2-6C-Alkenyl" is a straight chain or branched alkenyl radical having 2 to 6 carbon atoms. Examples are the but-2-enyl, but-3-enyl (homoallyl), prop-1-enyl, prop-2-enyl (allyl) and the ethenyl (vinyl) radicals.

"Mono- or di-1-4C-alkylamino" radicals contain in addition to the nitrogen atom, independently one or two of the above mentioned 1-4C-alkyl radicals. Examples are the methylamino, the ethylamino, the isopropylamino, the dimethylamino, the diethylamino and the diisopropylamino radical.

"Halogen" within the meaning of the present invention is iodine, bromine, chlorine or fluorine, preferably "halogen" within the meaning of the present invention is chlorine or fluorine, should a halogen atom be needed as leaving group within the synthesis iodine or bromine are preferred.

"1-6C-Haloalkyl" is a straight-chain or branched alkyl group having 1 to 6 carbon atoms in which at least one hydrogen is substituted by a halogen atom. Examples are chloromethyl or 2-bromoethyl. For a partially or completely fluorinated C1-C4-alkyl group, the following partially or completely fluorinated groups are consid-ered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and penta-fluoroethyl, whereby difluoromethyl, trifluoromethyl, or 1,1,1-trifluoroethyl are preferred. All possible partially or completely fluorinated 1-6C-alkyl groups are considered to be encompassed by the term 1-6C-haloalkyl.

"1-6C-Hydroxyalkyl" is a straight-chain or branched alkyl group having 1 to 6 carbon atoms in which at least one hydrogen atom is substituted by a hydroxy group. Examples are hydroxymethyl, 1-hydroxyethyl, 2-hydroxyethyl, 1,2-dihydroxyethyl, 3-hydroxypropyl, 2-hydroxypropyl, 2,3-dihydroxypropyl, 3-hydroxy-2-methyl-propyl, 2-hydroxy-2-methyl-propyl, 1-hydroxy-2-methyl-propyl.

"1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, isobutoxy, sec-butoxy, tert-butoxy, propoxy, isopropoxy, ethoxy and methoxy radicals, preferred are methoxy, ethoxy, propoxy, isopropoxy. The alkyloxy radical unless stated otherwise may be substituted one or more times by hydroxy, halogen.

"1-6C-Haloalkoxy" represents radicals, which in addition to the oxygen atom, contain a straight-chain or branched alkyl radical having 1 to 6 carbon atoms in which at least one hydrogen is substituted by a halogen atom. Examples are —O—CFH$_2$, —O—CF$_2$H, —O—CF$_3$, —O—CH$_2$—CFH$_2$, —O—CH$_2$—CF$_2$H, —O—CH$_2$—CF$_3$. Preferred are —O—CF$_2$H, —O—CF$_3$, —O—CH$_2$—CF$_3$.

"3-7C-Cycloalkyl" stands for cyclopropyl, cyclobutyl, cyclopentyl, cyclohexyl or cycloheptyl, preferably cyclopropyl.

The NR$^9$R$^{10}$ group includes, for example, NH$_2$, N(H)CH$_3$, N(CH$_3$)$_2$, N(H)CH$_2$CH$_3$ and N(CH$_3$)CH$_2$CH$_3$.

The C(O)NR$^{11}$R$^{12}$ group includes, for example, C(O)NH$_2$, C(O)N(H)CH$_3$, C(O)N(CH$_3$)$_2$, C(O)N(H)CH$_2$CH$_3$, C(O)N(CH$_3$)CH$_2$CH$_3$ or C(O)N(CH$_2$CH$_3$)$_2$. If R$^{11}$ or R$^{12}$ are not hydrogen, they may be substituted by hydroxy, In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from NH$_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

Any such combination of a compound of formula (I) of the present invention with an anti-cancer agent as defined below is an embodiment of the invention.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, pommer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofuran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of claims 1-5 as described below, as well as their use for the synthesis of the compounds of claims 1-5, are one further aspect of the present invention. Preferred intermediates are the Intermediate Examples as disclosed below.

General Procedures

The compounds according to the invention can be prepared according to the following schemes 1 through 16, The schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, $R^5$, $R^6$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

One route for the preparation of compounds of general formula (Ia) is described in Scheme 1.

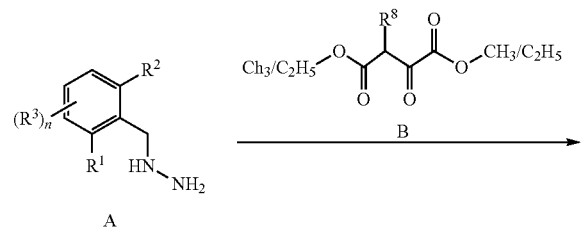

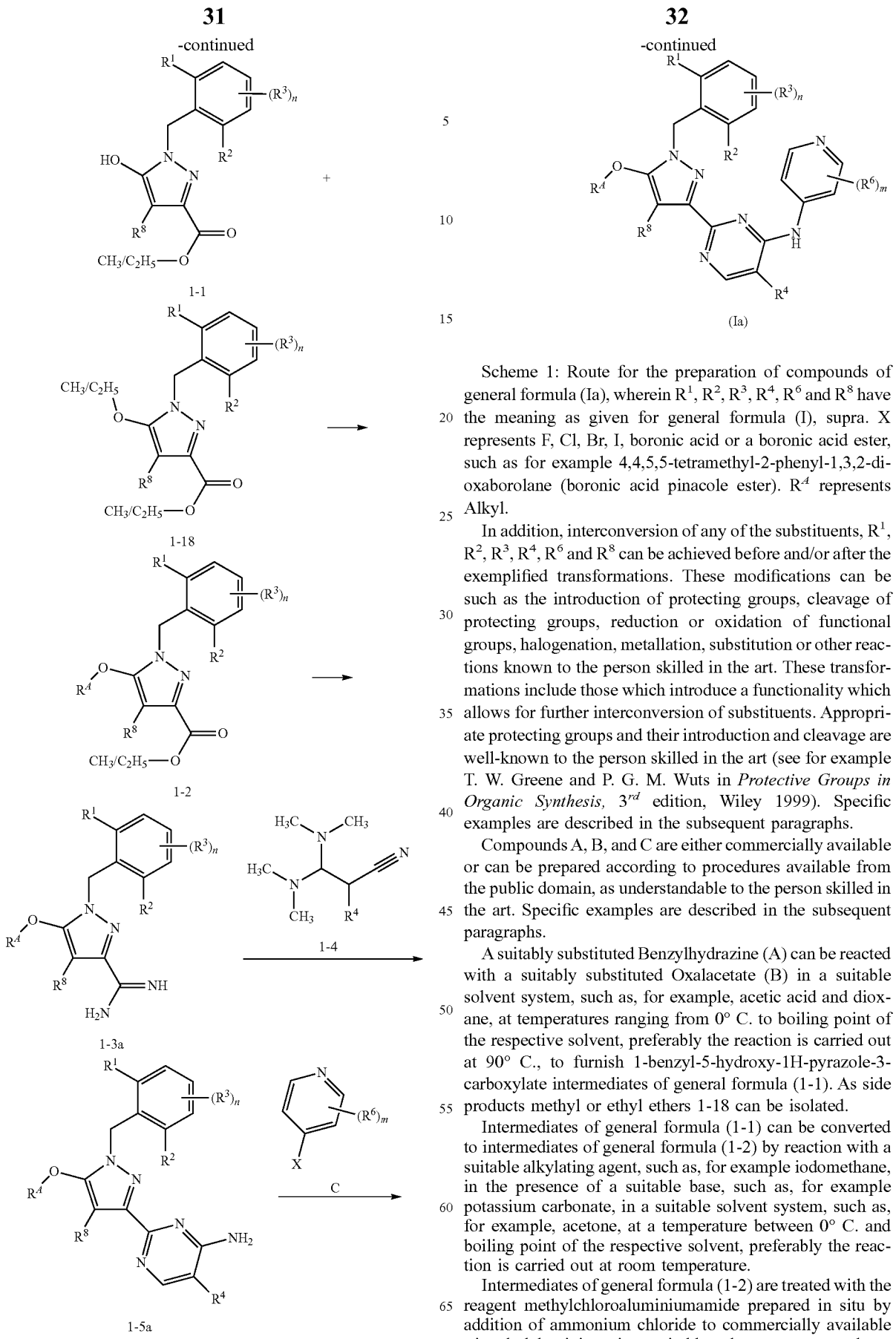

Scheme 1: Route for the preparation of compounds of general formula (Ia), wherein $R^1$, $R^2$, $R^3$, $R^4$, $R^6$ and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacole ester). $R^4$ represents Alkyl.

In addition, interconversion of any of the substituents, $R^1$, $R^2$, $R^3$, $R^4$, $R^6$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Compounds A, B, and C are either commercially available or can be prepared according to procedures available from the public domain, as understandable to the person skilled in the art. Specific examples are described in the subsequent paragraphs.

A suitably substituted Benzylhydrazine (A) can be reacted with a suitably substituted Oxalacetate (B) in a suitable solvent system, such as, for example, acetic acid and dioxane, at temperatures ranging from 0° C. to boiling point of the respective solvent, preferably the reaction is carried out at 90° C., to furnish 1-benzyl-5-hydroxy-1H-pyrazole-3-carboxylate intermediates of general formula (1-1). As side products methyl or ethyl ethers 1-18 can be isolated.

Intermediates of general formula (1-1) can be converted to intermediates of general formula (1-2) by reaction with a suitable alkylating agent, such as, for example iodomethane, in the presence of a suitable base, such as, for example potassium carbonate, in a suitable solvent system, such as, for example, acetone, at a temperature between 0° C. and boiling point of the respective solvent, preferably the reaction is carried out at room temperature.

Intermediates of general formula (1-2) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-3a).

Intermediates of general formula (1-3a) can be converted to intermediates of general formula (1-5a) by reaction with a suitably substituted 3,3-bis-(dimethylamino)propanenitrile of the general formula (1-4), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-5a) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Ia). Alternatively the following palladium catalysts can be used:
allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5a) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Ia).

Alternatively intermediates of general formula (1-5a) can be reacted with a suitable 4-halopyridine of the general formula (C), such as for example 4-fluoropyridine, in the presence of a suitable base, such as, for example sodium-hydride, in a suitable solvent system, such as, for example, N,N-dimethylformamide, in a temperature range from room temperature to the boiling point of the respective solvent, preferably the reaction is carried out at 90° C. to furnish compounds of general formula (Ia).

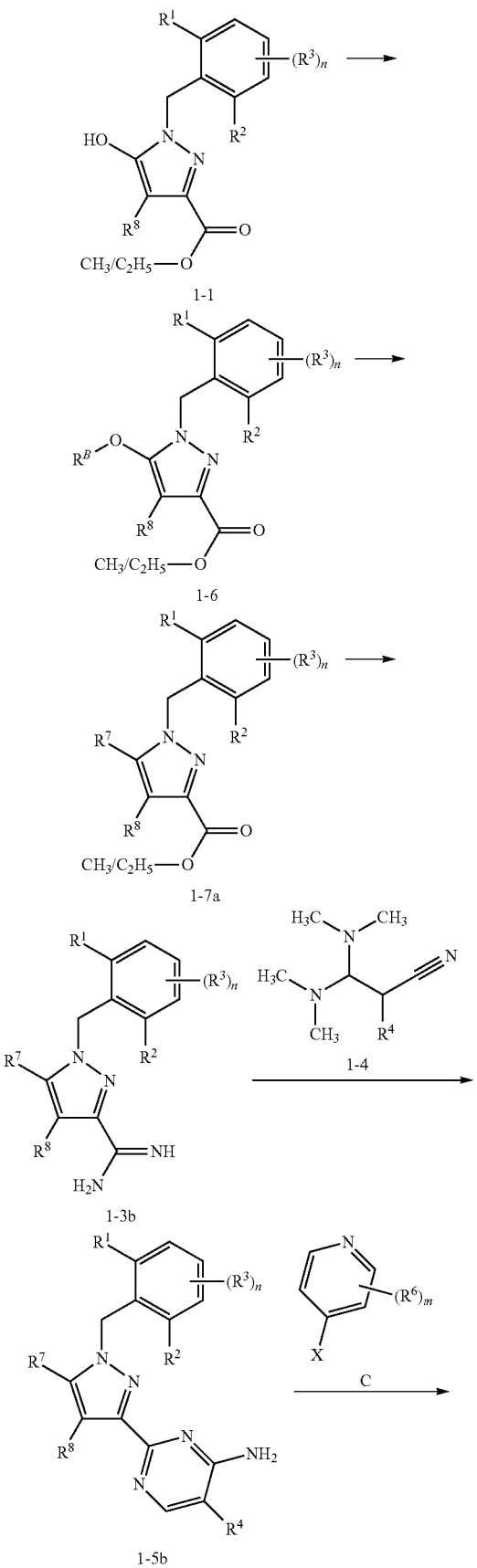

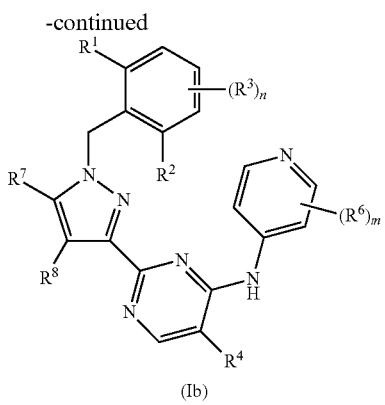

(Ib)

Scheme 2: Route for the preparation of compounds of general formula (Ib), wherein $R^1$, $R^2$, $R^3$, $R^4$, $R^6$, and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacol ester). $OR^B$ represents a leaving group, such as for example trifluoromethylsulfonate.

In addition, interconversion of any of the substituents, $R^1$, $R^2$, $R^3$, $R^4$, $R^6$, and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Compound C is either commercially available or can be prepared according to procedures available from the public domain, as understandable to the person skilled in the art. Specific examples are described in the subsequent paragraphs.

Intermediates of general formula (1-1) can be converted to intermediates of general formula (1-6) by reaction with a suitable sulfonic acid derivative, such as, for example triflic anhydride, in the presence of a suitable base, such as, for example pyridine, in a suitable solvent system, such as, for example, dichloromethane, at a temperature between 0° C. and boiling point of the respective solvent, preferably the reaction is carried out at room temperature.

Intermediates of general formula (1-6) can be converted to intermediates of general formula (1-7a) by reaction with boronic acid or boronic acid pinacole ester, such as, for example cyclopropylboronic acid, in the presence of a suitable base, such as, for example sodium carbonate, and a suitable palladium catalyst, such as for example tetrakis(triphenylphosphine)palladium(0), in a suitable solvent system, such as, for example, 1,2-dimethoxyethan, in a temperature range from room temperature to the boiling point of the respective solvent, preferably the reaction is carried out at 75° C.

Intermediates of general formula (1-7a) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-3b).

Intermediates of general formula (1-3b) can be converted to intermediates of general formula (1-5b) by reaction with a suitably substituted 3,3-bis-(dimethylamino)propanenitrile of the general formula (1-4), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-5b) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Ib). Alternatively the following palladium catalysts can be used: allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5b) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Ib).

Alternatively intermediates of general formula (1-5b) can be reacted with a suitable 4-halopyridine of the general formula (C), such as for example 4-fluoropyridine, in the presence of a suitable base, such as, for example sodiumhydride, in a suitable solvent system, such as, for example, N,N-dimethylformamide, in a temperature range from room temperature to the boiling point of the respective solvent, preferably the reaction is carried out at 90° C. to furnish compounds of general formula (Ib).

Scheme 3 (if $R^7$ = N(Alkyl)$_2$)

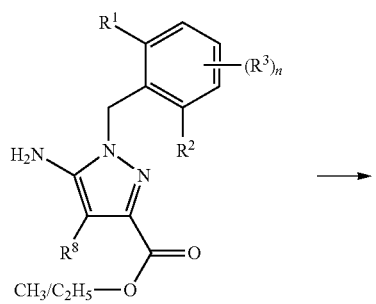

1-8

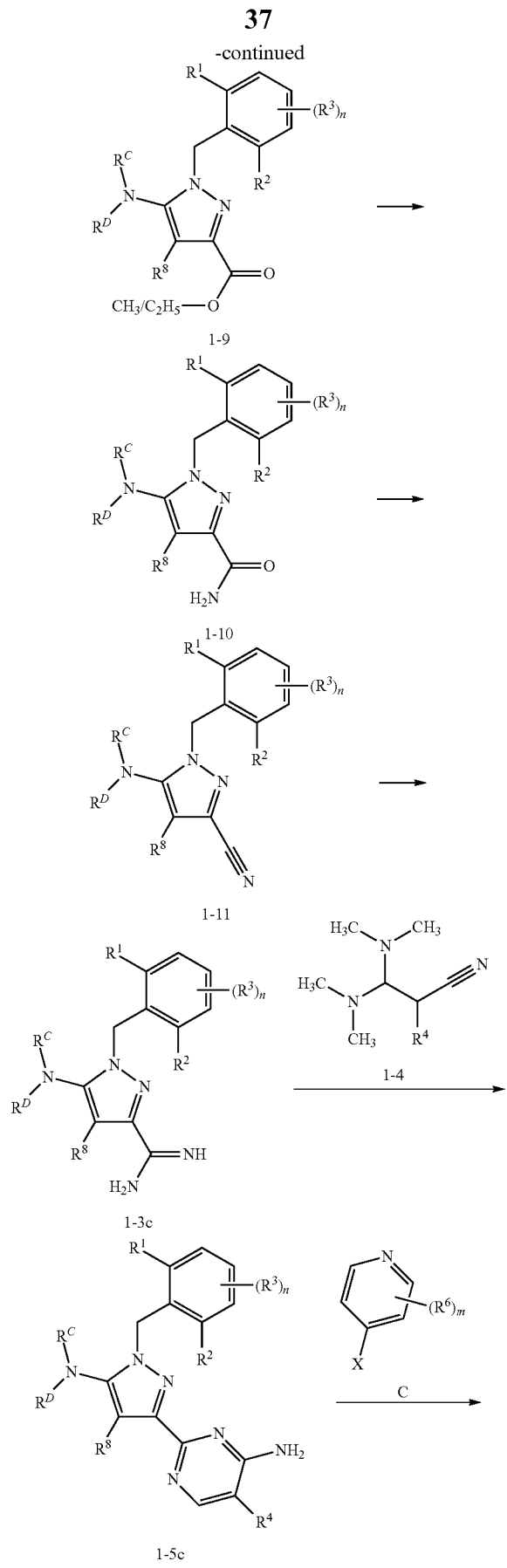

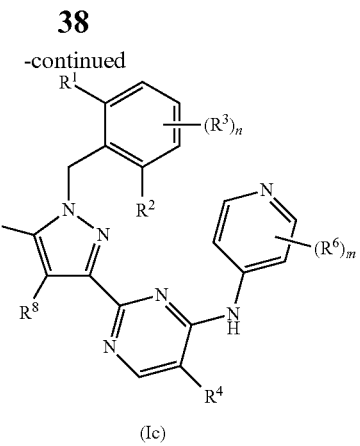

(Ic)

Scheme 3: Route for the preparation of compounds of general formula (Ic), wherein $R^1$, $R^2$, $R^3$, $R^4$, $R^6$ and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacole ester). $R^C$ and $R^D$ represent Alkyl-groups, especially 1-4Calkyl whereby the alkyl residues may be same or different.

In addition, interconversion of any of the substituents, $R^1$, $R^2$, $R^3$, $R^4$, $R^6$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Compound C is either commercially available or can be prepared according to procedures available from the public domain, as understandable to the person skilled in the art. Specific examples are described in the subsequent paragraphs.

Intermediates (1-8) can be prepared following the procedure depicted in Bioorg Med Chem Lett, 2001, 11/6, 781-784.

Intermediates of general formula (1-8) can be converted to intermediates of general formula (1-9) by reaction with a suitable alkylating agent, such as, for example, iodomethane, in the presence of a suitable base, such as, for example, lithiumhydride, in a suitable solvent system, such as, for example, N,N-dimethylformamide, at a temperature between 0° C. and boiling point of the respective solvent, preferably the reaction is carried out at room temperature.

Intermediates of general formula (1-9) can be converted to intermediates of general formula (1-10) by reaction with ammonia, in a suitable solvent system, such as, for example, methanol, at a temperature between 0° C. and boiling point of the respective solvent, preferably the reaction is carried out at 50° C., at a pressure between 1 and 10 bar, preferably the reaction is carried in a sealed vessel.

Intermediates of general formula (1-10) are treated with triflic anhydride, in a suitable solvent system, such as, for example, tetrahydrofuran, in the presence of a suitable base, such as, for example, pyridine, at a temperature between 0° C. and the boiling point of the respective solvent, preferably the reaction is carried out at room temperature, to form the desired intermediate of general formula (1-11).

Intermediates of general formula (1-11) can be converted to intermediates of general formula (1-3c) by reaction with a suitable alcoholate, such as, for example sodium methanolate, in a suitable solvent system, such as, for example, the corresponding alcohol, e.g. methanol, at a temperature between room temperature and the boiling point of the respective solvent, preferably the reaction is carried out at room temperature, and subsequent treatment with a suitable source of ammonium, such as for example, ammonium chloride in the presence of a suitable acid, such as for example acetic acid in a temperature range from room temperature to the boiling point of the respective solvent, preferably the reaction is carried out at 50° C.

Intermediates of general formula (1-3c) can be converted to intermediates of general formula (1-5c) by reaction with a suitably substituted 3,3-bis-(dimethylamino)propanenitrile of the general formula (1-4), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-5c) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Ic). Alternatively the following palladium catalysts can be used:
allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5c) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Ic).

Alternatively intermediates of general formula (1-5c) can be reacted with a suitable 4-halopyridine of the general formula (C), such as for example 4-fluoropyridine, in the presence of a suitable base, such as, for example sodiumhydride, in a suitable solvent system, such as, for example, N,N-dimethylformamide, in a temperature range from room temperature to the boiling point of the respective solvent, preferably the reaction is carried out at 90° C. to furnish compounds of general formula (Ic).

Compounds of general formula (Id) can also be synthesised according to the procedure depicted in Scheme 4.

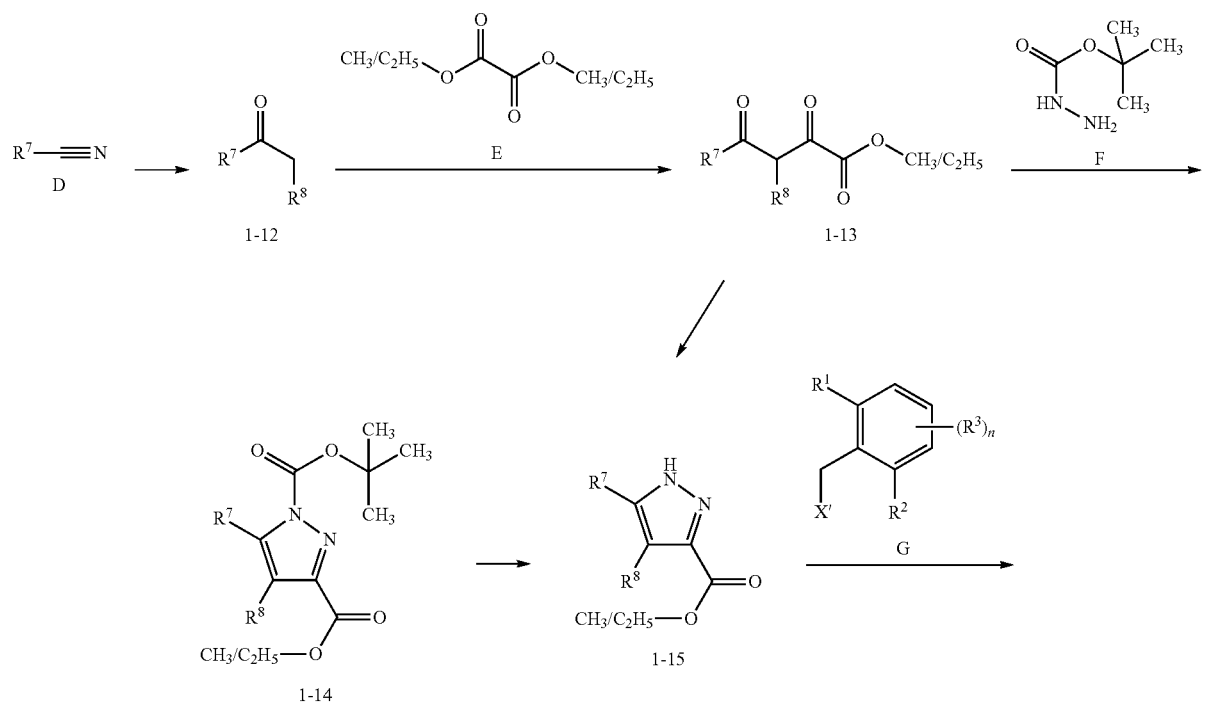

Scheme 4

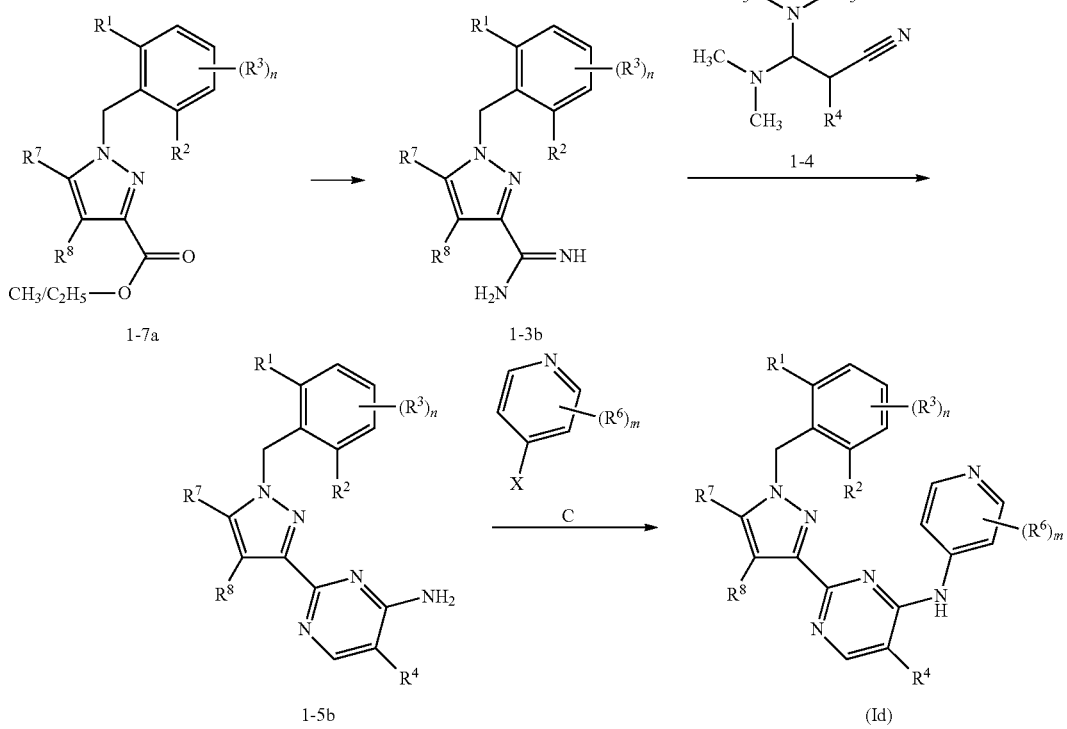

Scheme 4 Alternative route for the preparation of compounds of general formula (Id), wherein $R^1$, $R^2$, $R^3$, $R^4$, $R^6$, $R^7$ and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacole ester).

X' represents F, Cl, Br, I or a sulfonate, e.g. trifluormethylsulfonate or p-toluolsulfonate.

In addition, interconversion of any of the substituents, $R^1$, $R^2$, $R^3$, $R^4$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their intro-duction and cleavage are well-known to the person skilled in the art (see for ex-ample T. W. Greene and P. G. M. Wuts in *Protective Groups in Organic Synthesis*, $3^{rd}$ edition, Wiley 1999). Specific examples are described in the subsequent paragraphs.

Compounds C, D, E, F and G are either commercially available or can be prepared according to procedures available from the public domain, as understandable to the person skilled in the art as referred to below.

Intermediates of general formula D can be converted to intermediates of general formula (1-12) by reaction with a suitable organo metallic compound, such as, for example bromo(ethyl)magnesium, in a suitable solvent system, such as, for example, diethylether, at a temperature between 0° C. and boiling point of the respective solvent, preferably the reaction is carried out under reflux.

Intermediates of general formula (1-12) can be converted to intermediates of general formula (1-13) by reaction with a suitable oxalate (E), such as, for example diethyl oxalate, in the presence of a suitable base, such as, for example Bis-(trimethylsilyl)lithiumamide, in a suitable solvent system, such as, for example, diethylether, at a temperature between −78° C. and room temperature, preferably the reaction is carried out at room temperature.

Compounds of general formula (1-13) are converted to intermediates of general formula (1-14) by treatment with tert-butyl hydrazinecarboxylate (F), in a suitable solvent system, such as, for example, ethanol, in a temperature range from room temperature to the boiling point of the respective solvent, preferably the reaction is carried out at the boiling point of the respective solvent.

Compounds of general formula (1-14) are converted to intermediates of general formula (1-15) by reaction under acidic conditions, such as, for example, hydrochloric acid, in a suitable solvent system, such as, for example, dioxane, in a temperature range from 0° C. to room temperature, preferably the reaction is carried out at room temperature.

Alternatively, compounds of general formula (1-13) can be converted directly to intermediates of general formula (1-15) by treatment with hydrazine, in a suitable solvent system, such as, for example, ethanol, in a temperature range from room temperature to the boiling point of the respective solvent, preferably the reaction is carried out at the boiling point of the respective solvent.

Intermediates of general formula (1-15) can be reacted with a suitably substituted benzyl halide or benzyl sulfonate of general formula (G), such as, for example, a benzyl bromide, in a suitable solvent system, such as, for example, tetrahydrofuran, in the presence of a suitable base, such as, for example, sodium hydride in a temperature range from 0° C. to the boiling point of the respective solvent, preferably the reaction is carried out at room temperature, to furnish compounds of general formula (1-7a).

Intermediates of general formula (1-7a) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-3b).

Intermediates of general formula (1-3b) can be converted to intermediates of general formula (1-5b) by reaction with a suitably substituted 3,3-bis-(dimethylamino)propanenitrile of the general formula (1-4), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-5b) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Id). Alternatively the following palladium catalysts can be used:
allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5b) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as, for example copper (II) acetate, in a suitable solvent system, such as, for example, trichloromethane, in a temperature range from room temperature to the boiling point of the respective solvent, preferably the reaction is carried out at room temperature to furnish compounds of general formula (Id).

Alternatively intermediates of general formula (1-5b) can be reacted with a suitable 4-halopyridine of the general formula (C), such as, for example 4-fluoropyridine, in the presence of a suitable base, such as, for example sodiumhydride, in a suitable solvent system, such as, for example, N,N-dimethylformamide, in a temperature range from room temperature to the boiling point of the respective solvent, preferably the reaction is carried out at 90° C. to furnish compounds of general formula (Ib).

Compounds of general formula (Id) can alternatively be synthesised from other compounds of general formula (Id-1) which is a compound of formula (Id) wherein $R^3$=methoxy or ethoxy, via debenzylation and subsequent benzylation according to the procedure depicted in Scheme 5.

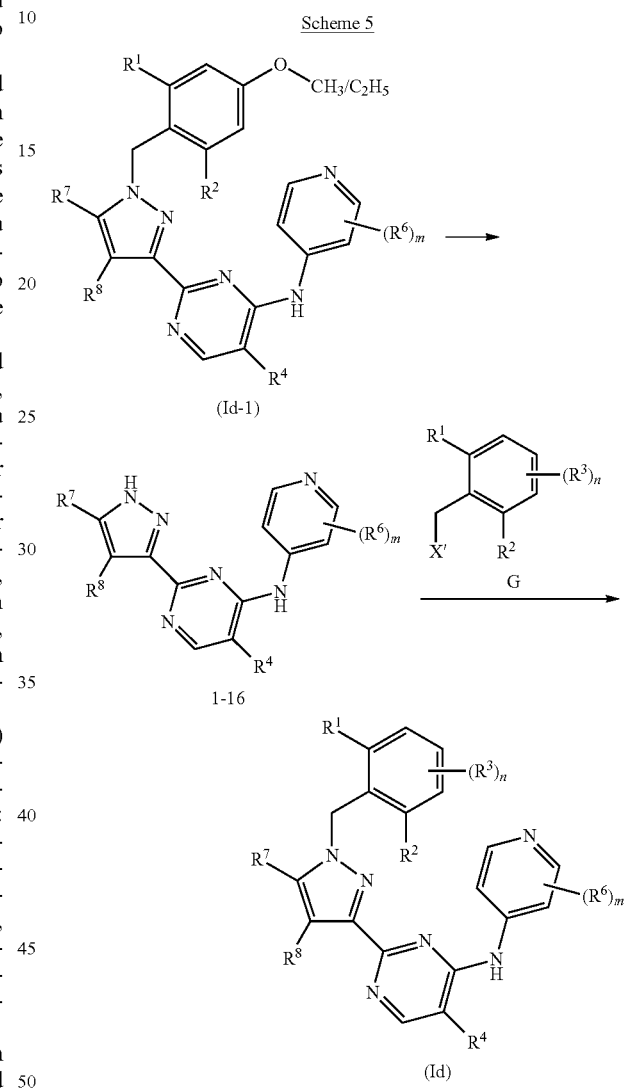

Scheme 5: Route for the preparation of compounds of general formula (Id), wherein $R^1$, $R^2$, $R^3$, $R^4$, $R^6$, $R^7$ and $R^8$ have the meaning as given for general formula (I), supra. X' represents F, Cl, Br, I or a sulfonate. In addition, interconversion of any of the substituents, $R^1$, $R^2$, $R^3$, $R^4$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

Compounds G are either commercially available or can be prepared according to procedures available from the public domain, as understandable to the person skilled in the art as referred to below scheme 1 above.

Compounds of general formula (Id-1) are converted to intermediates of general formula (1-16) by treatment with a suitable acid system, such as, for example a mixture of trifluoroacetic acid and trifluoromethanesulfonic acid, in a suitable solvent, such as, for example, dichloroethan, in a temperature range from room temperature to the boiling point of the respective solvent, preferably the reaction is carried out at room temperature.

Intermediates of general formula (1-16) can be reacted with a suitably substituted benzyl halide or benzyl sulfonate of general formula (G), such as, for example, a benzyl bromide, in a suitable solvent system, such as, for example, tetrahydrofuran, in the presence of a suitable base, such as, for example, sodium hydride in a temperature range from room temperature to the boiling point of the respective solvent, preferably the reaction is carried out at room temperature, to furnish compounds of general formula (Id).

Compounds of general formula (Ie), (Ie-1) and (If) can be synthesised from compounds of general formula (Id-2) which is a compound of formula (Ib) wherein $R^4$=methoxy, according to the procedure depicted in Scheme 6.

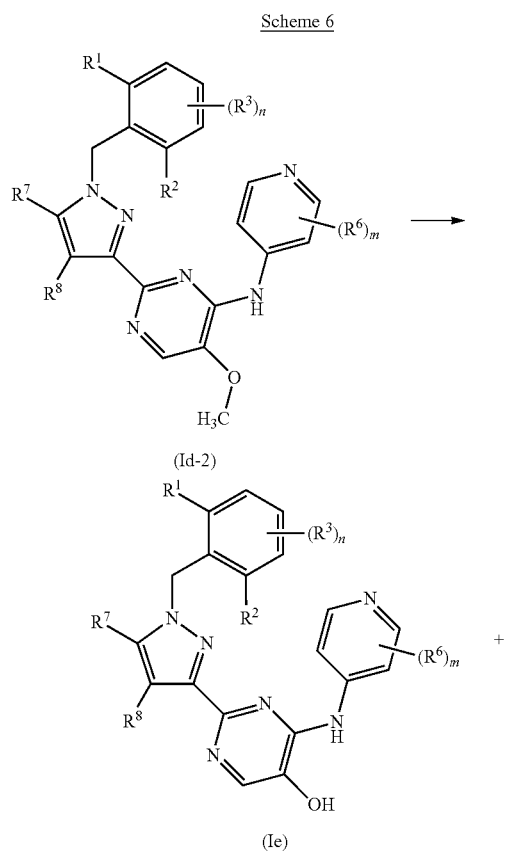

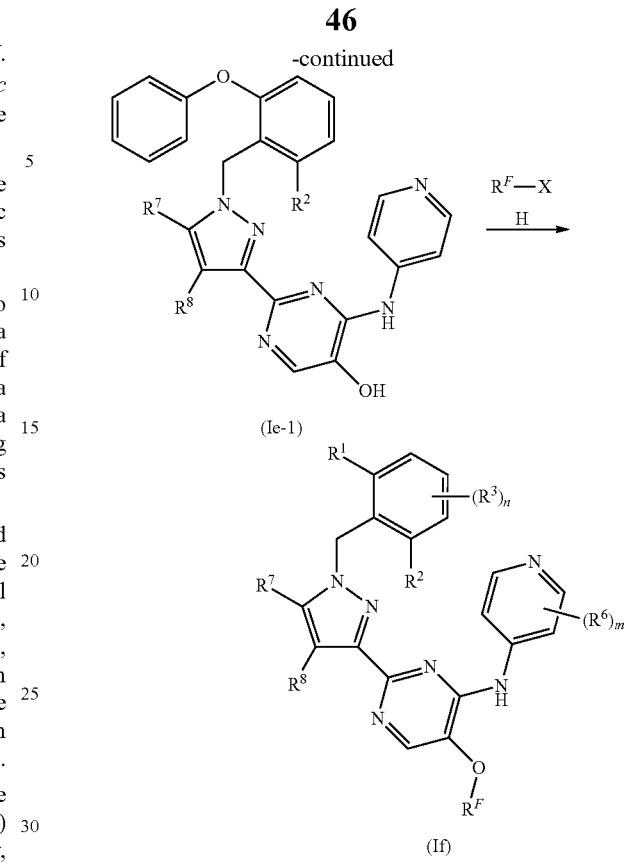

Scheme 6 Process for the preparation of compounds of general formula (If) via de-methylation of compounds of general formula (Id-2) to furnish compounds of general formula (Ie) and subsequent etherification to furnish compounds of general formula (If), wherein $R^1$, $R^2$, $R^3$, $R^4$, $R^6$, $R^7$ and $R^8$ have the meaning as given for general formula (I), supra. In addition, interconversion of any of the substituents, $R^1$, $R^2$, $R^3$, $R^4$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

Compounds of general formula H are commercially available, wherein X represents leaving group such as for example a Cl, Br or I, or X stands for an aryl sulfonate such as for example p-toluene sulfonate, or for an alkyl sulfonate such as for example methane sulfonate or trifluoromethane sulfonate (triflate group). $R^F$ represents alkyl (independently one or more times optionally substituted with alkoxy, OH, $NR^9R^{10}$, $SO_2NR^9R^{10}$,), heteroaryl or cycloalkyl, Compounds of general formula (Id-2) are converted to compounds of general formula (Ie) by treatment with a suitable demethylating agent, such as for example benzenethiol, in a suitable solvent, such as, for example, 1-methylpyrrolidin-2-one, in the presence of a suitable base, such as, for example potassium carbonate, in a temperature range from room temperature to the boiling point of the respective solvent, preferably the reaction is carried out at 190° C. In case of $R^1$ and $R^2$ being fluoride side product Ie-1 can be isolated.

Compounds of general formula (Ie) are then reacted with a compound of general formula (H) as mentioned above, in a suitable solvent, such as, for example, N,N-dimethylformamide, in the presence of a suitable base, such as, for example, potassium carbonate in a temperature range from room temperature to the boiling point of the respective solvent, preferably the reaction is carried out at room temperature, to furnish compounds of general formula (If).

Compounds of general formula (Ig) can be converted into compounds of general formula (Ih) according to the procedure depicted in Scheme 7.

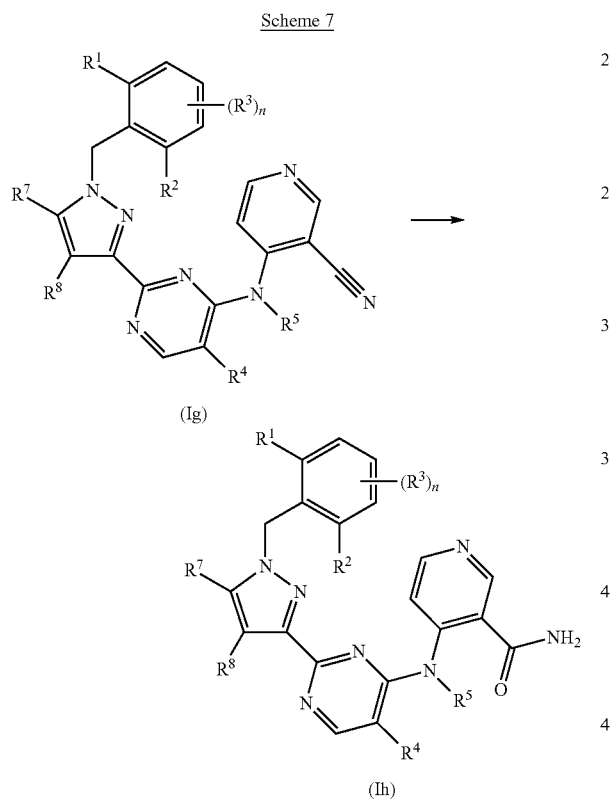

Scheme 7: Route for the preparation of compounds of general formula (Ih), via compounds of general formula (Ig) wherein $R^1$, $R^2$, $R^3$, $R^4$, $R^5$, $R^7$ and $R^8$ have the meaning as given for general formula (I), supra. In addition, interconversion of any of the substituents, $R^1$, $R^2$, $R^3$, $R^4$, $R^5$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Intermediates of general formula (Ig) are partially hydrolysed under acid conditions, such as, for example, concentrated sulfuric acid, at a temperature between 0° C. and the boiling point of the respective solvent, preferably the reaction is carried out at room temperature, to form the desired compound of general formula (Ih).

Compounds of general formula (Ie) can be converted into compounds of general formula (Ii) according to the procedure depicted in Scheme 8.

Scheme 8 During step 2 of this sequence the residues might potentially undergo a modification, e.g. reduction.

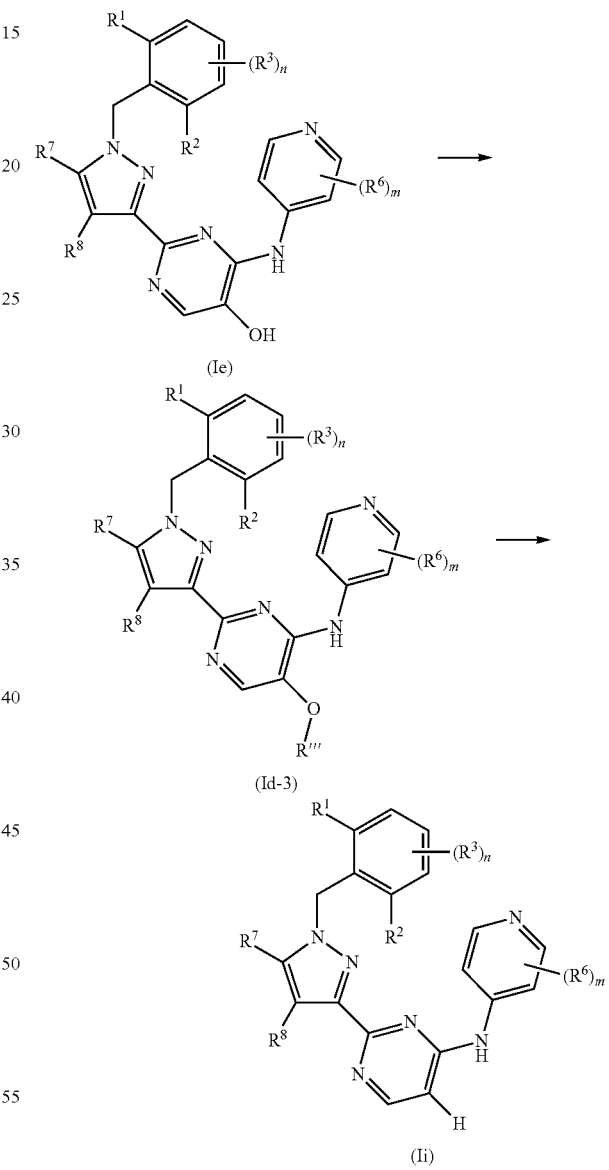

Scheme 8. Process for the transformation of compounds of general formula (Ie) into compounds of general formula (Ii), via an intermediate of the general formula (Id-3), wherein $R^1$, $R^2$, $R^3$, $R^6$, $R^7$ and $R^8$ have the meaning as given for general formula (I), supra. O—R'" represents a suitable leaving group, e.g. a trifluoromethylsulfonate group, nonafluorbutylsulfonyloxy.

In addition, interconversion of any of the substituents, $R^1$, $R^2$, $R^3$, $R^6$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their intro-duction and cleavage are well-known to the person skilled in the art (see for ex-ample T. W. Greene and P. G. M. Wuts in Protective Groups in Organic Synthesis, 3rd edition, Wiley 1999). Specific examples are described in the subsequent paragraphs.

Compounds of general formula (Ie) can be converted to intermediates of general formula (Id-3) by reaction with a suitable sulfonic acid derivative, such as, for example trifluoromethanesulfonic anhydride or 1,1,2,2,3,3,4,4,4-nonafluorobutane-1-sulfonyl fluoride, in a suitable solvent, such as, for example, dichloromethane, in the presence of a suitable base, such as, for example pyridine, in a temperature range from room temperature to the boiling point of the respective solvent, preferably the reaction is carried out at room temperature.

Intermediates of general formula (Id-3) can then be reacted with a suitable hydride source, such as, for example, triethylsilane, in a suitable solvent such as, for example, N,N-dimethyl formamide (DMF), in the presence of a suitable Pd-catalyst, such as, for example, palladium (II) acetate together with a suitable ligand, such as, for example, propane-1,3-diylbis(diphenylphosphane) in a temperature range from room temperature to the boiling point of the respective solvent, preferably the reaction is carried out at 60° C., to furnish compounds of general formula (Ii).

Compounds of general formula (Ii) which is a compound of formula (Id) wherein $R^4$=hydrogen, can be converted into compounds of general formula (Ij and Ik) according to the procedure depicted in Scheme 9.

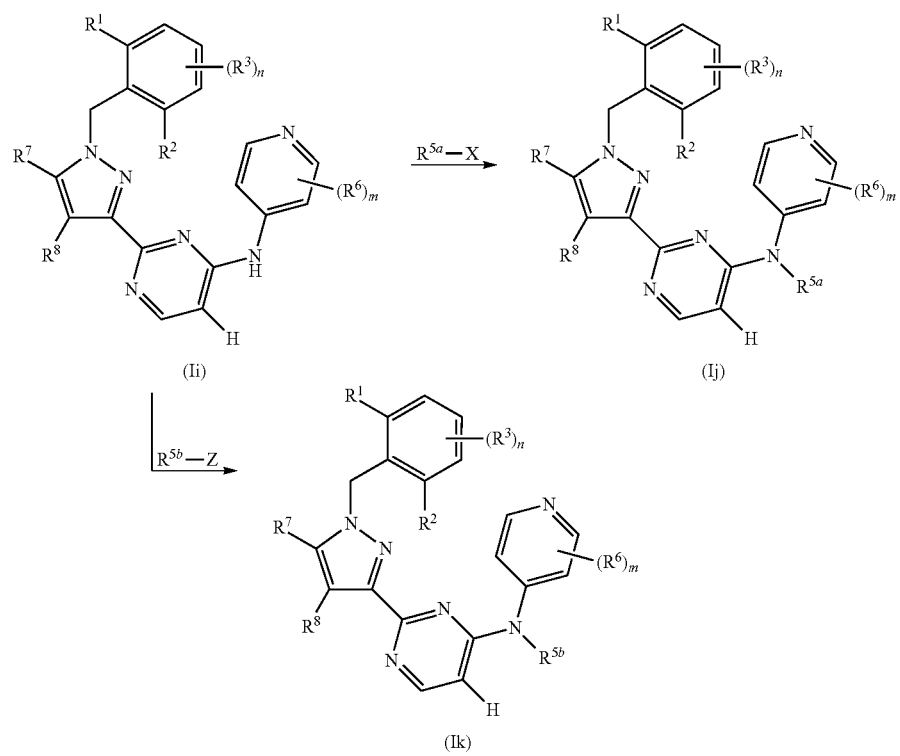

Scheme 9. Process for the transformation of compounds of general formula (Ii) into compounds of general formula (Ik) and (Ij), wherein $R^1$, $R^2$, $R^3$, $R^6$, $R^7$ and $R^8$ have the meaning as given for general formula (I), supra. $R^{5a}$ represents 1-6C-alkyl (independently one or more times optionally substituted with 1-3C-alkoxy, hydroxy,) and X as defined below scheme 1, supra, or for example 1,3,2-dioxathiolane 2-oxide.

$R^{5b}$ represents an acyl moiety, such as —C(O)-(1-6C-alkyl), —C(O)-(1-6C-alkylen)-O-(1-6C-alkyl), —C(O)-(1-6C-alkylen)-O-(1-6C-alkylen)-O-(1-6C-alkyl), and Z represents a halogen, hydroxy or —O—$R^{5b}$.

In addition, interconversion of any of the substituents, $R^1$, $R^2$, $R^3$, $R^6$, $R^{5a}$, $R^{5b}$, $R^6$, $R^7$ or $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent para-graphs.

Compounds of general formula (Ii) can be converted into compounds of general formula (Ij) by reaction with a suitable haloalkyl or dioxathiolane 2-oxide, such as, for example 1,3,2-dioxathiolane 2-oxide, in a suitable solvent system, such as, for example, N,N-dimethyl formamide, in the presence of a suitable base, such as, for example cesium carbonate, in a temperature range from room temperature to the boiling point of the respective solvent, preferably the reaction is carried out at 60° C.

Compounds of general formula (Ii) can be converted into compounds of general formula (Ik) by reaction with a suitable carbonic acid derivative, such as for example a carboxylic acid halogenide e.g. carboxylic acid chloride or a carboxylic acid anhydride, in a suitable solvent, such as, for example, dichloromethane, in the presence of a suitable base, such as, for example N,N-diethylethanamine, in a temperature range from room temperature to the boiling point of the respective solvent, preferably the reaction is carried out at room temperature.

Compounds of general formula (1-17) can be converted into compounds of general formula (1-4) according to the procedure depicted in Scheme 10.

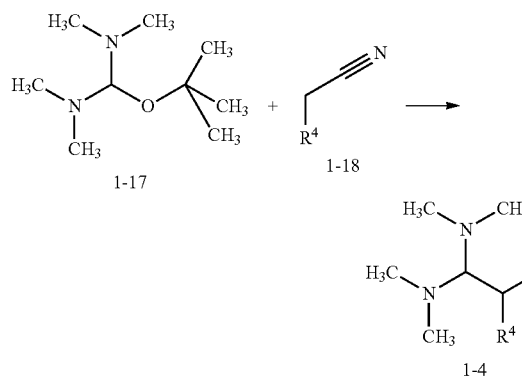

Scheme 10. Process for the transformation of compounds of general formula (I-17) into compounds of general formula (1-4)), wherein $R^4$ has the meaning as given for general formula (I).

Compounds of general formula (1-17) can be converted into compounds of general formula (1-4) by reaction with a suitable substituted cyanoalkyl, such as, for example methoxyacetonitrile, in a temperature range from room temperature to the boiling point of the respective solvent, preferably the reaction is carried out at 80° C.

Compounds of general formula (1-19) can be converted into compounds of general formula (G) according to the procedure depicted in Scheme 11.

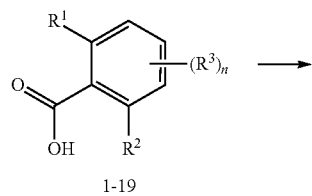

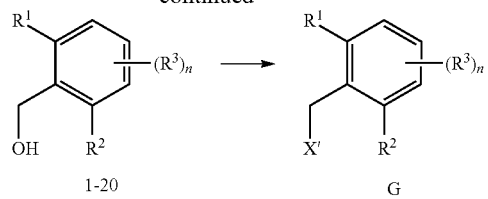

Scheme 11. Process for the transformation of compounds of general formula (1-19) into compounds of general formula (G), wherein $R^1$, $R^2$ and $R^3$ have the meaning as given for general formula (I). X' represents F, Cl, Br, I or a sulfonate, e.g. trifluormethylsulfonate or p-toluolsulfonate.

Compounds of general formula (1-19) can be converted into compounds of general formula (1-20) by reaction with a suitable reducing agend, such as, for example boran, in a suitable solvent system, such as, for example, THF, in a temperature range from −78° C. to boiling point of the respective solvent, preferably the reaction is carried out at room temperature.

Compounds of general formula (1-20) can be converted into compounds of general formula (G) by reaction with a suitable halogenation or sulfonylation agent, such as for example hydrogen bromide, in a suitable solvent, such as, for example, acidic acid, in a temperature range from 0° C. to the boiling point of the respective solvent, preferably the reaction is carried out at room temperature.

Compounds of general formula (1-21) can be converted into compounds of general formula (1-23) according to the procedure depicted in Scheme 12.

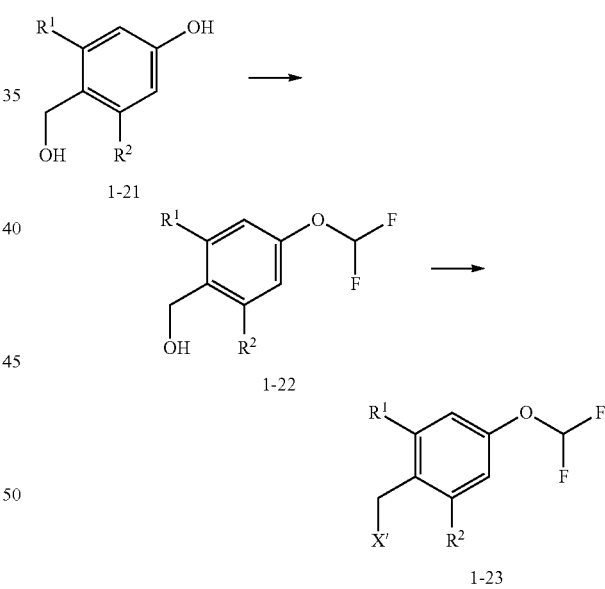

Scheme 12. Process for the transformation of compounds of general formula (1-21) into compounds of general formula (1-23), wherein $R^1$ and $R^2$ have the meaning as given for general formula (I). X' represents F, Cl, Br, I or a sulfonate, e.g. trifluormethylsulfonate or p-toluolsulfonate.

Compounds of general formula (1-21) can be converted into compounds of general formula (1-22) by reaction with a suitable difluoromethylation agend, such as, for example sodium chloro(difluoro)acetate, in a suitable solvent system, such as, for example, N,N-dimethylformamide, in the presence of a suitable base, such as, for example cesium carbonate, in a temperature range from room temperature to boiling point of the respective solvent, preferably the reaction is carried out at 100° C.

Compounds of general formula (1-22) can be converted into compounds of general formula (1-23) by reaction with a suitable halogenation or sulfonylation agent, such as for example hydrogen bromide, in a suitable solvent, such as, for example, acidic acid, in a temperature range from 0° C. to the boiling point of the respective solvent, preferably the reaction is carried out at room temperature.

Compounds of general formula (1-7b) can be converted into compounds of general formula (Id-4) according to the procedure depicted in Scheme 13.

Scheme 13

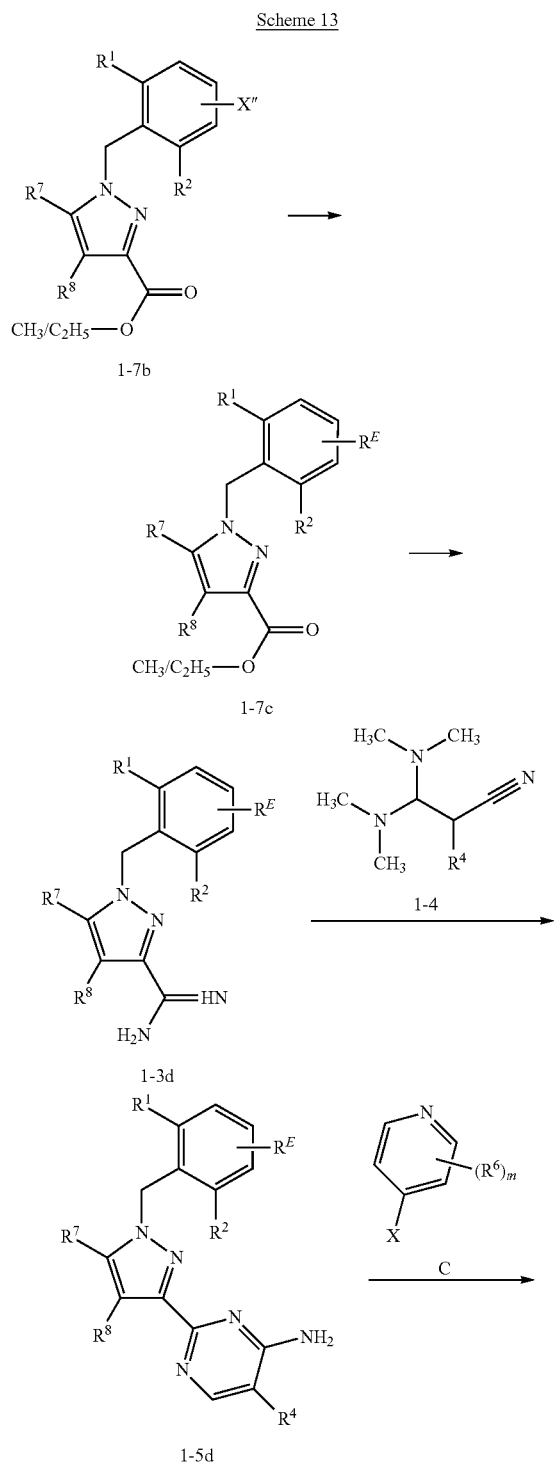

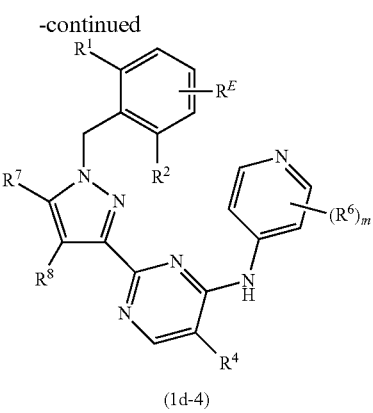

(Id-4)

Scheme 13 Alternative route for the preparation of compounds of general formula (Id-4), wherein $R^1$, $R^2$, $R^4$, $R^6$, $R^7$ and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacole ester).

X" represents Cl, Br, I or a sulfonate, e.g. trifluormethylsulfonate.

$R^E$ represents alkyl, cycloalkyl, alkenyl or aryl.

In addition, interconversion of any of the substituents, $R^1$, $R^2$, $R^4$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their intro-duction and cleavage are well-known to the person skilled in the art (see for ex-ample T. W. Greene and P. G. M. Wuts in *Protective Groups in Organic Synthesis*, 3$^{rd}$ edition, Wiley 1999). Specific examples are described in the subsequent paragraphs.

Compounds C, is either commercially available or can be prepared according to procedures available from the public domain, as understandable to the person skilled in the art as referred to below.

Intermediates of general formula (1-7b) can be converted to intermediates of general formula (1-7c) by reaction with boronic acid or boronic acid pinacole ester, such as, for example cyclopropylboronic acid, in the presence of a suitable base, such as, for example sodiumcarbonate, and a suitable palladium catalyst, such as for example tetrakis(triphenylphosphine)palladium(0), in a suitable solvent system, such as, for example, 1,2-dimethoxyethan, in a temperature range from room temperature to the boiling point of the respective solvent, preferably the reaction is carried out at 75° C.

Intermediates of general formula (1-7c) are treated with the reagent methylchloroaluminiumamide prepared in situ by addition of ammonium chloride to commercially available trimethylaluminium, in a suitable solvent system, such as, for example, toluene, at a temperature between 0° C. and the boiling point of the respective solvent, preferably the reaction is carried out at 80° C. and are quenched with a suitable solvent system, such as, for example, methanol, to form the desired intermediate of general formula (1-3d).

Intermediates of general formula (1-3d) can be converted to intermediates of general formula (1-5d) by reaction with a suitably substituted 3,3-bis-(dimethylamino)propanenitrile of the general formula (1-4), such as, for example 3,3-bis (dimethylamino)-2-methoxypropanenitrile, in the presence of a suitable base, such as, for example piperidine, in a suitable solvent system, such as, for example, 3-methylbutan-1-ol, in a temperature range from room temperature to the boiling point of the respective solvent, preferably the reaction is carried out at 100° C.

Intermediates of general formula (1-5d) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Id-4). Alternatively the following palladium catalysts can be used:
allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5d) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Id-4).

Alternatively intermediates of general formula (1-5d) can be reacted with a suitable 4-halopyridine of the general formula (C), such as for example 4-fluoropyridine, in the presence of a suitable base, such as, for example sodium-hydride, in a suitable solvent system, such as, for example, N,N-dimethylformamide, in a temperature range from room temperature to the boiling point of the respective solvent, preferably the reaction is carried out at 90° C. to furnish compounds of general formula (Id-4).

Compounds of general formula (1-3b) can be converted into compounds of general formula (Id) according to the procedure depicted in Scheme 14.

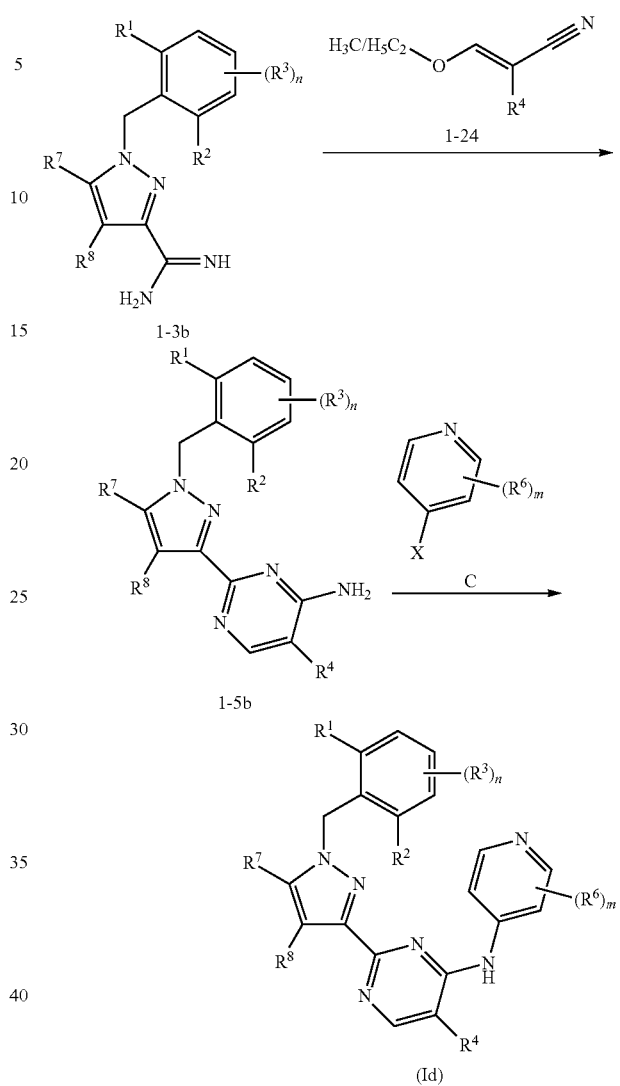

Scheme 14 Alternative route for the preparation of compounds of general formula (Id), wherein $R^1$, $R^2$, $R^3$, $R^4$, $R^6$, $R^7$ and $R^8$ have the meaning as given for general formula (I), supra. X represents F, Cl, Br, I, boronic acid or a boronic acid ester, such as for example 4,4,5,5-tetramethyl-2-phenyl-1,3,2-dioxaborolane (boronic acid pinacole ester).

In addition, interconversion of any of the substituents, $R^1$, $R^2$, $R^3$, $R^4$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their intro-duction and cleavage are well-known to the person skilled in the art (see for ex-ample T. W. Greene and P. G. M. Wuts in *Protective Groups in Organic Synthesis*, $3^{rd}$ edition, Wiley 1999). Specific examples are described in the subsequent paragraphs.

Compound C is either commercially available or can be prepared according to procedures available from the public domain, as understandable to the person skilled in the art as referred to below.

Intermediates of general formula (1-3b) can be converted to intermediates of general formula (1-5b) by reaction with a suitably substituted 3-methoxyacrylonitrile of the general formula (1-24), such as, for example (ethoxymethylene)malononitrile, in the presence of a suitable base, such as, for example sodium methanolate, in a suitable solvent system, such as, for example, methanol, in a temperature range from room temperature to the boiling point of the respective solvent, preferably the reaction is carried out at 65° C.

Intermediates of general formula (1-5b) can be reacted with a suitable 4-halopyridine of the general formula (C), such as, for example 4-bromopyridine, in the presence of a suitable base, such as, for example sodium 2-methylpropan-2-olate, and a suitable palladium catalyst, such as for example (1E,4E)-1,5-diphenylpenta-1,4-dien-3-one-palladium, in the presence of a suitable ligand, such as for example 1'-binaphthalene-2,2'-diylbis-(diphenylphosphane), in a suitable solvent system, such as, for example, N,N-dimethylformamide, in a temperature range from room temperature to the boiling point of the respective solvent, preferably the reaction is carried out at 100° C. to furnish compounds of general formula (Id). Alternatively the following palladium catalysts can be used:

allylpalladium chloride dimmer, dichlorobis(benzonitrile) palladium (II), palladium (II) acetate, palladium (II) chloride, tetrakis(triphenylphosphine)palladium (0), tris(dibenzylideneacetone)dipalladium (0) or the following ligands: racemic-2,2'-bis(diphenylphosphino)-1,1'-binaphthyl, rac-BINAP, 1,1'-bis-(diphenylphosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine).

Alternatively intermediates of general formula (1-5b) can be reacted with a suitable boronic acid or boronic acid pinacole ester of general formula (C), such as, for example (2-fluoropyridin-4-yl)boronic acid, in the presence of a suitable base, such as, for example triethylamine, a suitable activating agent such as for example N,N-dimethylpyridin-4-amine and a suitable copper salt, such as for example copper (II) acetate, in a suitable solvent system, such as, for example, trichloromethane, in a temperature range from room temperature to the boiling point of the respective solvent, preferably the reaction is carried out at room temperature to furnish compounds of general formula (Id).

Alternatively intermediates of general formula (1-5b) can be reacted with a suitable 4-halopyridine of the general formula (C), such as, for example 4-fluoropyridine, in the presence of a suitable base, such as, for example sodium-hydride, in a suitable solvent system, such as, for example, N,N-dimethylformamide, in a temperature range from room temperature to the boiling point of the respective solvent, preferably the reaction is carried out at 90° C. to furnish compounds of general formula (Id).

Compounds of general formula (II) can be converted into compounds of general formula (Im) and (In) according to the procedure depicted in Scheme 15.

Scheme 15

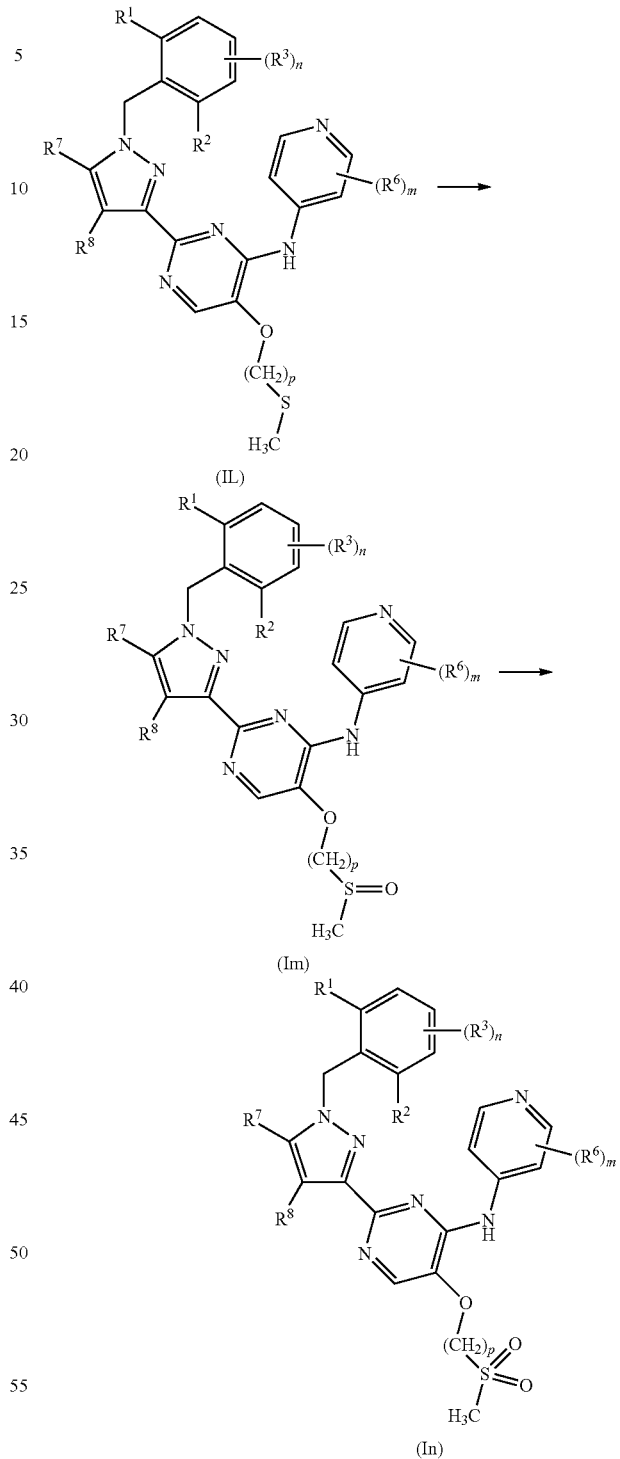

Scheme 15 Process for the preparation of compounds of general formula (In) via oxidation of compounds of general formula (Im), wherein $R^1$, $R^2$, $R^3$, $R^6$, $R^7$ and $R^8$ have the meaning as given for general formula (I), supra. p can be 1 to 6. In addition, interconversion of any of the substituents, $R^1$, $R^2$, $R^3$, $R^6$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art.

These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Compounds of general formula (IL) are converted to compounds of general formula (Im) by treatment with a suitable oxidation agent, such as for example 3-chlorobenzenecarboperoxoic acid, in a suitable solvent, such as, for example, chloroform, in a temperature range from 0° C. to the boiling point of the respective solvent, preferably the reaction is carried out at 0° C.

Compounds of general formula (Im) can be converted into compounds of general formula (In) by treatment with a suitable oxidation agent, such as for example hydrogen peroxide and the reagent diethyl azodicarboxylate, in a suitable solvent, such as, for example, tetrahydrofuran, in a temperature range from 0° C. to the boiling point of the respective solvent, preferably the reaction is carried out at 50° C.

Compounds of general formula (Ip) can be converted into compounds of general formula (Iqj) and (Ir) according to the procedure depicted in Scheme 16.

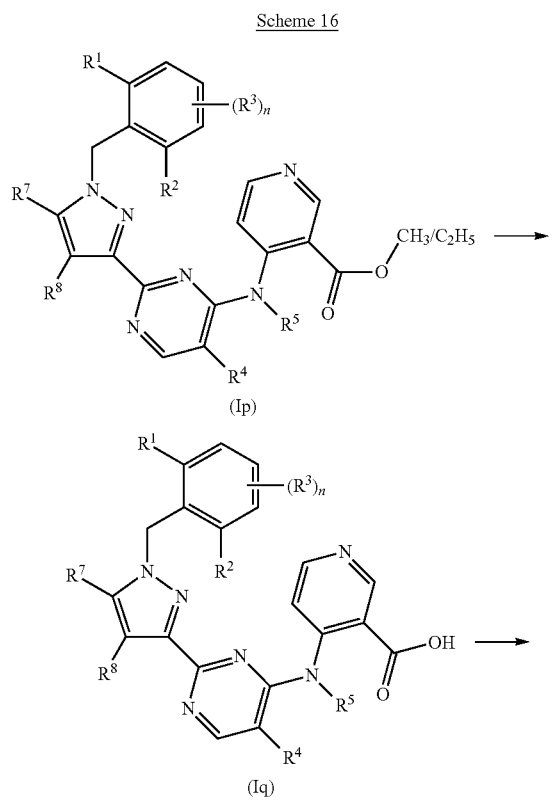

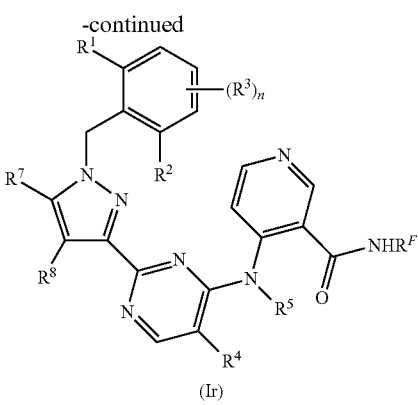

Scheme 16: Route for the preparation of compounds of general formula (Ir), via compounds of general formula (Iq) wherein $R^1$, $R^2$, $R^3$, $R^4$, $R^5$, $R^7$ and $R^8$ have the meaning as given for general formula (I), supra. In addition, interconversion of any of the substituents, $R^1$, $R^2$, $R^3$, $R^4$, $R^5$, $R^7$ and $R^8$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Intermediates of general formula (Ip) are converted to formula (Iq) by treatment with a suitable base, such as for example sodium hydroxide, in a suitable solvent, such as, for example, tetrahydrofuran and methanol, in a temperature range from 0° C. to the boiling point of the respective solvent, preferably the reaction is carried out at room temperature.

Intermediates of general formula (Iq) are converted to formula (Ir) by treatment with a suitable amine, such as for example 2-aminoethylmethyl sulfone, by addition of a suitable base, such as for example N,N-diisopropylethylamine, with a suitable coupling reagent, such as for example (benzotriazol-1-yloxy)tripyrrolidinophosphonium hexafluorophosphate, in a suitable solvent, such as, for example N,N-dimethylformamide, in a temperature range from 0° C. to the boiling point of the respective solvent, preferably the reaction is carried out at room temperature.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as meta-chloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

As mentioned supra, the compounds of the present invention have surprisingly been found to effectively inhibit Bub1 finally resulting in apoptosis and cell death and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

One aspect of the invention is the use of the compounds according to formula (I) for the treatment of cervical cancer, breast cancer, ovarian cancer, non-small cell lung cancer (NSCLC), prostate cancer, colon cancer, pancreas cancer, osteo sarcoma, acute myelogenous leukemia, Burkitt lymphoma, multiple myeloma, melanoma.

One aspect of the invention is the use of the compounds according to formula (I) for the treatment of cervical cancer, non-small cell lung cancer (NSCLC), prostate cancer, colon cancer, melanoma.

Another aspect of the invention is the use of the compounds according to formula (I) for the treatment of cervix tumors, NSCLC, prostate cancer, colon cancer and melanoma as well as a method of treatment of cervix tumors, NSCLC, prostate cancer, colon cancer and melanoma comprising administering an effective amount of a compound of formula (I). Another aspect of the invention is the use of the compounds according to formula (I) for the treatment of cervix tumors as well as a method of treatment of cervix tumors comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of apoptosis, especially for the treatment of hyperproliferative disorders or disorders responsive to induction of apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haemotological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised Powder for i.v. Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haemotological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

Substituted Benzylpyrazoles

Experimental Part

The following table lists the abbreviations used in this paragraph and in the Intermediate Examples and Examples section as far as they are not explained within the text body.

| Abbreviation | Meaning |
|---|---|
| aq. | aqueous |
| alloc | allyloxycarbonyl |
| boc | tert-butoxycarbonyl |
| br | broad |
| CI | chemical ionisation |
| d | doublet |
| dd | doublet of doublet |
| DAD | diode array detector |
| DCM | dichloromethane |
| DMF | N,N-dimethylformamide |
| EtOAc | ethyl acetate |
| Eq. | equivalent |
| ESI | electrospray (ES) ionisation |
| HATU | 2-(7-aza-1H-benzotriazole-1-yl)-1,1,3,3-tetramethyl-uronium hexafluorophosphate (CAS number 148893-10-1) |
| HPLC | high performance liquid chromatography |
| LC-MS | liquid chromatography mass spectrometry |
| m | multiplet |
| MS | mass spectrometry |
| n-BuLi | n-butyllithium |
| NMR | nuclear magnetic resonance spectroscopy: chemical shifts ($\delta$) are given in ppm. The chemical shifts were corrected by setting the DMSO signal to 2.50 ppm using unless otherwise stated. |
| PoraPak™; | a HPLC column obtainable from Waters |
| q | quartet |
| r.t. or rt | room temperature |
| RT | retention time (as measured either with HPLC or UPLC) in minutes |
| s | singlet |
| SM | starting material |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Isolera autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| System: | Waters Acquity UPLC-MS: Binary Solvent Manager, Sample Manager/Organizer, Column Manager, PDA, ELSD, SQD 3001 or ZQ4000 |
|---|---|
| System: | Waters Acquity UPLC-MS: Binary Solvent Manager, Sample Manager/Organizer, PDA, ELSD, |
| Column: | Acquity UPLC BEH C18 1.7 50 × 2.1 mm |
| Solvent: | A1 = water + 0.1% formic acid |
| | A2 = water + 0.2% ammonia |
| | B1 = acetonitrile |
| Gradient: | 0-1.6 min 1-99% B, 1.6-2.0 min 99% B |
| Flow: | 0.8 mL/min |
| Temperatuer: | 60° C. |
| Injektion: | 2.0 µL |
| Detection: | DAD scan range 210-400 nm -> Peaktable |
| | ELSD |
| | MS ESI+, ESI− Switch -> variouse scan ranges |
| Methods: | Method 1: Mass__100__1000 |
| | Method 2: Mass__160__1000 |
| | Method 3: Mass__160__2000 |
| | Method 4: Mass__160__1000__BasicReport |
| | Method 5: $NH_3$__Mass__100__1000 |
| | Method 6: $NH_3$__Mass__160__1000 |

Preparative HPLC Conditions

"Purification by preparative HPLC" in the subsequent specific experimental descriptions refers to (unless otherwise noted) the following conditions:

Analytics (Pre- and Post Analytics: Method B):

| System: | Waters Aqcuity UPLC-MS: Binary Solvent Manager, Sample Manager/Organizer, Column Manager, PDA, ELSD, SQD 3001 |
|---|---|
| Column: | Aqcuity BEH C18 1.7 50 × 2.1 mm |
| Solvent: | A = water + 0.1% formic acid |
| | B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µL |
| Detection: | DAD scan range 210-400 nm |
| | MS ESI+, ESI−, scan range 160-1000 m/z |
| | ELSD |

Preparation:

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = water + 0.1% formic acid |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Chiral HPLC Conditions

Chiral HPLC-data given in the subsequent specific experimental descriptions refer to the following conditions:

Analytics:

| System: | Dionex: Pump 680, ASI 100, Waters: UV-Detektor 2487 |
|---|---|
| Column: | Chiralpak IC 5 µm 150 × 4.6 mm |
| Solvent: | hexane/ethanol 80:20 + 0.1% diethylamine |
| Flow: | 1.0 mL/min |
| Temperature: | 25° C. |
| Solution: | 1.0 mg/mL ethanol/methanol 1:1 |
| Injection: | 5.0 µL |
| Detection: | UV 280 nm |

Preparation:

| System: | Agilent: Prep 1200, 2 × Prep Pump, DLA, MWD, Prep FC, ESA: Corona |
|---|---|
| Column: | Chiralpak IC 5 µm 250 × 30 mm |
| Solvent: | hexane/ethanol 80:20 + 0.1% diethylamine |
| Flow: | 40 mL/min |
| Temperature: | RT |
| Solution: | 660 mg/5.6 mL ethanol |
| Injection: | 8 × 0.7 mL |
| Detection: | UV 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Determination of Optical Rotation Conditions

Optical rotations were measured in dimethyl sulfoxide at 589 nm wavelength, 20° C., concentration 1.0000 g/100 mL, integration time 10 s, film thickness 100.00 mm.

EXAMPLES

Synthetic Intermediates

Intermediate 1-1-1

Preparation of ethyl 1-(4-ethoxy-2,6-difluorobenzyl)-5-hydroxy-4-methyl-1H-pyrazole-3-carboxylate

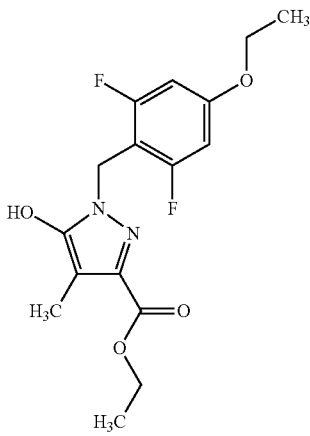 [SMILES: CCOC(=O)c1nn(Cc2c(F)cc(OCC)cc2F)c(O)c1C]

4.65 g of diethyl 2-methyl-3-oxobutanedioate (23.0 mmol, 1.00 eq.) were dissolved in 100 mL of dry dioxane under argon atmosphere. 2.1 mL of glacial acetic acid and 6.32 g of (4-ethoxy-2,6-difluorobenzyl)hydrazine dihydrochloride (23.00 mmol, 1.00 eq.) were added. The mixture was stirred for 16 hours at 90° C. bath temperature. The reaction mixture was evaporated in vacuo. The residue was stirred with ethyl acetate. The resulting suspension was filtered off and washed with ethyl acetate. The filter cake was dried in vacuo at 40° C. The filtrate was concentrated in vacuo and purified by flash chromatography (hexane/ethyl acetate-gradient with hexane 0-100%). The filter cake and the received purified compound of the flash chromatography were stirred together in ethyl acetate, filtered off and provided 3.95 g (11.3 mmol, 49%) of the analytically pure target compound.

$^1$H-NMR (300 MHz, DMSO-$d_6$): δ [ppm]=1.13-1.36 (m, 6H), 1.97 (s, 3H), 4.01 (q, 2H), 4.14 (q, 2H), 5.04 (s, 2H), 6.65-6.73 (m, 2H), 10.60 (br. s., 1H).

The following intermediates were prepared according to the same procedure:

| | | | |
|---|---|---|---|
| 1-1-2 | 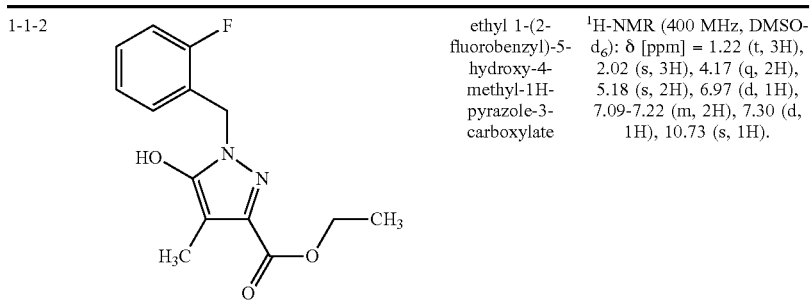 | ethyl 1-(2-fluorobenzyl)-5-hydroxy-4-methyl-1H-pyrazole-3-carboxylate | $^1$H-NMR (400 MHz, DMSO-$d_6$): δ [ppm] = 1.22 (t, 3H), 2.02 (s, 3H), 4.17 (q, 2H), 5.18 (s, 2H), 6.97 (d, 1H), 7.09-7.22 (m, 2H), 7.30 (d, 1H), 10.73 (s, 1H). |
| 1-1-3 | 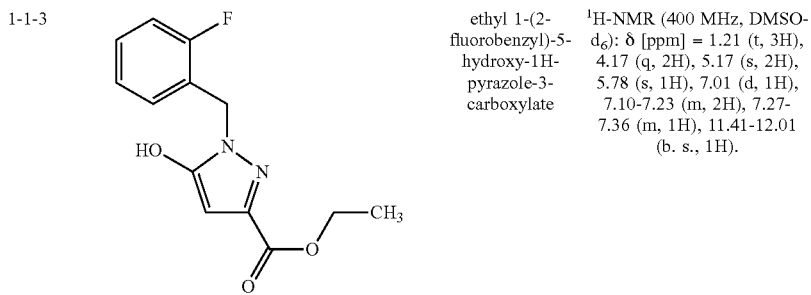 | ethyl 1-(2-fluorobenzyl)-5-hydroxy-1H-pyrazole-3-carboxylate | $^1$H-NMR (400 MHz, DMSO-$d_6$): δ [ppm] = 1.21 (t, 3H), 4.17 (q, 2H), 5.17 (s, 2H), 5.78 (s, 1H), 7.01 (d, 1H), 7.10-7.23 (m, 2H), 7.27-7.36 (m, 1H), 11.41-12.01 (b. s., 1H). |
| 1-1-4 | 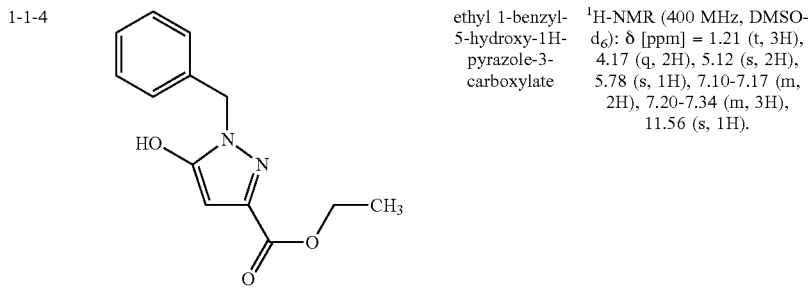 | ethyl 1-benzyl-5-hydroxy-1H-pyrazole-3-carboxylate | $^1$H-NMR (400 MHz, DMSO-$d_6$): δ [ppm] = 1.21 (t, 3H), 4.17 (q, 2H), 5.12 (s, 2H), 5.78 (s, 1H), 7.10-7.17 (m, 2H), 7.20-7.34 (m, 3H), 11.56 (s, 1H). |

| | | | |
|---|---|---|---|
| 1-1-5 | 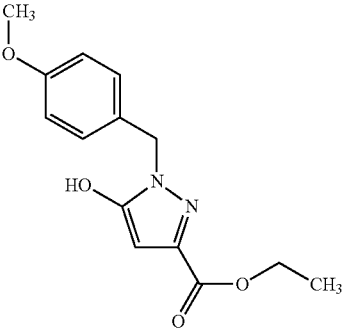 [SMILES: CCOC(=O)c1cc(O)n(Cc2ccc(OC)cc2)n1] | ethyl 5-hydroxy-1-(4-methoxybenzyl)-1H-pyrazole-3-carboxylate | $^1$H-NMR (300 MHz, DMSO-$d_6$): δ [ppm] = 1.21 (t, 3H), 3.68 (s, 3H), 4.17 (q, 2H), 5.03 (s, 2H), 5.75 (s, 1H), 6.85 (d, 2H), 7.11 (d, 2H), 11.32-11.62 (b. s, 1H). |
| 1-1-6 | 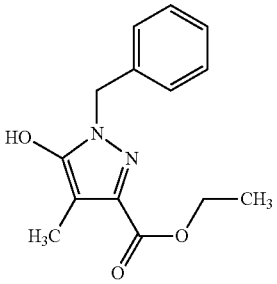 [SMILES: CCOC(=O)c1nn(Cc2ccccc2)c(O)c1C] | ethyl 1-benzyl-5-hydroxy-4-methyl-1H-pyrazole-3-carboxylate | $^1$H-NMR (400 MHz, DMSO-$d_6$): δ [ppm] = 1.26 (t, 3H), 2.05 (s, 3H), 4.21 (q, 2H), 5.16 (s, 2H), 7.16 (d, 2H), 7.22-7.39 (m, 3H), 10.56-10.82 (b. s, 1H). |
| 1-1-7 | 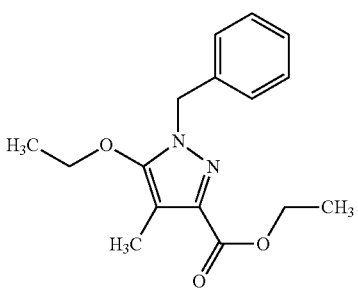 [SMILES: CCOC(=O)c1nn(Cc2ccccc2)c(OCC)c1C] | ethyl 1-benzyl-5-ethoxy-4-methyl-1H-pyrazole-3-carboxylate | $^1$H-NMR (400 MHz, DMSO-$d_6$): δ [ppm] = 1.22 (dt, 6H), 2.09 (s, 3H), 4.00 (q, 2H), 4.20 (q, 2H), 5.19 (s, 2H), 7.10-7.16 (m, 2H), 7.21-7.35 (m, 3H). |
| 1-1-8 | 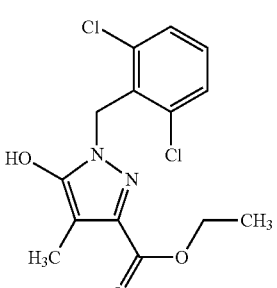 | ethyl 1-(2,6-dichlorobenzyl)-5-hydroxy-4-methyl-1H-pyrazole-3-carboxylate | $^1$H-NMR (400 MHz, DMSO-$d_6$): δ [ppm] = 1.18 (t, 3H), 2.00 (s, 3H), 4.13 (q, 2H), 5.29 (s, 2H), 7.33-7.41 (m, 1H), 7.44-7.51 (m, 2H), 10.61-10.82 (b. s, 1H). |
| 1-1-9 | 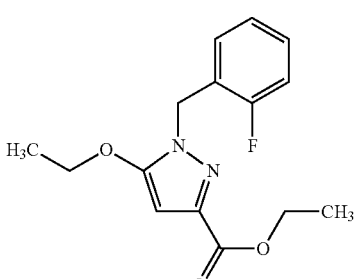 | ethyl 5-ethoxy-1-(2-fluorobenzyl)-1H-pyrazole-3-carboxylate | LC-MS: retention time: 1.24 min MS ES$^+$: 293.0 [M + H]$^+$ Method B |

| | | | |
|---|---|---|---|
| 1-1-10 SM = 1-26-1 | 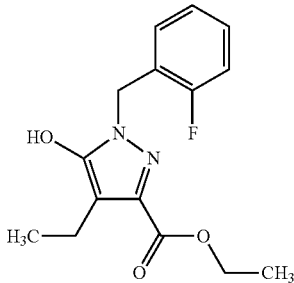 [SMILES: CCOC(=O)c1nn(Cc2ccccc2F)c(O)c1CC] | ethyl 4-ethyl-1-(2-fluorobenzyl)-5-hydroxy-1H-pyrazole-3-carboxylate | $^1$H-NMR (300 MHz, DMSO-$d_6$): δ [ppm] = 1.04 (t, 3H), 1.06 (t, 3H), 2.56 (q, 2H), 4.21 (q, 2H), 5.22 (s, 2H), 7.00 (td, 1H), 7.14-7.23 (m, 2H), 7.34 (m, 1H). |

Intermediate 1-2-1

Preparation of ethyl 1-(4-ethoxy-2,6-difluorobenzyl)-5-methoxy-4-methyl-1H-pyrazole-3-carboxylate

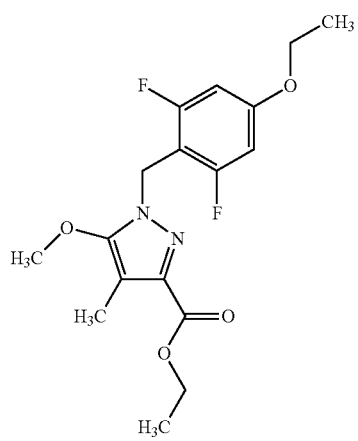 [SMILES: CCOC(=O)c1nn(Cc2c(F)cc(OCC)cc2F)c(OC)c1C]

3.95 g of ethyl 1-(4-ethoxy-2,6-difluorobenzyl)-5-hydroxy-4-methyl-1H-pyrazole-3-carboxylate 1-1-1 (11.6 mmol, 1.0 eq.) were dissolved in 50 mL of acetone. 1.45 mL of iodomethane (23.2 mmol, 2.0 eq.) and 5.78 g (41.8 mmol, 3.6 eq.) of potassium carbonate were added and stirred over for 24 hours at rt. 1.45 mL of iodomethane (23.2 mmol, 2.0 eq.) were added and the mixture was stirred for further 24 hours at rt. The suspension was filtered off over sea sand and the filtrate was concentrated in vacuo. The residue was extracted by DCM and water. The aqueous layer was extracted twice with DCM. The combined organic layers were dried over sodium sulfate and concentrated in vacuo. The residue was purified by flash chromatography to give 2.29 g (6.46 mmol, 55.7%) of analytically pure target compound.

$^1$H-NMR (300 MHz, DMSO-$d_6$): δ [ppm]=1.21 (t, 3H), 1.27 (t, 3H), 2.08 (s, 3H), 3.83 (s, 3H), 4.01 (q, 2H), 4.17 (q, 2H), 5.11 (s, 2H), 6.68-6.75 (m, 2H).

The following intermediates were prepared according to the same procedure:

| | | | |
|---|---|---|---|
| 1-2-2 | 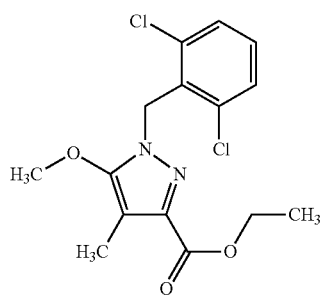 [SMILES: CCOC(=O)c1nn(Cc2c(Cl)cccc2Cl)c(OC)c1C] | ethyl 1-(2,6-dichlorobenzyl)-5-methoxy-4-methyl-1H-pyrazole-3-carboxylate | $^1$H-NMR (400 MHz, DMSO-$d_6$): δ [ppm] = 1.20 (t, 3H), 2.10 (s, 3H), 3.86 (s, 3H), 4.16 (q, 2H), 5.37 (s, 2H), 7.40 (dd, 1H), 7.48-7.51 (m, 2H). |
| 1-2-3 | 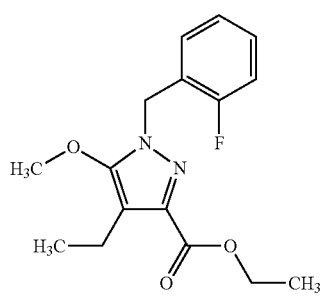 [SMILES: CCOC(=O)c1nn(Cc2ccccc2F)c(OC)c1CC] | ethyl 4-ethyl-1-(2-fluorobenzyl)-5-methoxy-1H-pyrazole-3-carboxylate | → |

Intermediate 1-3-1

Preparation of 1-(4-ethoxy-2,6-difluorobenzyl)-5-methoxy-4-methyl-1H-pyrazole-3-carboximidamide hydrochloride 1:1

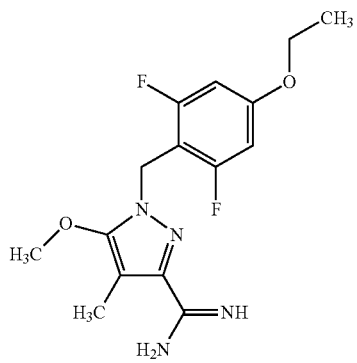 [SMILES: CCOc1cc(F)c(Cn2nc(C(=N)N)c(C)c2OC)c(F)c1]

1.73 g of ammonium chloride were suspended in 37 mL of dry toluene under nitrogen atmosphere and cooled down to 0° C. bath temperature. 16.2 mL of 2M trimethylaluminium solution in heptane (32.3 mmol, 5.0 eq.) were added dropwise. The mixture was stirred at rt until disappearance of gassing. 2.29 g of ethyl 1-(4-ethoxy-2,6-difluorobenzyl)-5-methoxy-4-methyl-1H-pyrazole-3-carboxylate 1-2-1 (6.46 mmol, 1.0 eq.) were dissolved in 13 mL of dry toluene and added dropwise to the reaction mixture and stirred for 24 hours at 80° C. bath temperature. The mixture was cooled down with an ice bath to 0° C. bath temperature, 35.6 mL of methanol were added and stirred for one hour at rt. The resulting suspension was filtered off and washed with methanol. The filtrate was concentrated in vacuo and the residue was stirred with DCM/methanol 9:1. The suspension was filtered off. The filter cake was washed twice with DCM/methanol 9:1. The filtrate was concentrated in vacuo and then extracted with DCM and saturated aqueous sodium hydrogen carbonate solution, dried over a silicone filter and concentrated in vacuo. to give 1.95 g (5.42 mmol, 84%) of analytically pure target compound.

$^1$H-NMR (400 MHz, DMSO-$d_6$): δ [ppm]=1.27 (t, 3H), 2.06 (s, 3H), 3.88 (s, 3H), 4.02 (q, 2H), 5.16 (s, 2H), 6.69-6.75 (m, 2H), 8.79-9.05 (m, 4H).

The following intermediates were prepared according to the same procedure:

| | | | |
|---|---|---|---|
| 1-3-2 | 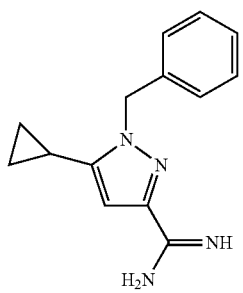 [SMILES: N=C(N)c1cc(C2CC2)n(Cc2ccccc2)n1] | 1-benzyl-5-cyclopropyl-1H-pyrazole-3-carboximidamide hydrochloride 1:1 | $^1$H-NMR (400 MHz, DMSO-$d_6$): δ [ppm] = 0.45-0.60 (m, 2H), 0.88-0.98 (m, 2H), 1.87-1.98 (m, 1H), 5.53 (s, 2H), 6.84 (s, 1H), 7.04-7.44 (m, 5H), 8.98 (br. s., 2H), 9.17 (br. s., 1H). |
| 1-3-3 | 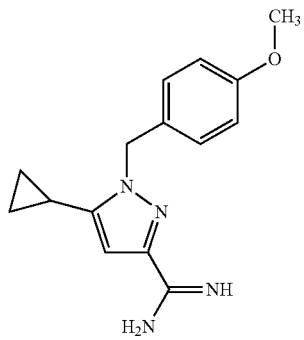 [SMILES: COc1ccc(Cn2nc(C(=N)N)cc2C2CC2)cc1] | 5-cyclopropyl-1-(4-methoxybenzyl)-1H-pyrazole-3-carboximidamide hydrochloride 1:1 | $^1$H-NMR (400 MHz, DMSO-$d_6$): δ [ppm] = 0.48-0.57 (m, 2H), 0.91-0.98 (m, 2H), 1.88-1.97 (m, 1H), 3.67-3.72 (m, 3H), 5.43 (s, 2H), 6.77 (s, 1H), 6.88 (d, 2H), 7.16 (d, 2H), 8.78-8.96 (m, 2H), 9.07-9.17 (m, 1H). |
| 1-3-4 | 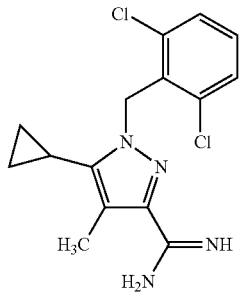 [SMILES: Cc1c(C(=N)N)nn(Cc2c(Cl)cccc2Cl)c1C1CC1] | 5-cyclopropyl-1-(2,6-dichlorobenzyl)-4-methyl-1H-pyrazole-3-carboximidamide | $^1$H-NMR (300 MHz, DMSO-$d_6$): δ [ppm] = 0.68-0.76 (m, 2H), 1.02-1.11 (m, 2H), 1.84 (m, 1H), 2.12 (s, 3H), 5.61 (s, 2H), 7.37-7.44 (m, 1H), 7.47-7.53 (m, 2H), 8.65 (br. s., 1H), 8.93 (br. s., 2H). |

| | | | |
|---|---|---|---|
| 1-3-5 | 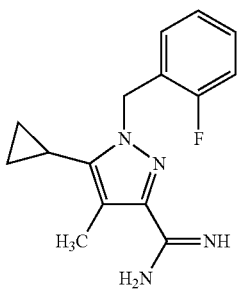 [SMILES: Cc1c(C(=N)N)nn(Cc2ccccc2F)c1C1CC1] | 5-cyclopropyl-1-(2-fluoro-benzyl)-4-methyl-1H-pyrazole-3-carboximidamide | $^1$H-NMR (300 MHz, DMSO-$d_6$): δ [ppm] = 0.53-0.62 (m, 2H), 0.92-1.01 (m, 2H), 1.59 (m, 1H), 2.12 (s, 3H), 5.51 (s, 2H), 7.02-7.41 (m, 4H), 8.90 (d, 3H). |
| 1-3-6 | 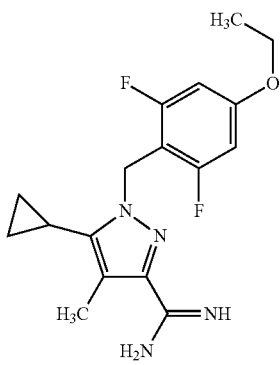 [SMILES: CCOc1cc(F)c(Cn2nc(C(=N)N)c(C)c2C2CC2)c(F)c1] | 5-cyclopropyl-1-(4-ethoxy-2,6-difluorobenzyl)-4-methyl-1H-pyrazole-3-carboximidamide hydrochloride 1:1 | $^1$H-NMR (400 MHz, DMSO-$d_6$): δ [ppm] = 0.60-0.72 (m, 2H), 1.00-1.08 (m, 2H), 1.28 (t, 3H), 1.68 (m, 1H), 2.08-2.12 (s, 3H), 4.02 (q, 2H), 5.39 (s, 2H), 6.68-6.76 (m, 2H), 8.40-9.15 (m, 3H). |
| 1-3-7 | 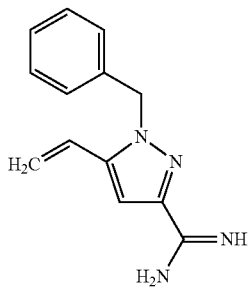 [SMILES: C=Cc1cc(C(=N)N)nn1Cc1ccccc1] | 1-benzyl-5-ethenyl-1H-pyrazole-3-carboximidamide | $^1$H-NMR (300 MHz, DMSO-$d_6$): δ [ppm] = 5.30-5.36 (m, 1H), 5.43 (s, 2H), 5.67-5.79 (m, 1H), 6.74 (dd + b. s., 4H), 6.98 (s, 1H), 7.09 (d, 2H), 7.18-7.36 (m, 3H). |
| 1-3-9 | 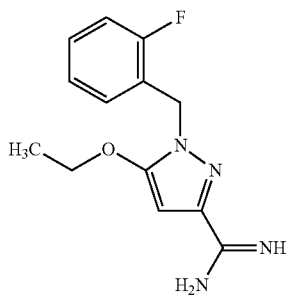 [SMILES: CCOc1cc(C(=N)N)nn1Cc1ccccc1F] | 5-ethoxy-1-(2-fluorobenzyl)-1H-pyrazole-3-carboximidamide | LC-MS: retention time: 0.76 min MS ES$^+$: 262.3 [M + H]$^+$ Method B |
| 1-3-10 | 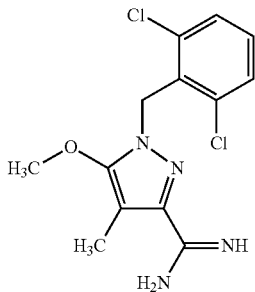 [SMILES: COc1c(C)c(C(=N)N)nn1Cc1c(Cl)cccc1Cl] | 1-(2,6-dichloro-benzyl)-5-methoxy-4-methyl-1H-pyrazole-3-carboximidamide | $^1$H-NMR (300 MHz, DMSO-$d_6$): δ [ppm] = 2.08 (s, 3H), 3.87 (s, 3H), 5.42 (s, 2H), 7.37-7.43 (m, 1H), 7.46-7.56 (m, 2H), 8.68-9.05 (m, 3H). |

| | | | |
|---|---|---|---|
| 1-3-11 | 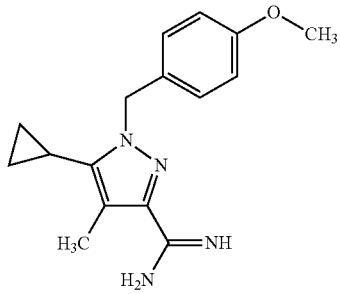 [SMILES: COc1ccc(Cn2nc(C(=N)N)c(C)c2C2CC2)cc1] | 5-cyclopropyl-1-(4-methoxybenzyl)-4-methyl-1H-pyrazole-3-carboximidamide hydrochloride 1:1 | ¹H-NMR (400 MHz, DMSO-d₆): δ [ppm] = 0.55-0-59 (m, 2H), 0.95-0.99 (m, 2H), 1.48-1.58 (m, 1H), 2.11 (s, 3H), 3.69 (s, 3H), 5.36 (s, 2H), 6.83-6.90 (m, 2H), 7.16 (d, 2H), 8.61-9.12 (m, 3H). |
| 1-3-12 | 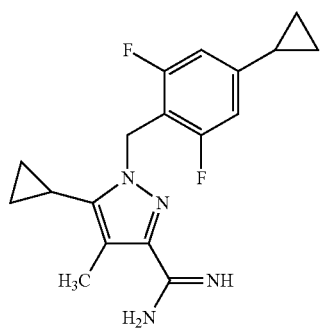 [SMILES: Cc1c(C(=N)N)nn(Cc2c(F)cc(C3CC3)cc2F)c1C1CC1] | 5-cyclopropyl-1-(4-cyclopropyl-2,6-difluorobenzyl)-4-methyl-1H-pyrazole-3-carboximidamide hydrochloride 1:1 | LC-MS: retention time: 1.01 min MS ES⁺: 331.2 [M + H]⁺ |
| 1-3-13 | 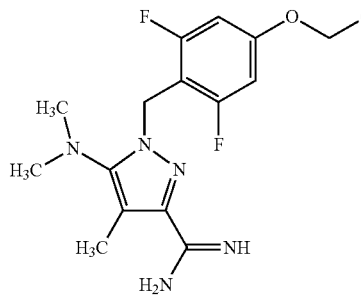 | 5-(dimethylamino)-1-(4-ethoxy-2,6-difluorobenzyl)-4-methyl-1H-pyrazole-3-carboximidamide hydrochloride 1:1 | ¹H-NMR (300 MHz, DMSO-d₆): δ [ppm] = 1.27 (t, 3H), 2.12 (s, 3H), 2.71 (s, 6H), 4.00 (q, 2H), 5.19 (s, 2H), 6.63-6.77 (m, 2H), 7.22-7.70 (m, 1H), 8.50-9.40 (m, 3H). |
| 1-3-14 | 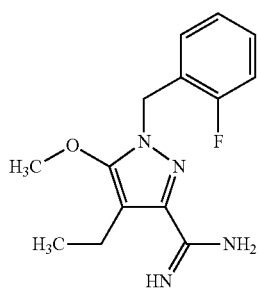 [SMILES: CCc1c(C(=N)N)nn(Cc2ccccc2F)c1OC] | 4-ethyl-1-(2-fluorobenzyl)-5-methoxy-1H-pyrazole-3-carboximidamide | |
| 1-3-15 | 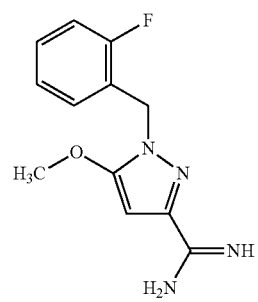 [SMILES: COc1cc(C(=N)N)nn1Cc1ccccc1F] | 1-(2-fluorobenzyl)-5-methoxy-1H-pyrazole-3-carboximidamide hydrochloride 1:1 | ¹H-NMR (300 MHz, DMSO-d₆): δ [ppm] = 3.91 (s, 3H), 5.28 (s, 2H), 6.65 (s, 1H), 7.04-7.40 (m, 4H), 8.88-9.27 (m, 3H). LC-MS (Method 2): retention time: 0.71 min MS ES⁺: 248.0 [M + H]⁺ |

Alternative Preparation of Amidines (Intermediate 1-3-8)

Intermediate 1-3-8

Preparation of 5-(dimethylamino)-1-(2-fluorobenzyl)-1H-pyrazole-3-carboximidamide hydrochloride 1:1

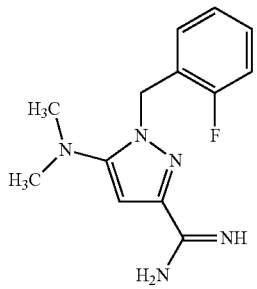 [SMILES: CN(C)c1cc(C(=N)N)nn1Cc1ccccc1F]

356 mg of sodium methanolate (6.60 mmol, 4.0 eq.) were dissolved in 10 mL of methanol. 403 mg of 5-(dimethylamino)-1-(2-fluorobenzyl)-1H-pyrazole-3-carbonitrile 1-11-1 (1.65 mmol, 1.0 eq.) were dissolved in 20 mL of methanol and added dropwise. The mixture was stirred for one hour at rt. 111.2 mg of ammonium chloride (2.08 mmol, 1.26 eq.) and 377 μL of 100% acetic acid (6.60 mmol, 4.0 eq.) were added and stirred under reflux for 24 hours. 111 mg of ammonium chloride (2.08 mmol, 1.26 eq.) and 377 μL of 100% acetic acid (6.60 mmol, 4.0 eq.) were added and stirred under reflux for 24 hours again. The mixture was concentrated under vacuo. The residue was suspended in acetonitrile and filtered off two times. The filter cakes were dissolved in DCM/methanol 1:1 and filtered over a silica column to provide 313 mg (1.19 mmol, 72.6%) of analytically pure target compound.

$^1$H-NMR (400 MHz, DMSO-$d_6$): δ [ppm]=2.59 (s, 6H), 5.34 (s, 2H), 6.70 (s, 1H), 6.97-7.04 (m, 1H), 7.14 (s, 2H), 7.29-7.39 (m, 1H), 8.72-10.63 (m, 3H).

Intermediate 1-4-1

Preparation of 3,3-bis(dimethylamino)-2-methoxypropanenitrile

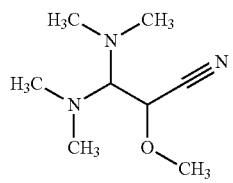

360 g of 1-tert-butoxy-N,N,N',N'-tetramethylmethanediamine (Bredereck's reagent) (2068 mmol, 1.0 eq.) and 150.0 g of methoxyacetonitrile (2068 mmol, 1.0 eq.) were stirred for 18 hours at 80° C. The reaction mixture was concentrated in vacuo. The residue was purified by vacuum distillation to yield 117 g (687 mmol, 33.0%) of the analytical pure target compound as a yellowish liquid.

$^1$H-NMR (400 MHz, DMSO-$d_6$): δ [ppm]=2.23 (s, 6H), 2.29 (s, 6H), 3.23 (d, 1H), 3.36-3.41 (s, 3H), 4.73 (d, 1H).

Intermediate 1-5-1

Preparation of 2-[1-(4-ethoxy-2,6-difluorobenzyl)-5-methoxy-4-methyl-1H-pyrazol-3-yl]-5-methoxypyrimidin-4-amine

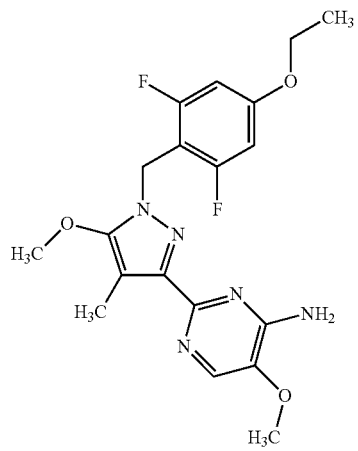 [SMILES: CCOc1cc(F)c(Cn2nc(-c3ncc(OC)c(N)n3)c(C)c2OC)c(F)c1]

1.95 g of 1-(4-ethoxy-2,6-difluorobenzyl)-5-methoxy-4-methyl-1H-pyrazole-3-carboximidamide hydrochloride 1:1 1-3-1 (5.42 mmol, 1.0 eq) were suspended in 19.7 mL of dry 3-methyl-1 butanol. 0.3 mL of piperidine (3.0 mmol, 0.56 eq) and 3.09 g of 3,3-bis(dimethylamino)-2-methoxypropanenitrile 1-4-1 (18.0 mmol, 3.30 eq) were added under nitrogen atmosphere and stirred for 24 hours at 100° C. bath temperature. The reaction mixture cooled to rt was concentrated in vacuo and purified by flash chromatography to give 619 mg (1.13 mmol, 21%) of analytically pure target compound.

$^1$H-NMR (300 MHz, DMSO-$d_6$): δ [ppm]=1.27 (t, 3H), 2.15 (s, 3H), 3.79 (s, 3H), 3.83 (s, 3H), 4.01 (q, 2H), 5.05 (s, 2H), 6.62-6.74 (m, 4H), 7.81 (s, 1H).

The following intermediates were prepared according to the same procedure using amidines and Intermediate 1-4-1:

| | | | |
|---|---|---|---|
| 1-5-2 | 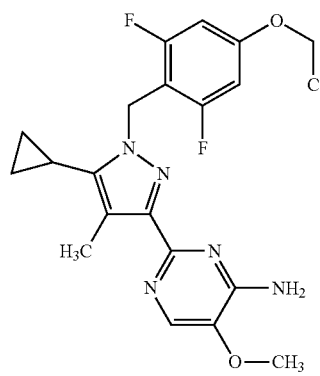 | 2-[5-cyclopropyl-1-(4-ethoxy-2,6-difluorobenzyl)-4-methyl-1H-pyrazol-3-yl]-5-methoxypyrimidin-4-amine | $^1$H-NMR (300 MHz, DMSO-$d_6$): δ [ppm] = 0.63-0.68 (m, 2H), 0.92-1.07 (m, 2H), 1.27 (t, 3H), 1.55-1.73 (m, 1H), 2.18 (s, 3H), 3.78 (s, 3H), 4.01 (q, 2H), 5.28 (s, 2H), 6.54-6.74 (m, 4H), 7.80 (s, 1H). |

| | | | |
|---|---|---|---|
| 1-5-3 | 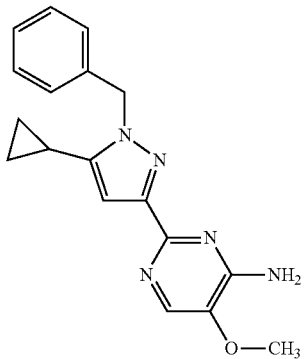 [SMILES: COc1cnc(-c2cc(C3CC3)n(Cc3ccccc3)n2)nc1N] | 2-(1-benzyl-5-cyclopropyl-1H-pyrazol-3-yl)-5-methoxypyrimidin-4-amine | $^1$H-NMR (300 MHz, DMSO-d$_6$): δ [ppm] = 0.50-0.62 (m, 2H), 0.81-0.93 (m, 2H), 1.82 (s, 1H), 3.79 (s, 3H), 5.39 (s, 2H), 6.31 (s, 1H), 6.66 (br. s., 2H), 7.14 (d, 2H), 7.19-7.38 (m, 3H), 7.77 (s, 1H). |
| 1-5-4 | 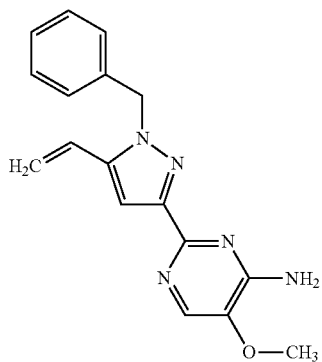 [SMILES: C=Cc1cc(-c2ncc(OC)c(N)n2)nn1Cc1ccccc1] | 2-(1-benzyl-5-ethenyl-1H-pyrazol-3-yl)-5-methoxy-pyrimidin-4-amine | $^1$H-NMR (300 MHz, DMSO-d$_6$): δ [ppm] = 3.81 (s, 3H), 5.22-5.35 (m, 1H), 5.43 (s, 2H), 5.78 (dd, 1H), 6.61-6.86 (m, 3H), 6.97 (s, 1H), 7.05-7.15 (m, 2H), 7.18-7.35 (m, 3H), 7.81 (s, 1H). |
| 1-5-5 | 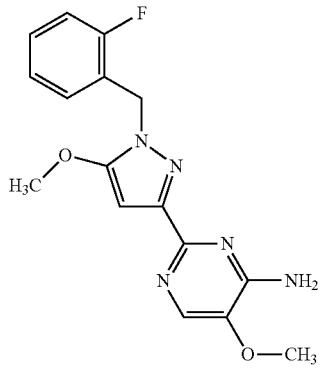 [SMILES: COc1cnc(-c2cc(OC)n(Cc3ccccc3F)n2)nc1N] | 2-[1-(2-fluoro-benzyl)-5-methoxy-1H-pyrazol-3-yl]-5-methoxypyrimidin-4-amine | $^1$H-NMR (400 MHz, DMSO-d$_6$): δ [ppm] = 3.80 (s, 3H), 3.88 (s, 3H), 5.15 (s, 2H), 6.13 (s, 1H), 6.56-6.77 (s, 2H), 7.03 (d, 1H), 7.09-7.22 (m, 2H), 7.30 (s, 1H), 7.79 (s, 1H). |
| 1-5-6 | 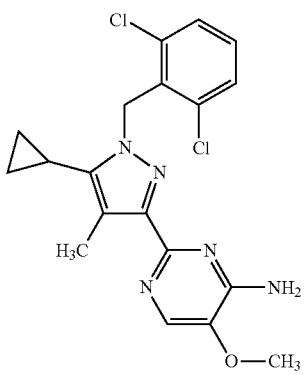 [SMILES: COc1cnc(-c2nn(Cc3c(Cl)cccc3Cl)c(C3CC3)c2C)nc1N] | 2-[5-cyclopropyl-1-(2,6-dichlorobenzyl)-4-methyl-1H-pyrazol-3-yl]-5-methoxypyrimidin-4-amine | $^1$H-NMR (400 MHz, DMSO-d$_6$): δ [ppm] = 0.67-0.74 (m, 2H), 0.97-1.04 (m, 2H), 1.78 (m, 1H), 2.19 (s, 3H), 3.76 (s, 3H), 5.52 (s, 2H), 6.50-6.65 (b. s, 2H), 7.35-7.41 (m, 1H), 7.47-7.51 (m, 2H), 7.78 (s, 1H). |

| | | | |
|---|---|---|---|
| 1-5-7 | 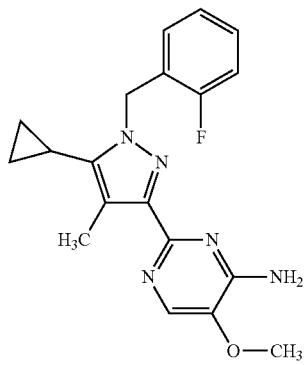 [SMILES: COc1cnc(-c2nn(Cc3ccccc3F)c(C3CC3)c2C)nc1N] | 2-[5-cyclopropyl-1-(2-fluorobenzyl)-4-methyl-1H-pyrazol-3-yl]-5-methoxypyrimidin-4-amine | $^1$H-NMR (300 MHz, DMSO-$d_6$): δ [ppm] = 0.56 (m, 2H), 0.89 (m, 2H), 1.46-1.62 (m, 1H), 2.24 (s, 3H), 3.79 (s, 3H), 5.41 (s, 2H), 6.52-6.73 (s, 2H), 6.85 (t, 1H), 7.11 (t, 1H), 7.15-7.23 (m, 1H), 7.25-7.34 (m, 1H), 7.83 (s, 1H). |
| 1-5-8 | 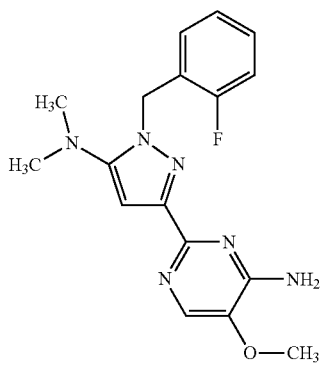 [SMILES: COc1cnc(-c2cc(N(C)C)n(Cc3ccccc3F)n2)nc1N] | 2-[5-(dimethylamino)-1-(2-fluorobenzyl)-1H-pyrazol-3-yl]-5-methoxypyrimidin-4-amine | LC-MS: retention time: 0.81 min MS ES$^+$: 343.0 [M + H]$^+$ Method B |
| 1-5-9 | 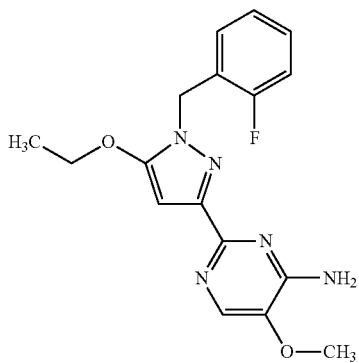 [SMILES: CCOc1cc(-c2ncc(OC)c(N)n2)nn1Cc1ccccc1F] | 2-[5-ethoxy-1-(2-fluorobenzyl)-1H-pyrazol-3-yl]-5-methoxypyrimidin-4-amine | $^1$H-NMR (400 MHz, DMSO-$d_6$): δ [ppm] = 1.28 (t, 3H), 3.79 (s, 3H), 4.14 (q, 2H), 5.14 (s, 2H), 6.10 (s, 1H), 6.57 (br. s, 1H), 6.99-7.09 (m, 1H), 7.09-7.22 (m, 3H), 7.27-7.38 (m, 1H), 7.78 (s, 1H). |
| 1-5-10 | 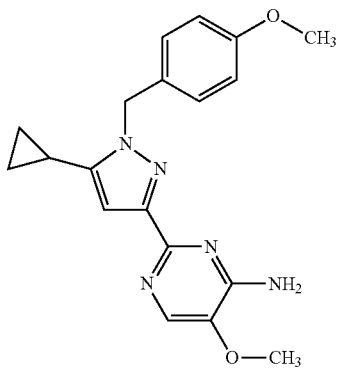 [SMILES: COc1ccc(Cn2nc(-c3ncc(OC)c(N)n3)cc2C2CC2)cc1] | 2-[5-cyclopropyl-1-(4-methoxybenzyl)-1H-pyrazol-3-yl]-5-methoxypyrimidin-4-amine | $^1$H-NMR (300 MHz, DMSO-$d_6$): δ [ppm] = 0.44-0.62 (m, 2H), 0.83-0-90 (m, 2H), 1.74-1.90 (m, 1H), 3.68 (s, 3H), 3.79 (s, 3H), 5.31 (s, 2H), 6.28 (s, 1H), 6.54-6.74 (m, 2H), 6.86 (d, 2H), 7.11 (d, 2H), 7.77 (s, 1H). |

| | | | |
|---|---|---|---|
| 1-5-11 | 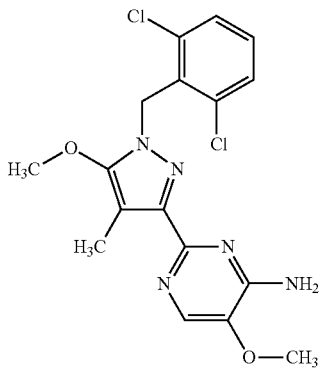 [SMILES: COc1cnc(-c2nn(Cc3c(Cl)cccc3Cl)c(OC)c2C)nc1N] | 2-[1-(2,6-di-chlorobenzyl)-5-methoxy-4-methyl-1H-pyrazol-3-yl]-5-methoxypyrimidin-4-amine | $^1$H-NMR (300 MHz, DMSO-d$_6$): δ [ppm] = 2.25 (s, 3H), 3.94 (s, 3H), 3.96 (s, 3H), 5.38 (s, 2H), 7.35-7.44 (m, 1H), 7.52 (d, 2H), 8.03-8.11 (m, 2H), 8.19 (s, 1H), 8.26-8.34 (m, 2H), 9.22 (s, 1H). |
| 1-5-12 | 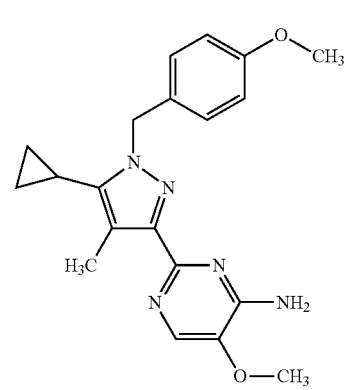 [SMILES: COc1ccc(Cn2nc(-c3ncc(OC)c(N)n3)c(C)c2C2CC2)cc1] | 2-[5-cyclopropyl-1-(4-methoxybenzyl)-4-methyl-1H-pyrazol-3-yl]-5-methoxypyrimidin-4-amine | $^1$H-NMR (300 MHz, DMSO-d$_6$): δ [ppm] = 0.53-0.58 (m, 2H), 0.86-0.93 (m, 2H), 1.39-1.56 (m, 1H), 2.22 (s, 3H), 3.68 (s, 3H), 3.79 (s, 3H), 5.27 (s, 2H), 6.63 (br. s, 2H), 6.80-6.91 (m, 2H), 7.03-7.08 (m, 2H), 7.83 (s, 1H). |
| 1-5-13 | 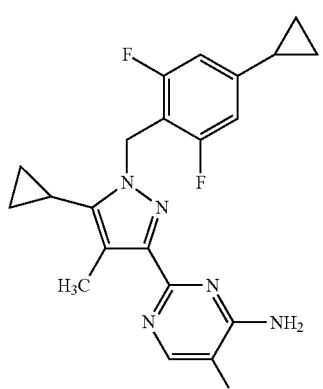 | 2-[5-cyclopropyl-1-(4-cyclopropyl-2,6-difluorobenzyl)-4-methyl-1H-pyrazol-3-yl]-5-methoxypyrimidin-4-amine | $^1$H-NMR (300 MHz, DMSO-d$_6$): δ [ppm] = 0.68 (dd, 4H), 0.86-1.05 (m, 4H), 1.57-1.67 (m, 1H), 1.88-1.98 (m, 1H), 2.18 (s, 3H), 3.77 (s, 3H), 5.31 (s, 2H), 6.61 (br. s., 2H), 6.81 (d, 2H), 7.80 (s, 1H). |
| 1-5-14 | 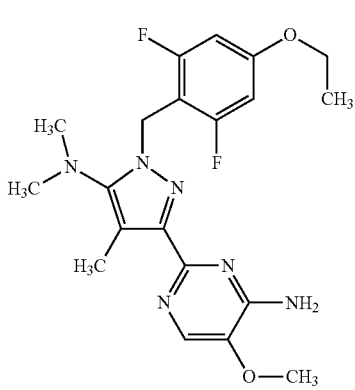 [SMILES: CCOc1cc(F)c(Cn2nc(-c3ncc(OC)c(N)n3)c(C)c2N(C)C)c(F)c1] | 2-[5-(dimethylamino)-1-(4-ethoxy-2,6-difluorobenzyl)-4-methyl-1H-pyrazol-3-yl]-5-methoxypyrimidin-4-amin | $^1$H-NMR (300 MHz, DMSO-d$_6$): δ [ppm] = 1.27 (t, 3H), 2.21 (s, 3H), 2.71 (s, 6H), 3.78 (s, 3H), 4.00 (q, 2H), 5.10 (s, 2H), 6.49-6.63 (m, 2H), 6.62-6.74 (m, 2H), 7.80 (s, 1H). |

| | | |
|---|---|---|
| 1-5-15 | 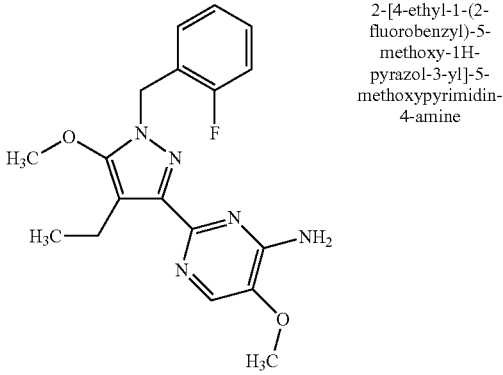 | 2-[4-ethyl-1-(2-fluorobenzyl)-5-methoxy-1H-pyrazol-3-yl]-5-methoxypyrimidin-4-amine |

Intermediate 1-6-1

Preparation of methyl 1-benzyl-5-{[(trifluoromethyl)sulfonyl]oxy}-1H-pyrazole-3-carboxylate

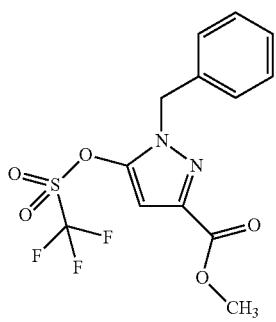 [SMILES: COC(=O)c1cc(OS(=O)(=O)C(F)(F)F)n(Cc2ccccc2)n1]

2.00 g of methyl 1-benzyl-5-hydroxy-1H-pyrazole-3-carboxylate 1-1-4 (8.61 mmol, 1.0 eq.) were suspended in 16.6 mL of dry DCM under nitrogen atmosphere. Then 1.74 mL of dry pyridine (21.5 mmol, 2.5 eq.) and 1.82 mL of trifluomethanesulfonic anhydride (10.8 mmol, 1.25 eq) were added and stirred for 3 days at rt. The reaction mixture was filtered off over a short (5 g—silica) flash column and washed with DCM. The filtrate was concentrated in vacuo. The residue was concentrated once with toluene and purified by flash chromatography to provide 2.77 g (6.84 mmol, 79%) of analytically pure target compound.

$^1$H-NMR (400 MHz, DMSO-d$_6$): δ [ppm]=3.79 (s, 3H), 5.43 (s, 2H), 6.87 (s, 1H), 7.16-7.21 (m, 2H), 7.27-7.40 (m, 3H).

Intermediate 1-7-1

Preparation of methyl 1-benzyl-5-cyclopropyl-1H-pyrazole-3-carboxylate

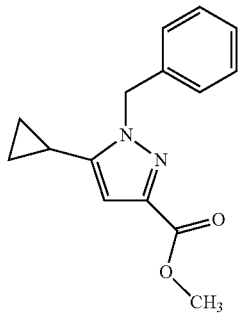 [SMILES: COC(=O)c1cc(C2CC2)n(Cc2ccccc2)n1]

2.57 g of methyl 1-benzyl-5-{[(trifluoromethyl)sulfonyl]oxy}-1H-pyrazole-3-carboxylate (7.06 mmol, 1.0 eq.) were dissolved in 51 mL of dry 1,2-dimethoxyethane under nitrogen atmosphere. 1.52 g of cyclopropylboronic acid (17.6 mmol, 2.5 eq.), 2.62 g of sodium carbonate (24.7 mmol, 3.5 eq.) and 408 mg of tetrakis(triphenylphosphin) palladium(0) (0.353 mmol, 0.05 eq.) were added and the mixture was stirred for 24 hours at 75° C. bath temperature. Then the mixture was filtered off and washed with ethyl acetate. The filtrate was concentrated in vacuo and the residue purified by flash chromatography to give 1.61 g (5.39 mmol, 76%) of analytically pure target compound.

$^1$H-NMR (400 MHz, DMSO-d$_6$): δ [ppm]=0.59 (dd, 2H), 0.83-0.89 (m, 2H), 1.85 (s, 1H), 3.72 (s, 3H), 5.46 (s, 2H), 6.40 (d, 1H), 7.11-7.16 (m, 2H), 7.22-7.35 (m, 3H).

The following intermediates were prepared according to the same procedures as described for the syntheses of intermediates 1-6-1 and 1-7-1:

| | | | |
|---|---|---|---|
| 1-7-2 | 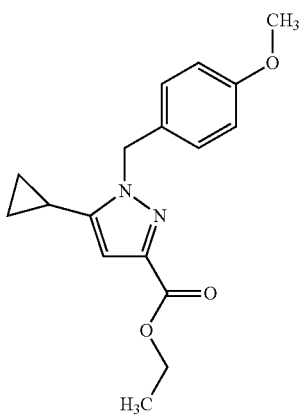 [SMILES: CCOC(=O)c1cc(C2CC2)n(Cc2ccc(OC)cc2)n1] | ethyl 5-cyclopropyl-1-(4-methoxybenzyl)-1H-pyrazole-3-carboxylate | ¹H-NMR (300 MHz, DMSO-d₆): δ [ppm] = 0.58 (m, 2H), 0.79-0.93 (m, 2H), 1.17-1.30 (t, 3H), 1.85 (s, 1H), 3.69 (s, 3H), 4.10-4.26 (q, 2H), 5.37 (s, 2H), 6.35 (s, 1H), 6.82-6.93 (m, 2H), 7.11 (d, 2H). |
| 1-7-3 | 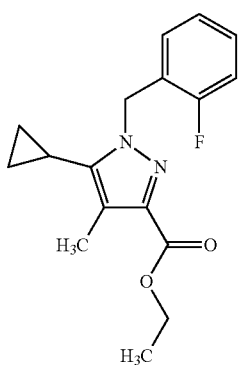 [SMILES: CCOC(=O)c1nn(Cc2ccccc2F)c(C2CC2)c1C] | ethyl 5-cyclopropyl-1-(2-fluorobenzyl)-4-methyl-1H-pyrazole-3-carboxylate | ¹H-NMR (400 MHz, DMSO-d₆): δ [ppm] = 0.53-0.60 (m, 2H), 0.88-0.94 (m, 2H), 1.23 (t, 3H), 1.54 (m, 1H), 2.16 (s, 3H), 4.19 (q, 2H), 5.47 (s, 2H), 6.86-6.94 (m, 1H), 7.13 (td, 1H), 7.17-7.24 (m, 1H), 7.33 (d, 1H). |
| 1-7-4 | 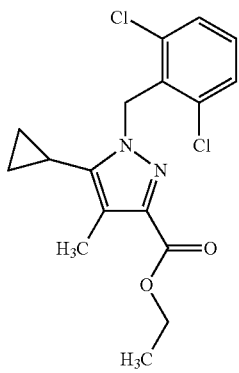 [SMILES: CCOC(=O)c1nn(Cc2c(Cl)cccc2Cl)c(C2CC2)c1C] | ethyl 5-cyclopropyl-1-(2,6-dichlorobenzyl)-4-methyl-1H-pyrazole-3-carboxylate | ¹H-NMR (400 MHz, DMSO-d₆): δ [ppm] = 0.67-0.75 (m, 2H), 0.97-1.05 (m, 2H), 1.17 (t, 3H), 1.78 (m, 1H), 2.15 (s, 3H), 4.13 (q, 2H), 5.57 (s, 2H), 7.37-7.43 (t, 1H), 7.48-7.53 (m, 2H). |
| 1-7-6 | 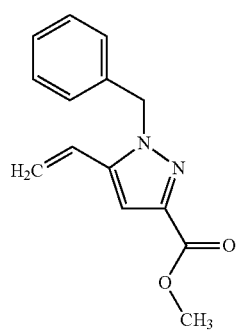 [SMILES: C=Cc1cc(C(=O)OC)nn1Cc1ccccc1] | methyl 1-benzyl-5-ethenyl-1H-pyrazole-3-carboxylate | ¹H-NMR (400 MHz, DMSO-d₆): δ [ppm] = 3.76 (s, 3H), 3.90 (s, 1H), 5.35-5.41 (m, 1H), 5.49 (s, 2H), 5.84-5.92 (m, 1H), 6.75-6.85 (m, 1H), 7.07-7.13 (m, 2H), 7.29 (d, 3H). |

Intermediate 1-8-1

Preparation of ethyl 5-amino-1-(2-fluorobenzyl)-1H-pyrazole-3-carboxylate

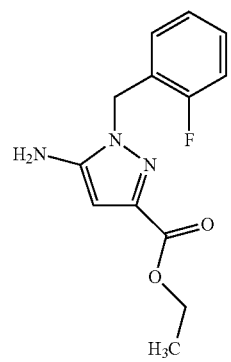 [SMILES: CCOC(=O)c1cc(N)n(Cc2ccccc2F)n1]

was conducted following the procedure depicted in Bioorg Med Chem Lett, 2001, 11/6, 781-784.

Intermediate 1-9-1

Preparation of ethyl 5-(dimethylamino)-1-(2-fluorobenzyl)-1H-pyrazole-3-carboxylate

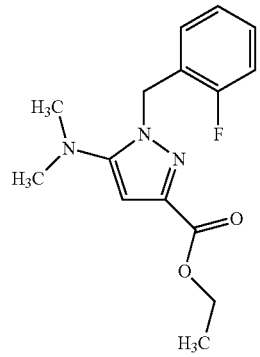 [SMILES: CCOC(=O)c1cc(N(C)C)n(Cc2ccccc2F)n1]

1.96 g of ethyl 5-amino-1-(2-fluorobenzyl)-1H-pyrazole-3-carboxylate 1-8-1 (7.46 mmol, 1.0 eq.) were dissolved in 9.8 mL of dry DMF. Under nitrogen atmosphere 237 mg of lithium hydride (29.8 mmol, 4.0 eq.) were added at 0° C. bath temperature. The mixture was stirred for one hour at this temperature. Then 3.7 mL of iodomethane (59.6 mmol, 8.0 eq.) were added at 0° C. bath temperature. The reaction mixture was stirred then for three days at rt. After the addition of ice it was stirred for 30 minutes and then extracted three times with ethyl acetate. The combined organic layers were washed with brine, dried over sodium sulfate and concentrated in vacuo. The residue was purified by flash chromatography to provided 1.35 g (4.49 mmol, 60%) of analytically pure target compound.

$^1$H-NMR (400 MHz, DMSO-d$_6$): δ [ppm]=1.22 (t, 3H), 2.57 (s, 6H), 4.19 (d, 2H), 5.30 (s, 2H), 6.40 (s, 1H), 6.91-6.99 (m, 1H), 7.10-7.23 (m, 2H), 7.28-7.37 (m, 1H).

The following intermediate was prepared according to the same procedure, using intermediate 1-20-1:

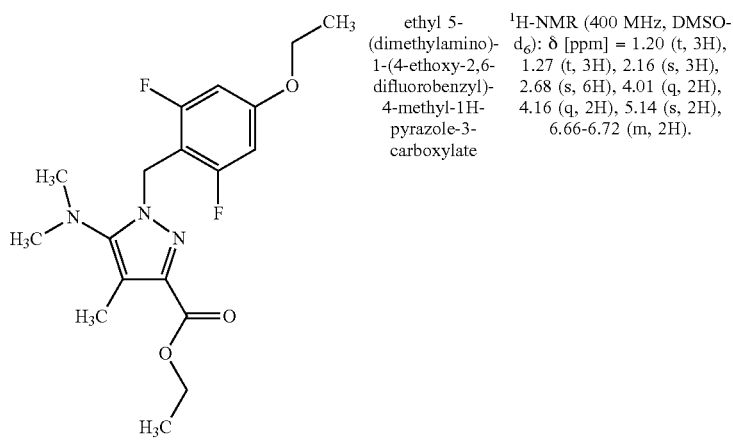

| | | |
|---|---|---|
| 1-9-2 | ethyl 5-(dimethylamino)-1-(4-ethoxy-2,6-difluorobenzyl)-4-methyl-1H-pyrazole-3-carboxylate | $^1$H-NMR (400 MHz, DMSO-d$_6$): δ [ppm] = 1.20 (t, 3H), 1.27 (t, 3H), 2.16 (s, 3H), 2.68 (s, 6H), 4.01 (q, 2H), 4.16 (q, 2H), 5.14 (s, 2H), 6.66-6.72 (m, 2H). |

Intermediate 1-10-1

Preparation of 5-(dimethylamino)-1-(2-fluorobenzyl)-1H-pyrazole-3-carboxamide

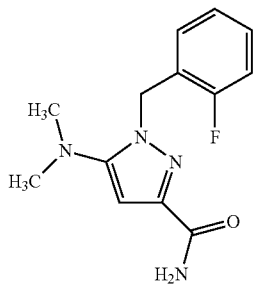 [SMILES: CN(C)c1cc(C(N)=O)nn1Cc1ccccc1F]

1.34 g of ethyl 5-(dimethylamino)-1-(2-fluorobenzyl)-1H-pyrazole-3-carboxylate 1-9-1 (4.60 mmol, 1.0 eq.) were dissolved in 120 mL of methanol. 60 mL of a 7 N solution of ammonia in methanol were added and the solution was stirred for three day at 50° C. bath temperature. 60 mL of a 7 N solution of ammonia in methanol were added again and stirred for further 24 hours at 50° C. bath temperature. 60 mL of a 7 N solution of ammonia in methanol were added again stirred for 24 hour at 65° C. bath temperature. The solution was concentrated in vacuo to provide 1.33 g (5.07 mmol, quantitative) of analytically pure target compound.

$^1$H-NMR (300 MHz, DMSO-$d_6$): δ [ppm]=2.56 (s, 6H), 5.26 (s, 2H), 6.30 (s, 1H), 6.88-6.98 (m, 1H), 7.13 (d, 3H), 7.27-7.40 (m, 2H).

Intermediate 1-11-1

Preparation of 5-(dimethylamino)-1-(2-fluorobenzyl)-1H-pyrazole-3-carbonitrile

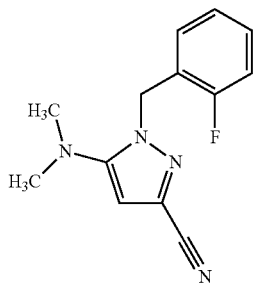 [SMILES: CN(C)c1cc(C#N)nn1Cc1ccccc1F]

1.33 g of 5-(dimethylamino)-1-(2-fluorobenzyl)-1H-pyrazole-3-carboxamide 1-10-1 (5.07 mmol, 1.0 eq.) were dissolved in 74 mL of dry THF. 1.03 mL of pyridine (12.7 mmol, 2.50 eq.) were added. Then 1.79 mL of trifluoroacetic anhydride (12.7 mmol, 2.50 eq.) were added dropwise. The reaction mixture was stirred for 24 hours at rt. Then the reaction mixture was partitioned between water and ethyl acetate. The separated aqueous layer was extracted twice with ethyl acetate. The combined organic layers were dried over sodium sulfate and concentrated in vacuo. The residue was purified by flash chromatography (hexane/ethyl acetate) to provide 406 mg (1.66 mmol, 33%) of analytically pure target compound.

$^1$H-NMR (300 MHz, DMSO-$d_6$): δ [ppm]=2.60 (s, 6H), 5.31 (s, 2H), 6.63 (s, 1H), 7.03-7.11 (m, 1H), 7.16 (s, 2H), 7.29-7.41 (m, 1H).

Intermediate 1-12-1

Preparation of 1-cyclopropylpropan-1-one

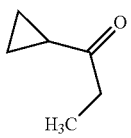

198 mL of a 3M ethylmagnesium bromide solution in diethyl ether (596 mmol, 1.0 eq.) was cooled to 0° C. and 44.2 mL of cyclopropanecarbonitrile dissolved in 80 mL of dry diethyl ether was added dropwise. The mixture was stirred at reflux for 6 hours. It was hydrolyzed with aqueous saturated ammonium chloride solution and stirred for 24 hours at rt. The resulting suspension was filtered off and washed with diethyl ether. The filtrate was dried over sodium sulfate and concentrated in vacuo (at 40° C. bath temperature and 600 mbar). The distillation in vacuo of the crude product provided 36.9 g (376 mmol, 63%) of analytically pure target compound.

$^1$H-NMR (400 MHz, DMSO-$d_6$): δ [ppm]=0.73-0.84 (m, 4H), 0.91 (t, 3H), 1.91-2.02 (m, 1H), 2.52 (q, 2H).

Intermediate 1-13-1

Preparation of ethyl 4-cyclopropyl-3-methyl-2,4-dioxobutanoate

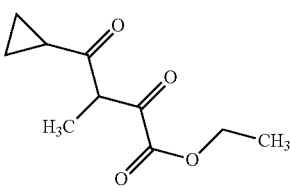

165 mL of an 1 M solution of bis(trimethylsilyl)lithiumamid in THF (166 mmol, 1.10 eq.) were brought forward in 500 mL of diethyl ether and cooled down to −78° C. 14.8 g of 1-cyclopropylpropan-1-one 1-12-1 was dissolved in 100 mL of diethyl ether and added dropwise at −78° C. The mixture was stirred for one hour at −78° C. and then 24.5 mL of diethyl oxalate was added dropwise. The cooling bath was removed and the mixture was stirred for 24 hours at rt. 500 mL of aqueous 1M hydrogen chloride solution was added and the mixture was extracted with DCM, dried over a silicone filter sulfate and concentrated in vacuo to provide 27.2 g (137 mmol, 91%) of the target compound as crude product. The crude product was used for the following step without further purification.

LC-MS:

retention time: 0.98 min

MS ES$^+$: 199.2 [M+H]$^+$

Intermediate 1-14-1

Preparation of 1-tert-butyl 3-ethyl 5-cyclopropyl-4-methyl-1H-pyrazole-1,3-dicarboxylate/1-tert-butyl 5-ethyl 3-cyclopropyl-4-methyl-1H-pyrazole-1,5-dicarboxylate

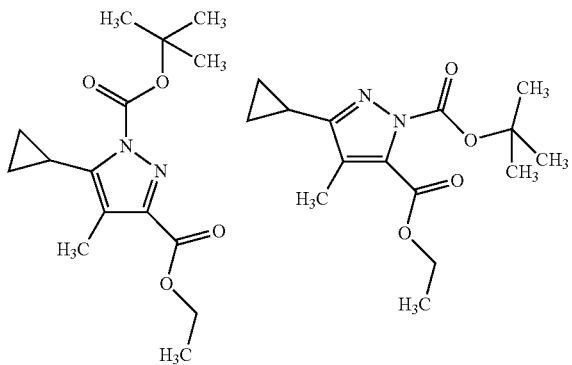 [SMILES: CCOC(=O)c1nn(C(=O)OC(C)(C)C)c(C2CC2)c1C ; CCOC(=O)c1c(C)c(C2CC2)nn1C(=O)OC(C)(C)C]

49.2 g of ethyl 4-cyclopropyl-3-methyl-2,4-dioxobutanoate 1-13-1 (248 mmol, 1.0 eq.) and 32.81 g of tert-butyl carbazate were refluxed for 4 hours in 200 mL of ethanol. The mixture was concentrated in vacuo. The residue was purified by flash chromatography to provided 2.17 g (7.37 mmol, 3.0%) of analytically pure target compound and 69.6 g (236 mmol, 95%) of a mixture of regioisomers which was used for the following step without further purification.

$^1$H-NMR (300 MHz, DMSO-d$_6$): δ [ppm]=0.71-0.81 (m, 2H), 0.82-0.93 (m, 2H), 1.24 (q, 3H), 1.46 (s, 9H), 1.73-1.89 (m, 1H), 2.04 (s, 3H), 4.25 (dd, 2H).

Intermediate 1-15-1

Preparation of ethyl 5-cyclopropyl-4-methyl-1H-pyrazole-3-carboxylate

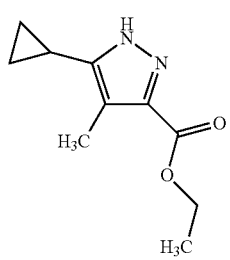

Step 1: Preparation of the hydrochloride 19.9 g of a mixture of 1-tert-butyl 3-ethyl 5-cyclopropyl-4-methyl-1H-pyrazole-1,3-dicarboxylate/1-tert-butyl 5-ethyl 3-cyclopropyl-4-methyl-1H-pyrazole-1,5-dicarboxylate 1-14-1 (67.5 mmol, 1.0 eq.) was stirred with 152 mL of 4 M hydrogene chloride solution in dioxane (608 mmol, 9.0 eq.) for three days at rt. The resulting suspension was filtered off and provided 5.20 g (18.0 mmol, 27%) of analytically pure target compound.

$^1$H-NMR (300 MHz, DMSO-d$_6$): δ [ppm]=0.62-0.72 (m, 2H), 0.81-0.87 (m, 2H), 1.24 (t, 3H), 1.69-1.83 (m, 1H), 2.16 (s, 3H), 4.21 (q, 2H)

Step 2: Preparation of the free amine 22.2 g of ethyl 5-cyclopropyl-4-methyl-1H-pyrazole-3-carboxylate hydrochloride (1:1) (67.6 mmol, 1.0 eq.) was dissolved in ethyl acetate and stirred for 30 minutes with aqueous saturated sodium hydrogen carbonate at rt. The phases were separated. The organic layer was concentrated in vacuo to provide 14.1 g (65.2 mmol, 96%) of analytically pure target compound.

$^1$H-NMR (400 MHz, DMSO-d$_6$): δ [ppm]=0.69 (br. s., 2H), 0.74-0.96 (m, 2H), 1.25 (br. s., 3H), 1.68-1.84 (m, 1H), 2.09-2.25 (m, 3H), 4.11-4.35 (m, 2H), 12.62-13.20 (m, 1H)

Alternative preparation of ethyl 5-cyclopropyl-4-methyl-1H-pyrazole-3-carboxylate hydrochloride To 10.0 g of ethyl 4-cyclopropyl-3-methyl-2,4-dioxobutanoate 1-13-1 (51 mmol, 1.0 eq.) in 100 mL ethanol were added 3.16 g hydrazine hydrate (80%, 50.4 mmol, 1.0 eq.). The reaction mixture was stirred at 70° C. for 1 h under nitrogen. The solids were filtered off and the filtrate was concentrated in vacuo. The residue was dissolved in 100 mL diethyl ether and 50 mL 2 M hydrochloric acid in diethyl ether was added. After stirring for 2 hours at rt the product was filtered off and dried at 40° C. in vacuo to provide 7.40 g (32 mmol, 66%) of analytically pure target compound.

Intermediate 1-16-1

Preparation of 2-(5-cyclopropyl-4-methyl-1H-pyrazol-3-yl)-5-methoxy-N-(pyridin-4-yl)pyrimidin-4-amine

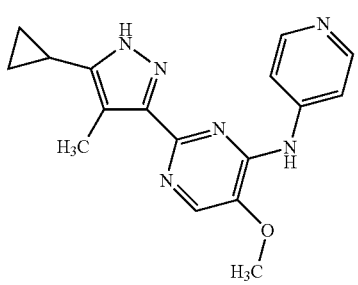 [SMILES: COc1cnc(-c2n[nH]c(C3CC3)c2C)nc1Nc1ccncc1]

410 mg of 2-[5-cyclopropyl-1-(2-fluorobenzyl)-4-methyl-1H-pyrazol-3-yl]-5-methoxy-N-(pyridin-4-yl)pyrimidin-4-amine 2-1-10 (0.952 mmol, 1.0 eq.) were dissolved in 1.1 mL of dry dimethyl sulfoxide and 1.4 mL of dry 2-methylpropan-2-ol. 6.56 mL of 1M potassium 2-methylpropan-2-olate in THF (6.56 mmol, 6.9 eq.) were added. The mixture was flushed three times with oxygen and stirred for 5 hours at rt. Then the reaction mixture was partitioned between aqueous saturated ammonium chloride solution and ethyl acetate. The separated aqueous layer was extracted three times with ethyl acetate. The combined organic layers were dried over sodium sulfate and concentrated in vacuo. The purification of the residue by flash chromatography provided 200 mg (0.62 mmol, 65.1%) of analytically pure target compound.

$^1$H-NMR (300 MHz, DMSO-$d_6$): δ[ppm]=0.60-0.91 (m, 4H), 1.69-1.90 (m, 1H), 2.33 (s, 3H), 3.97 (s, 3H), 7.96 (br. s., 2H), 8.23 (s, 1H), 8.37 (d, 2H), 9.29 (s, 1H), 12.54 (br. s., 1H).

Alternative preparation of 2-(5-cyclopropyl-4-methyl-1H-pyrazol-3-yl)-5-methoxy-N-(pyridin-4-yl)pyrimidin-4-amine 880 mg of 2-[5-cyclopropyl-1-(4-methoxybenzyl)-4-methyl-1H-pyrazol-3-yl]-5-methoxy-N-(pyridin-4-yl)pyrimidin-4-amine (2.0 mmol, 1.00 eq.) were dissolved in 7.8 mL of dry 1,2-dichloroethane. 4.6 mL trifluoroacetic acid (60 mmol, 30 eq.) and 1.8 mL trifluoromethanesulfonic acid (20 mmol, 10 eq.) were added at rt. The reaction mixture was stirred at 75° C. for 2 h. At 0° C. 2M sodiumhydroxide solution was added slowly. The solid was filtered off, dried in vacuo at 50° C. to provide 637 mg (1.96 mmol, 98%) of the analytically pure target compound.

Intermediate 1-17-1

Preparation of ethyl 5-cyclopropyl-1-(4-ethoxy-2,6-difluorobenzyl)-4-methyl-1H-pyrazole-3-carboxylate

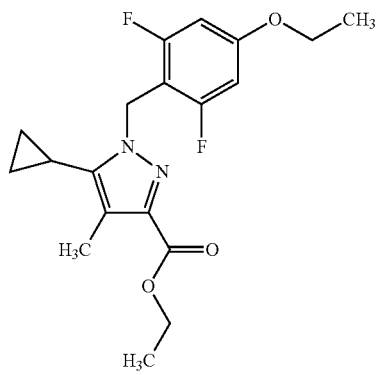 [SMILES: CCOC(=O)c1nn(Cc2c(F)cc(OCC)cc2F)c(C2CC2)c1C]

46.9 g of ethyl 5-cyclopropyl-4-methyl-1H-pyrazole-3-carboxylate 1-15-1 (266 mmol, 1.0 eq.) in 588 mL THF were cooled to 0° C. and 11.6 g sodiumhydride (60%, 290 mmol, 1.2 eq.) were added in small portions. The resulting suspension was diluted with 250 mL THF. 66.7 g 2-(bromomethyl)-5-ethoxy-1,3-difluorobenzene (266 mmol, 1.1 eq., commercially available) were added slowly. The reaction mixture was stirred at rt for 2 hours. 300 mL water was added and the THF was evaporated in vacuum. The aqueous residue was extracted with ethylacetate three times. The combined organic layers were dried over a silicone filter and concentrated in vacuo. The residue was purified by flash chromatography to provide 79.8 g (195 mmol, 81%) of 89% pure target compound.

$^1$H-NMR (400 MHz, CHLOROFORM-d): δ [ppm]=0.65-0.70 (m, 2H), 0.96-1.03 (m, 2H), 1.34-1.42 (m, 7H), 1.47-1.52 (m, 1H), 2.24 (s, 3H), 3.97 (q, 3H), 4.35 (q, 2H), 5.46 (s, 2H), 6.40-6.44 (m, 2H).

The following intermediates were prepared according to the same procedure using intermediate 1-15-1 and commercially available benzyl halides:

| | | | |
|---|---|---|---|
| 1-17-2 | 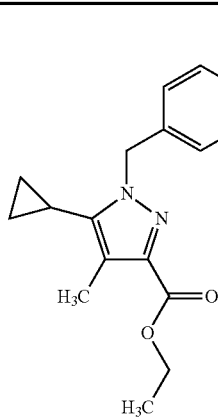 | ethyl 5-cyclopropyl-1-(4-methoxybenzyl)-4-methyl-1H-pyrazole-3-carboxylate | $^1$H-NMR (300 MHz, DMSO-$d_6$): δ [ppm] = 0.53-0.59 (m, 2H), 0.86-0.97 (m, 2H), 1.23 (t, 3H), 1.39-1.57 (m, 1H), 2.14 (s, 3H), 3.68 (s, 3H), 4.20 (q, 2H), 5.32 (s, 2H), 6.80-6.91 (m, 2H), 7.04-7.08 (m, 2H). |

| | | | |
|---|---|---|---|
| 1-17-3 | 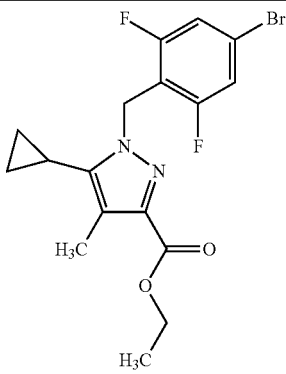 | ethyl 1-(4-bromo-2,6-difluorobenzyl)-5-cyclopropyl-4-methyl-1H-pyrazole-3-carboxylate | $^1$H-NMR (400 MHz, DMSO-$d_6$): δ [ppm] = 0.64-0.68 (m, 2H), 0.96-1.01 (m, 2H), 1.20 (t, 3H), 1.56-1.67 (m, 1H), 2.13 (s, 3H), 4.16 (q, 2H), 5.40 (s, 2H), 7.47-7.54 (m, 2H). |

Intermediate 1-19-1

Preparation of potassium (2Z)-3-cyano-1-ethoxy-1-oxobut-2-en-2-olate

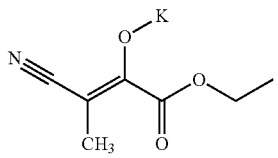

3.84 g potassium 2-methylpropan-2-olate (34.2 mmol, 1.0 eq.) and 723 mg 18-crown-6 (2.74 mmol, 0.08 eq.) were dissolved in THF and 5.00 g diethyl oxalate (34.2 mmol, 1.0 eq.) were added within 5 minutes. The reaction mixture was heated to 60° C. and 1.88 g propiononitrile (34.2 mm ol, 1.0 eq.) were added within 5 minutes. The reaction was stirred at 60° C. for 1 hour. The solid was filtered off, dried in vacuo at 50° C. to provide 5.11 g (26.4 mmol, 77%) of the crude product which was used without further purification.

$^1$H-NMR (300 MHz, DMSO-$d_6$): δ [ppm]=1.14 (t, 3H), 3.51 (s, 3H), 3.97 (q, 2H).

Intermediate 1-20-1

Preparation of ethyl 5-amino-1-(4-ethoxy-2,6-difluorobenzyl)-4-methyl-1H-pyrazole-3-carboxylate

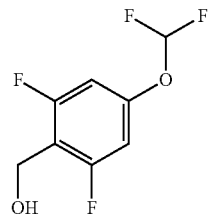 [SMILES: Fc1cc(OC(F)F)cc(F)c1CBr]

2.01 g potassium (2Z)-3-cyano-1-ethoxy-1-oxobut-2-en-2-olate (10.9 mmol, 1.0 eq.) were dissolved in dioxane at rt and 1.34 mL trifluoroacetic acid (17.4 mmol, 1.6 eq.) were added within 2 minutes. The slurry was stirred for 10 minutes and 3.00 g (4-ethoxy-2,6-difluorobenzyl)hydrazine dihydrochloride (10.9 mmol, 1.0 eq.) were added. The reaction mixture was stirred at 130° C. for 3 hours. The resulting solid was filtered off and washed rinsed with dioxane. The filtrate was partitioned between ethyl acetate and water. The aqueous phase was washed with ethyl acetate three times. The collected organic solutions were washed with brine, dried over a silicon filter, concentrated in vacuo and purified by flash chromatography: 1.10 g (2.42 mmol, 22%) of a 71% pure target compound.

$^1$H-NMR (400 MHz, DMSO-$d_6$): δ [ppm]=1.25-1.31 (m, 6H), 1.99 (s, 3H), 3.96-4.09 (m, 2H), 4.25 (q, 2H), 4.37-4.88 (m, 2H), 5.21 (s, 2H), 6.70-6.75 (m, 2H), 11.51 (s, 1H).

Intermediate 1-21-1

Preparation of [4-(difluoromethoxy)-2,6-difluorophenyl]methanol

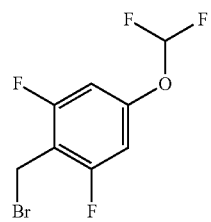

500 mg 3,5-difluoro-4-(hydroxymethyl)phenol (3.12 mmol, 1.0 eq.) were dissolved in DMF. 523 mg sodium chloro(difluoro)acetate (3.44 mmol, 1.1 eq.), 1.22 g cesium carbonate (3.75 mmo, 1.2 eq) and 0.20 mL water (10.9 mmol, 3.5 eq.) were added. The reaction mixture was stirred at 100° C. over night. The reaction mixture was divided between water and ethyl acetate. The aqueous layer was washed twice with ethyl acetate. The combined organic layers were washed with brine, dried over a silicon filter and concentrated in vacuo. The crude product was purified by flash chromatography to provide 161 mg (0.69 mmol, 22%) of the 56% pure target compound.

$^1$H-NMR (300 MHz, DMSO-$d_6$): δ [ppm]=4.42 (d, 2H), 5.23 (t, 1H), 6.92-7.04 (m, 2H), 7.30 (t, 1H).

Intermediate 1-22-1

Preparation of 2-(bromomethyl)-5-(difluoromethoxy)-1,3-difluorobenzene 162 mg [4-(difluoromethoxy)-2,6-difluorophenyl]methanol (0.769 mmol, 1.0 eq.) were dissolved in 0.348 mL hydrogen bromide (2.12 mmol, 2.8 eq.). and stirred at rt over night. The reaction mixture was diluted with diethylether and stirred for 5 minutes. The aqueous layer was washed twice with diethylether. The combined organic layers were washed with brine, dried over a silicon filter and concentrated in vacuo to provide the 149 mg (0.51 mmol, 67%) of the crude product, which was used without further purification.

$^1$H-NMR (400 MHz, DMSO-$d_6$): δ [ppm]=4.60 (s, 2H), 7.05-7.14 (m, 2H), 7.33 (t, 1H).

The following intermediate 1-22-2 was prepared according to the same procedures as described for intermediates 1-22-1 using commercially available starting materials. Intermediate 1-22-2 was used without further purification.

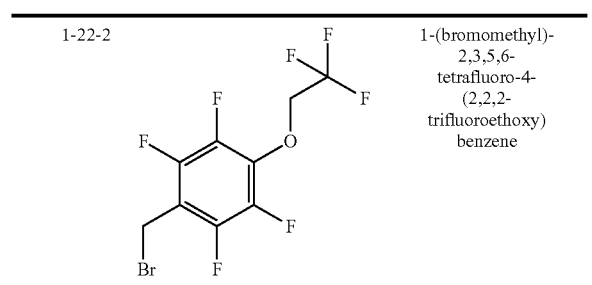

| 1-22-2 | 1-(bromomethyl)-2,3,5,6-tetrafluoro-4-(2,2,2-trifluoroethoxy)benzene |

Intermediate 1-23-1

Preparation of ethyl 5-cyclopropyl-1-(4-cyclopropyl-2,6-difluorobenzyl)-4-methyl-1H-pyrazole-3-carboxylate

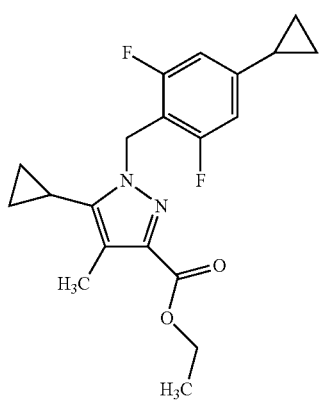 [SMILES: CCOC(=O)c1nn(Cc2c(F)cc(C3CC3)cc2F)c(C2CC2)c1C]

1.0 g ethyl 1-(4-bromo-2,6-difluorobenzyl)-5-cyclopropyl-4-methyl-1H-pyrazole-3-carboxylate (2.51 mmol, 1.0 eq.) were dissolved in 40 mL toluene and 0.280 g cyclopropylboronic acid (3.26 mmol, 1.3 eq.), 1.86 g potassium phosphate (8.77 mmol, 3.5 eq.), 70 mg tricyclohexylphosphine (0.25 mmol, 0.10 eq.) and 0.66 mL water were added. The reaction mixture was flushed with nitrogen and 28 mg palladium acetate (0.125 mmol, 0.050 eq.) were added. The reaction mixture was stirred at 100° C. over night. Again 0.280 g cyclopropylboronic acid (3.26 mmol, 1.3 eq.), 1.86 g potassium phosphate (8.77 mmol, 3.5 eq.), 70 mg tricyclohexylphosphine (0.25 mmol, 0.10 eq.) and 0.66 mL water were added. The reaction mixture was flushed with nitrogen and 28 mg palladium acetate (0.125 mmol, 0.050 eq.) were added. The reaction mixture was stirred at 100° C. over night. Water was added and the aqueous phase was washed with ethyl acetate twice. The combined organic layers were dried over a silicon filter and concentrated in vacuo. The crude product was purified by flash chromatography to provide 652 mg (1.63 mmol, 65%) of the analytically pure target compound.

$^1$H-NMR (400 MHz, DMSO-$d_6$): δ [ppm]=0.63-0.67 (m, 2H), 0.70-0-74 (m, 2H), 0.91-1.03 (m, 4H), 1.20 (t, 3H), 1.54-1.65 (m, 1H), 1.87-1.98 (m, 1H), 2.12 (s, 3H), 4.16 (q, 2H), 5.36 (s, 2H), 6.80-6.85 (m, 2H).

Intermediate 1-24-1

Preparation of 4-amino-2-[5-cyclopropyl-1-(4-ethoxy-2,6-difluorobenzyl)-4-methyl-1H-pyrazol-3-yl]pyrimidine-5-carbonitrile

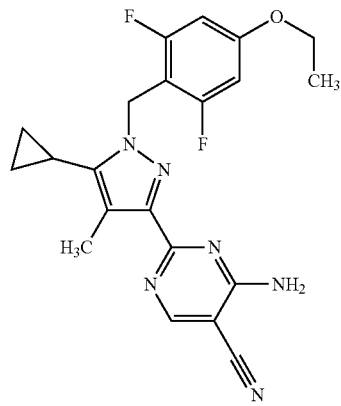 [SMILES: CCOc1cc(F)c(Cn2nc(-c3ncc(C#N)c(N)n3)c(C)c2C2CC2)c(F)c1]

146 mg of sodium methanolate (2.70 mmol, 1.0 eq) were diluted in 20 ml of methanole at room temperature under a nitrogen atmosphere. Then 1.0 g of 5-cyclopropyl-1-(4-ethoxy-2,6-difluorobenzyl)-4-methyl-1H-pyrazole-3-carboximidamide hydrochloride 1:1 1-3-6 (2.70 mmol, 1.0 eq) and 329 mg of (ethoxymethylene)malononitrile (2.70 mmol, 1.0 eq) were added and the mixture was stirred at 65° C. bath temperature for 18 hours. After cooling to rt the reaction mixture was concentrated in vacuo and purified via HPLC (ACN/H$_2$O/0.2% NH$_3$) to give 284 mg (0.65 mmol, 24%) of analytically pure target compound.

$^1$H-NMR (300 MHz, DMSO-$d_6$): δ [ppm]=0.64-0.71 (m, 2H), 0.95-1.04 (m, 2H), 1.27 (t, 3H), 1.63 (m, 1H), 2.25 (s, 3H), 4.01 (q, 2H), 5.34 (s, 2H), 6.72 (m, 2H), 7.76 (br. s., 2H), 8.56 (s, 1H).

The following intermediates were prepared according to the same procedure using starting materials which were described above:

| | | | |
|---|---|---|---|
| 1-24-2 | 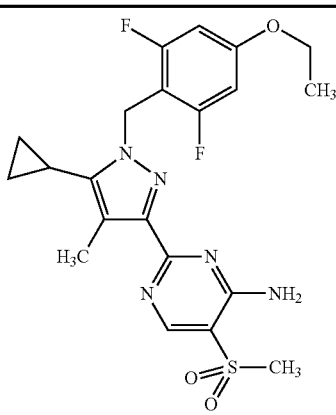 | 2-[5-cyclopropyl-1-(4-ethoxy-2,6-difluorobenzyl)-4-methyl-1H-pyrazol-3-yl]-5-(methylsulfonyl)pyrimidin-4-amine | $^1$H-NMR (300 MHz, DMSO-$d_6$): δ [ppm] = 0.68 (m, 2H), 1.00 (m, 2H), 1.27 (t, 3H), 1.63 (m, 1H), 2.27 (s, 3H), 3.20 (s, 3H), 4.01 (q, 2H), 5.35 (s, 2H), 6.72 (m, 2H), 6.62-8.28 (br. m., 2H), 8.49 (s, 1H). |
| 1-24-3 | 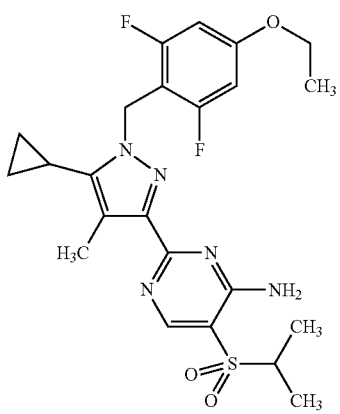 [SMILES: CCOc1cc(F)c(Cn2nc(-c3ncc(S(=O)(=O)C(C)C)c(N)n3)c(C)c2C2CC2)c(F)c1] | 2-[5-cyclopropyl-1-(4-ethoxy-2,6-difluorobenzyl)-4-methyl-1H-pyrazol-3-yl]-5-(isopropylsulfonyl)pyrimidin-4-amine | $^1$H-NMR (400 MHz, DMSO-$d_6$): δ [ppm] = 0.68 (m, 2H), 1.01 (m, 2H), 1.17 (d, 6H), 1.27 (t, 3H), 1.64 (m, 1H), 2.28 (s, 3H), 3.40 (m, 1H), 4.02 (q, 2H), 5.35 (s, 2H), 6.72 (m, 2H), 6.91 (s br, 1H), 8.08 (s br, 1H), 8.42 (s, 1H), |

Intermediate 1-25-1

Preparation of 2-[5-cyclopropyl-1-(4-ethoxy-2,6-difluorobenzyl)-4-methyl-1H-pyrazol-3-yl]pyrimidin-4-amine

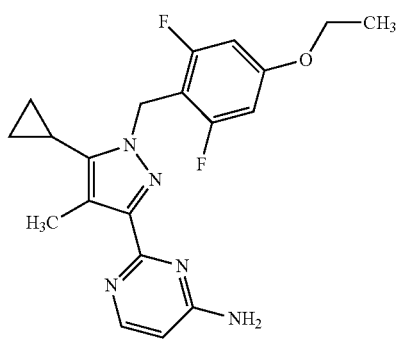 [SMILES: CCOc1cc(F)c(Cn2nc(-c3nccc(N)n3)c(C)c2C2CC2)c(F)c1]

To a suspension of 10.1 g of 5-cyclopropyl-1-(4-methoxybenzyl)-4-methyl-1H-pyrazole-3-carboximidamide hydrochloride 1:1 1-3-1 (27.2 mmol, 1.0 eq) in 163 mL of dry pyridine and 4.10 mL and 1,8-Diazabicyclo[5.4.0]undec-7-ene (27.2 mmol, 1.0 eq) 7.94 g 3-Ethoxyacrylsäurenitril (81.7 mmol, 3.30 eq) were added under nitrogen atmosphere. The reaction mixture was stirred over night at 110° C. After cooling to rt the mixture was purged into water and three times extracted with ethyl acetate. The combined organic layers were dried over Na$_2$SO$_4$ and concentrated in vacuo. The residue was taken up in DCM/MeOH 9:1 and the product was precipitated by adding diethyl ether to give 4.20 g of the desired compound 1-25-1. The mother liquor was concentrated in vacuo, the residue was suspended in ethyl acetate. The resulting precipitate was collected by filtration and washed with ethyl acetate to give additionally 1.90 g of the desired compound 1-25-1. In total 6.10 g of the target compound (15.8 mmol, 58%) were obtained.

$^1$H-NMR (300 MHz, DMSO-$d_6$): δ [ppm]=0.64-0.77 (m, 2H), 0.96-1.07 (m, 2H), 1.31 (t, 3H), 1.67 (m, 1H), 2.24 (s, 3H), 4.05 (q, 2H), 5.33 (s, 2H), 6.26 (d, 1H), 6.68-6.81 (m, 4H), 8.06 (d, 1H).

Intermediate 1-26-1

Preparation of diethyl 2-ethyl-3-oxosuccinate

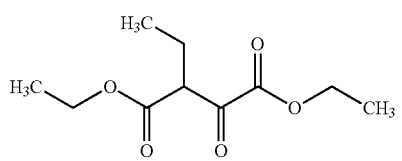

27.8 mL of lithium diisopropylamide (50.0 mmol, 1.00 eq, 1.8 M in THF/heptane/ethylbenzene) were dissolved in 50 mL of dry THF and an argon atmosphere and cooled to −75° C. 6.64 mL of ethyl butanoate (50.0 mmol, 1.00 eq) were dissolved in 25 mL of dry THF and added to the previous solution at a bath temperature of −60 to −75° C. and stirred for an additional 1 h at a bath temperature of −75° C. 6.92 mL of diethyl ethanedioate (51.0 mmol, 1.02 eq) were dissolved in 25 mL of dry THF and added to the previous solution at a bath temperature of −60 to −75° C. and stirred for an additional 30 min at a bath temperature of −75° C. The mixture was allowed to come to. −20° C., at which temperature 6.47 mL of acetic acid (113.0 mmol, 2.26 eq), followed by 100 mL of water. The mixture was then allowed to come to rt. The separated organic layer was washed, once with water, once with sodium bicarbonate solution and once with brine, before being dried over sodium sulfate and concentrated in vacuo. The crude reaction product was used for the next transformation without any further purification.

Intermediate 1-27-1

Preparation of ethyl 1-(2-fluorobenzyl)-5-methoxy-1H-pyrazole-3-carboxylate

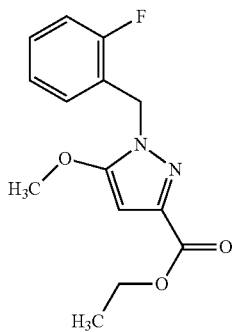 [SMILES: CCOC(=O)c1cc(OC)n(Cc2ccccc2F)n1]

21.58 g of ethyl 1-(2-fluorobenzyl)-5-hydroxy-1H-pyrazole-3-carboxylate 1-1-2 (81.66 mmol, 1.0 eq) were dissolved in dry acetone. Then 10.17 mL of iodomethane (163.3 mmol, 2.0 eq) and 40.63 g of potassium carbonate (294 mmol, 3.6 eq) were added. The precipitate was filtered off and the filtrate was concentrated in vacuo. The residue was partitioned between DCM and water, the aqueous layer was separated and extracted with DCM twice. The combined organic layers were dried over magnesium sulfate, filtered off and concentrated in vacuo to give 14.74 g (52.96 mmol, 65%) of the crude target compound that was used for the next transformation without further purification.

¹H-NMR (300 MHz, DMSO-d₆): δ [ppm]=1.23 (t, 3H), 3.88 (s, 3H), 4.20 (q, 2H), 5.21 (s, 2H), 6.19 (s, 1H), 6.99-7.38 (m, 4H).

Example Compounds

Example 2-1-1

Preparation of 2-[1-(4-ethoxy-2,6-difluorobenzyl)-5-methoxy-4-methyl-1H-pyrazol-3-yl]-5-methoxy-N-(pyridin-4-yl)pyrimidin-4-amine

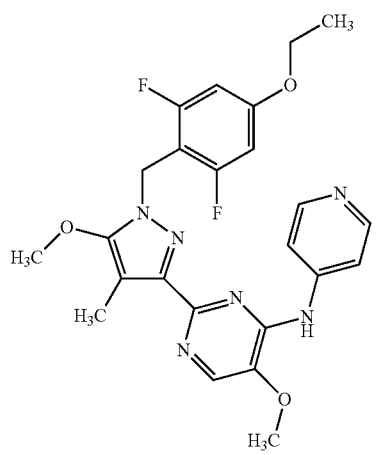 [SMILES: CCOc1cc(F)c(Cn2nc(-c3ncc(OC)c(Nc4ccncc4)n3)c(C)c2OC)c(F)c1]

619 mg of 2-[1-(4-ethoxy-2,6-difluorobenzyl)-5-methoxy-4-methyl-1H-pyrazol-3-yl]-5-methoxypyrimidin-4-amine 1-5-1 (1.53 mmol, 1.0 eq.), 445-38 mg of 4-bromopyridine hydrochloride (1:1) (2.29 mmol, 1.5 eq.), 190.15 mg of (R)-(+)-2,2'-bis(diphenylphosphino)-1,1'-binaphtyl (305 mmol, 0.2 eq.), 587 mg of sodium-tert-buylat (6.12 mmol, 4.0 eq.) and 419 mg of tris-(dibenzylideneacetone)dipalladium(0) (0.458 mmol, 0.3 eq.) were suspended in 10 mL of dry DMF and stirred under nitrogen atmosphere at 110° C. bath temperature for 24 hours. The reaction mixture was partitioned between half saturated aqueous ammonium chloride solution and DCM. The separated aqueous layer was extracted twice with DCM. The combined organic layers were washed with brine, dried over sodium sulfate and concentrated in vacuo. The residue was purified by flash chromatography (hexane (0-100%)/ethyl acetate). The column was washed with methanol to receive a 50% pure target compound. This was stirred with acetone and the suspension was filtered off.

Further purification by flash chromatography and preparative HPLC of the filter cake and the concentrated filtrate gave 82 mg (0.15 mmol, 10%) of analytically pure target compound.

¹H-NMR (300 MHz, DMSO-d₆): δ [ppm]=1.26 (t, 3H), 2.21 (s, 3H), 3.90 (s, 3H), 3.95 (s, 3H), 4.02 (q, 2H), 5.11 (s, 2H), 6.69-6.82 (m, 2H), 8.02-8.12 (m, 2H), 8.20 (s, 1H), 8.26-8.36 (m, 2H), 9.26 (s, 1H).

The following compounds were prepared according to the same procedure as described above using the starting materials logically consistent with the structure of the end product shown in the table below:

| 2-1-2 | 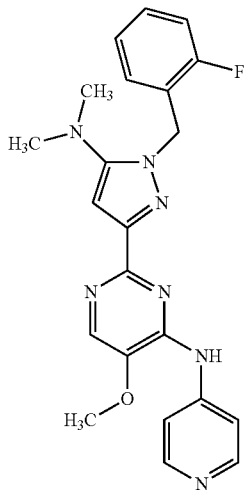 [SMILES: COc1cnc(-c2cc(N(C)C)n(Cc3ccccc3F)n2)nc1Nc1ccncc1] | 2-[5-(dimethyl-amino)-1-(2-fluorobenzyl)-1H-pyrazol-3-yl]-5-methoxy-N-(pyridin-4-yl)pyrimidin-4-amine | $^1$H-NMR (300 MHz, DMSO-$d_6$): δ [ppm] = 2.64 (s, 6H), 3.95 (s, 3H), 5.29 (s, 2H), 6.43 (s, 1H), 7.10-7.25 (m, 3H), 7.28-7.39 (m, 1H), 8.06 (d, 2H), 8.16 (s, 1H), 8.33 (d, 2H), 9.26-9.33 (m, 1H). |
|---|---|---|---|
| 2-1-3 | 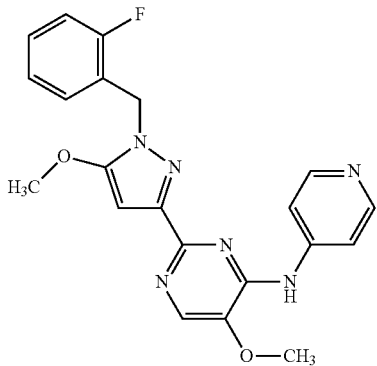 [SMILES: COc1cnc(-c2cc(OC)n(Cc3ccccc3F)n2)nc1Nc1ccncc1] | 2-[1-(2-fluoro-benzyl)-5-methoxy-1H-pyrazol-3-yl]-5-methoxy-N-(pyridin-4-yl)pyrimidin-4-amine | $^1$H-NMR (500 MHz, DMSO-$d_6$): δ [ppm] = 4.00 (d, 6H), 5.25 (s, 2H), 6.26 (s, 1H), 7.15-7.29 (m, 3H), 7.33-7.42 (m, 1H), 8.08-8.15 (m, 2H), 8.21 (s, 1H), 8.40 (d, 2H), 9.33 (s, 1H). |
| 2-1-4 | 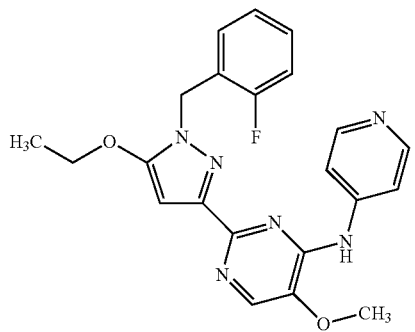 [SMILES: CCOc1cc(-c2ncc(OC)c(Nc3ccncc3)n2)nn1Cc1ccccc1F] | 2-[5-ethoxy-1-(2-fluoro-benzyl)-1H-pyrazol-3-yl]-5-methoxy-N-(pyridin-4-yl)pyrimidin-4-amine | $^1$H-NMR (300 MHz, DMSO-$d_6$): δ [ppm] = 1.32 (t, 3H), 3.96 (s, 3H), 4.20 (d, 2H), 5.20 (s, 2H), 6.19 (s, 1H), 7.18 (s, 3H), 7.29-7.39 (m, 1H), 8.08 (s, 2H), 8.16 (s, 1H), 8.34 (s, 2H), 9.27-9.32 (m, 1H). |
| 2-1-5 | 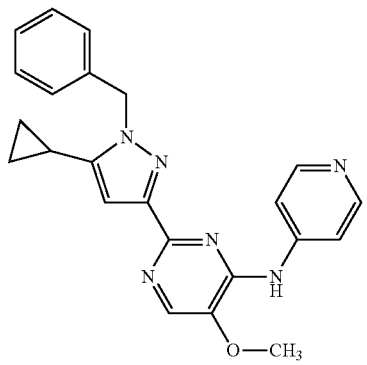 [SMILES: COc1cnc(-c2cc(C3CC3)n(Cc3ccccc3)n2)nc1Nc1ccncc1] | 2-(1-benzyl-5-cyclopropyl-1H-pyrazol-3-yl)-5-methoxy-N-(pyridin-4-yl)pyrimidin-4-amine | $^1$H-NMR (300 MHz, DMSO-$d_6$): δ [ppm] = 0.54-0.70 (m, 2H), 0.82-0.98 (m, 2H), 1.78-1.96 (m, 1H), 3.96 (s, 3H), 5.46 (s, 2H), 6.41 (s, 1H), 7.17-7.40 (m, 4H), 8.03-8.09 (m, 2H), 8.14 (d, 2H), 8.36 (d, 2H), 9.28 (s, 1H). |

| | | | |
|---|---|---|---|
| 2-1-6 | 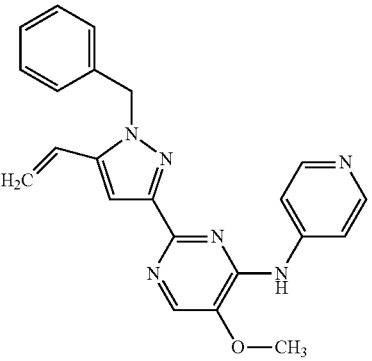 [SMILES: C=Cc1cc(-c2ncc(OC)c(Nc3ccncc3)n2)nn1Cc1ccccc1] | 2-(1-benzyl-5-ethenyl-1H-pyrazol-3-yl)-5-methoxy-N-(pyridin-4-yl)pyrimidin-4-amine | $^1$H-NMR (400 MHz, DMSO-$d_6$): δ [ppm] = 3.98 (s, 3H), 5.36 (d, 1H), 5.49 (s, 2H), 5.87 (d, 1H), 6.84 (dd, 1H), 7.07 (s, 1H), 7.18 (d, 2H), 7.22-7.36 (m, 3H), 8.06-8.12 (m, 2H), 8.20 (s, 1H), 8.38 (d, 2H), 9.32 (s, 1H). |
| 2-1-7 | 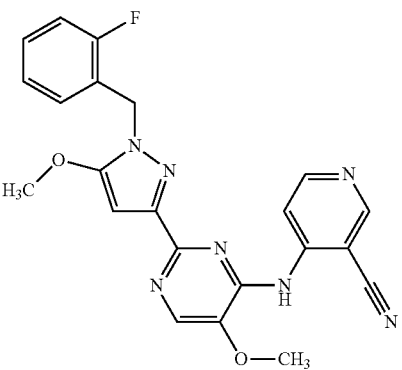 [SMILES: COc1cnc(-c2cc(OC)n(Cc3ccccc3F)n2)nc1Nc1ccncc1C#N] | 4-({2-[1-(2-fluorobenzyl)-5-methoxy-1H-pyrazol-3-yl]-5-methoxy-pyrimidin-4-yl}amino)pyridine-3-carbonitrile | $^1$H-NMR (300 MHz, DMSO-$d_6$): δ [ppm] = 3.91 (s, 3H), 3.99 (s, 3H), 5.19 (s, 2H), 6.18 (s, 1H), 7.05-7.25 (m, 3H), 7.27-7.38 (m, 1H), 8.23-8.38 (m, 2H), 8.58-8.68 (m, 1H), 8.77-8.88 (m, 1H), 8.96-9.06 (m, 1H). |
| 2-1-8 | 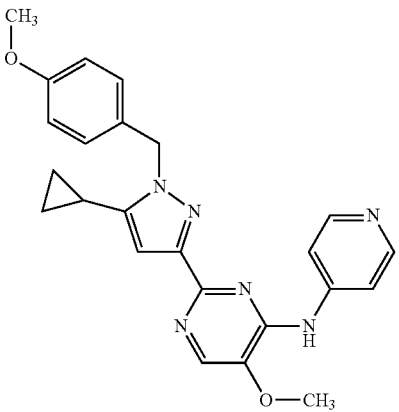 [SMILES: COc1ccc(Cn2nc(-c3ncc(OC)c(Nc4ccncc4)n3)cc2C2CC2)cc1] | 2-[5-cyclopropyl-1-(4-methoxybenzyl)-1H-pyrazol-3-yl]-5-methoxy-N-(pyridin-4-yl)pyrimidin-4-amine | $^1$H-NMR (300 MHz, DMSO-$d_6$): δ [ppm] = 0.62 (dd, 2H), 0.91 (dd, 2H), 1.80-1.96 (m, 1H), 3.69 (s, 3H), 3.95 (s, 3H), 5.37 (s, 2H), 6.38 (s, 1H), 6.81-6.94 (m, 2H), 7.20 (d, 2H), 8.01-8.10 (m, 2H), 8.16 (s, 1H), 8.28-8.42 (m, 3H), 9.27 (s, 1H). |
| 2-1-9 | 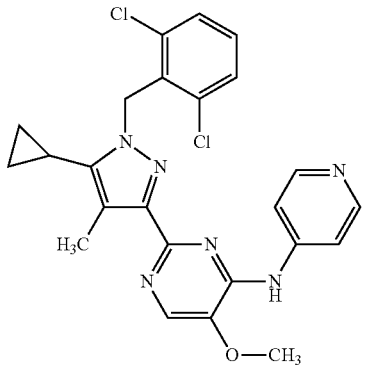 [SMILES: COc1cnc(-c2nn(Cc3c(Cl)cccc3Cl)c(C3CC3)c2C)nc1Nc1ccncc1] | 2-[5-cyclopropyl-1-(2,6-dichlorobenzyl)-4-methyl-1H-pyrazol-3-yl]-5-methoxy-N-(pyridin-4-yl)pyrimidin-4-amine | $^1$H-NMR (300 MHz, DMSO-$d_6$): δ [ppm] = 0.70-0.83 (m, 2H), 0.97-1.11 (m, 2H), 1.78-1.92 (m, 1H), 2.29 (s, 3H), 3.93 (s, 3H), 5.58 (s, 2H), 7.33-7.45 (m, 1H), 7.50-7.58 (m, 2H), 8.02 (d, 2H), 8.18 (s, 1H), 8.24-8.33 (m, 2H), 9.16 (s, 1H). |

| | | | |
|---|---|---|---|
| 2-1-10 | 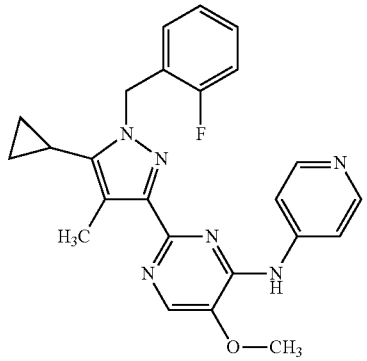 [SMILES: COc1cnc(-c2nn(Cc3ccccc3F)c(C3CC3)c2C)nc1Nc1ccncc1] | 2-[5-cyclo-propyl-1-(2-fluorobenzyl)-4-methyl-1H-pyrazol-3-yl]-5-methoxy-N-(pyridin-4-yl)pyrimidin-4-amine | $^1$H-NMR (300 MHz, DMSO-$d_6$): δ [ppm] = 0.58-0.68 (m, 2H), 0.90-1.02 (m, 2H), 1.64 (s, 1H), 2.27 (s, 3H), 3.96 (s, 3H), 5.46 (s, 2H), 7.06-7.40 (m, 4H), 7.99-8.09 (m, 2H), 8.21 (s, 1H), 8.27-8.37 (m, 2H), 9.23 (s, 1H). |
| 2-1-11 | 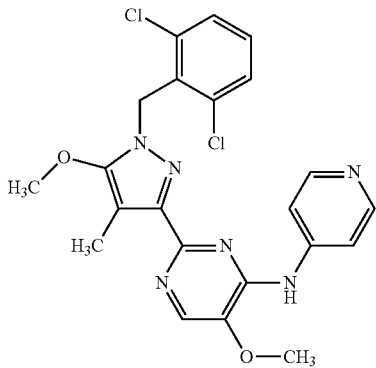 [SMILES: COc1cnc(-c2nn(Cc3c(Cl)cccc3Cl)c(OC)c2C)nc1Nc1ccncc1] | 2-[1-(2,6-di-chlorobenzyl)-5-methoxy-4-methyl-1H-pyrazol-3-yl]-5-methoxy-N-(pyridin-4-yl)pyrimidin-4-amine | $^1$H-NMR (300 MHz, DMSO-$d_6$): δ [ppm] = 2.25 (s, 3H), 3.94 (s, 3H), 3.96 (s, 3H), 5.38 (s, 2H), 7.35-7.44 (m, 1H), 7.52 (d, 2H), 8.03-8.11 (m, 2H), 8.19 (s, 1H), 8.26-8.34 (m, 2H), 9.22 (s, 1H). |
| 2-1-12 | 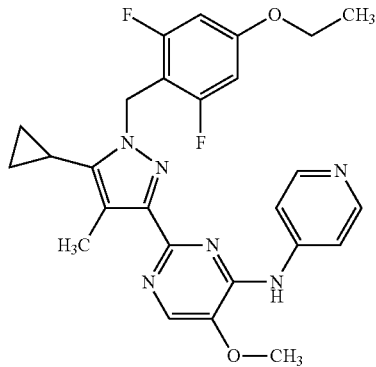 [SMILES: CCOc1cc(F)c(Cn2nc(-c3ncc(OC)c(Nc4ccncc4)n3)c(C)c2C2CC2)c(F)c1] | 2-[5-cyclo-propyl-1-(4-ethoxy-2,6-difluorobenzyl)-4-methyl-1H-pyrazol-3-yl]-5-methoxy-N-(pyridin-4-yl)pyrimidin-4-amine | $^1$H-NMR (300 MHz, DMSO-d6): δ [ppm] = 0.69-0.74 (m, 2H), 1.00-1.07 (m, 2H), 1.27 (t, 3H), 1.65-1.78 (m, 1H), 2.26 (s, 3H), 3.94 (s, 3H), 4.01 (q, 2H), 5.33 (s, 2H), 6.71-6.79 (m, 2H), 8.00-8.12 (m, 2H), 8.19 (s, 1H), 8.25-8.38 (m, 2H), 9.23 (s, 1H). |

Example 2-2-1

Preparation of 2-[5-cyclopropyl-1-(4-ethoxy-2,6-difluorobenzyl)-4-methyl-1H-pyrazol-3-yl]-4-(pyridin-4-ylamino)pyrimidin-5-ol

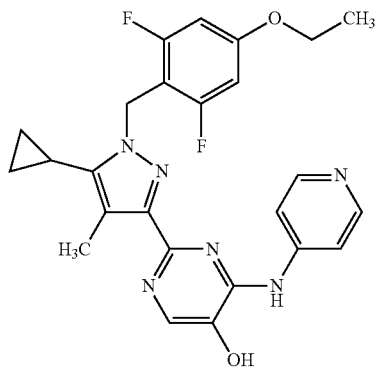 [SMILES: CCOc1cc(F)c(Cn2nc(-c3ncc(O)c(Nc4ccncc4)n3)c(C)c2C2CC2)c(F)c1]

310 mg of 2-[5-cyclopropyl-1-(4-ethoxy-2,6-difluorobenzyl)-4-methyl-1H-pyrazol-3-yl]-5-methoxy-N-(pyridin-4-yl)pyrimidin-4-amine 2-1-12 (0.629 mmol, 1 eq.) were dissolved in 27.2 mL of dry 1-methylpyrrolidin-2-one. 348 mg of potassium carbonate (2.52 mmol, 4.0 eq.), molecular sieve and 97 µL benzenethiol (0.944 mmol, 1.5 eq.) were added. The mixture was stirred for 1 hour at 150° C. bath temperature. 348 mg of potassium carbonate (2.52 mmol, 4.0 eq.) and 97 µL benzenethiol (0.944 mmol, 1.5 eq.) were added again and the mixture was stirred for a further hour at 150° C. bath temperature. Then the reaction mixture was partitioned between aqueous half saturated ammonium chloride solution and ethyl acetate. The separated aqueous layer was extracted twice with ethyl acetate. The combined organic layers were dried over a silicone filter and concentrated in vacuo. The purification of the residue by flash chromatography provided 191 mg (0.36 mmol, 56%) of analytically pure target compound.

¹H-NMR (400 MHz, DMSO-d₆): δ [ppm]=0.69-0.79 (m, 2H), 1.01-1.09 (m, 2H), 1.30 (t, 3H), 1.68-1.80 (m, 1H), 2.27 (s, 3H), 4.05 (q, 2H), 5.35 (s, 2H), 6.74-6.80 (m, 2H), 8.01 (s, 1H), 8.04-8.10 (m, 2H), 8.27-8.34 (m, 2H), 9.12 (br. s., 1H), 10.58 (br. s., 1H).

The following side product was isolated during the procedure described above:

Example 2-2-2

2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol

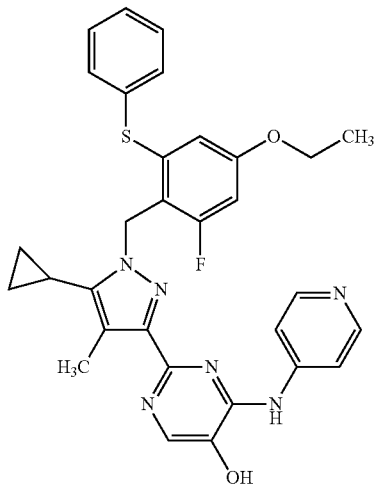 [SMILES: CCOc1cc(F)c(Cn2nc(-c3ncc(O)c(Nc4ccncc4)n3)c(C)c2C2CC2)c(Sc2ccccc2)c1]

¹H-NMR (300 MHz, DMSO-d₆): δ [ppm]=0.63-0.77 (m, 2H), 0.93-1.05 (m, 2H), 1.21 (t, 3H), 1.72-1.81 (m, 1H), 2.21 (s, 3H), 3.92 (q, 2H), 5.46 (s, 2H), 6.57 (d, 1H), 6.90 (dd, 1H), 7.14-7.32 (m, 5H), 7.97 (s, 1H), 8.01-8.09 (m, 2H), 8.18-8.31 (m, 2H), 9.10 (s, 1H), 10.89 (br. s., 1H).

Example 2-3-1

Preparation of 2-[5-cyclopropyl-1-(4-ethoxy-2,6-difluorobenzyl)-4-methyl-1H-pyrazol-3-yl]-5-[2-(dimethylamino)ethoxy]-N-(pyridin-4-yl)pyrimidin-4-amine

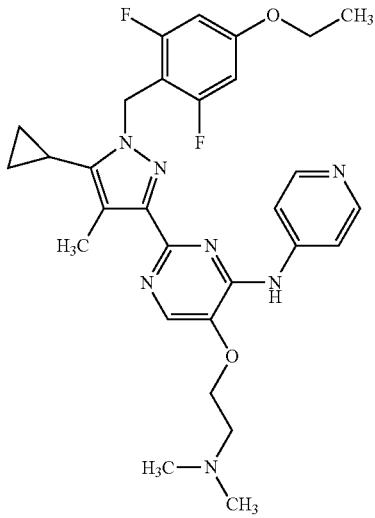 [SMILES: CCOc1cc(F)c(Cn2nc(-c3ncc(OCCN(C)C)c(Nc4ccncc4)n3)c(C)c2C2CC2)c(F)c1]

80 mg of 2-[5-cyclopropyl-1-(4-ethoxy-2,6-difluorobenzyl)-4-methyl-1H-pyrazol-3-yl]-4-(pyridin-4-ylamino)pyrimidin-5-ol 2-2-1 (0.048 mmol, 1.0 eq) were dissolved in 1.9 mL of dry DMF and 33.5 mg potassium carbonate (0.24 mmol, 5.0 eq) and 10.5 mg 2-chloro-N,N-dimethylethanamine (0.073 mmol, 1.5 eq) were added. The reaction mixture was stirred over night at 50° C. Then butan-2-one was added and the organic layer was washed with brine, dried over sodium sulfate and concentrated in vacuo. The purification of the residue by flash chromatography and HPLC provided 10 mg (0.02 mmol, 37%) of analytically pure target compound.

¹H-NMR (400 MHz, METHANOL-d4): δ[ppm]=0.73-0.80 (m, 2H), 1.05-1.13 (m, 2H), 1.35 (t, 3H), 1.66-1.76 (m, 1H), 2.32 (s, 3H), 2.82 (s, 6H), 3.41 (t, 2H), 4.01 (q, 2H), 4.47 (t, 2H), 5.47 (s, 2H), 6.54-6.62 (m, 2H), 8.18-8.26 (m, 3H), 8.38 (d, 2H).

The following compounds were prepared according to the same procedure as described above using the starting materials logically consistent with the structure of the end product shown in the table below:

| | | | |
|---|---|---|---|
| 2-3-2 | 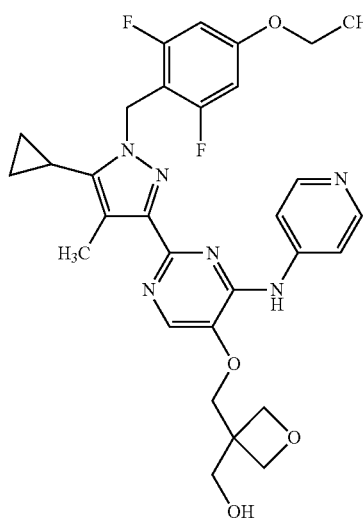 | {3-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)-methyl]oxetan-3-yl}methanol | ¹H-NMR (300 MHz, DMSO-d₆): δ [ppm] = 0.67-0.77 (m, 2H), 0.94-1.09 (m, 2H), 1.27 (t, 3H), 1.64-1.78 (m, 1H), 2.26 (s, 3H), 3.80 (s, 2H), 4.02 (q, 2H), 4.35 (s, 2H), 4.41 (s, 4H), 5.33 (s, 2H), 6.69-6.82 (m, 2H), 7.92-7.99 (m, 2H), 8.11 (s, 1H), 8.24-8.39 (m, 3H), 8.72 (s, 1H). |

| | | | |
|---|---|---|---|
| 2-3-3 | (structure) | 2-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)-ethanol | $^1$H-NMR (300 MHz, DMSO-$d_6$): δ [ppm] = 0.65-0.78 (m, 2H), 0.97-1.09 (m, 2H), 1.27 (t, 3H), 1.65-1.80 (m, 1H), 2.26 (s, 3H), 3.70-3.85 (m, 2H), 4.02 (q, 2H), 4.08-4.21 (m, 2H), 5.06 (t, 1H), 5.33 (s, 2H), 6.64-6.83 (m, 2H), 7.97-7.99 (m, 2H), 8.19 (s, 1H), 8.27-8.40 (m, 2H), 8.93 (s, 1H). |
| 2-3-4 | (structure) | 2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine | $^1$H-NMR (400 MHz, DMSO-$d_6$): δ [ppm] = 0.69-0.80 (m, 2H), 1.01-1.12 (m, 2H), 1.31 (t, 3H), 1.69-1.84 (m, 1H), 2.16 (s, 3H), 2.30 (s, 3H), 2.96 (t, 2H), 4.06 (q, 2H), 4.36 (t, 2H), 5.37 (s, 2H), 6.73-6.85 (m, 2H), 8.00-8.11 (m, 2H), 8.28 (s, 1H), 8.31-8.42 (m, 2H), 8.98 (s, 1H). |
| 2-3-5 | (structure) | 1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)-methanesulfonamide | $^1$H-NMR (300 MHz, DMSO-$d_6$): δ [ppm] = 0.67-0.77 (m, 2H), 0.99-1.07 (m, 2H), 1.27 (t, 3H), 1.65-1.78 (m, 1H), 2.26 (s, 3H), 4.02 (q, 2H), 5.22 (s, 2H), 5.34 (s, 2H), 6.71-6.79 (m, 2H), 7.39 (s, 2H), 7.95-8.04 (m, 2H), 8.31-8.38 (m, 2H), 8.41 (s, 1H), 9.00 (s, 1H). |

| | | | |
|---|---|---|---|
| 2-3-6 | 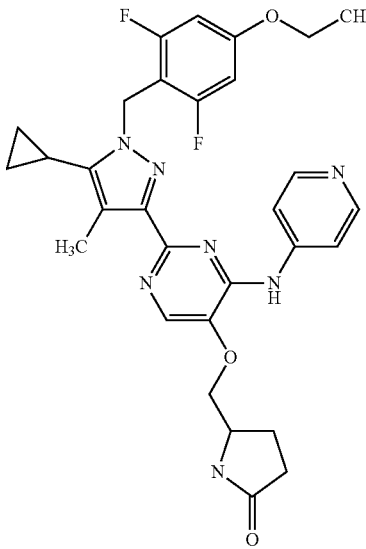 | 5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)-methyl]-pyrrolidin-2-one enantiomer 1 | $^1$H-NMR (300 MHz, DMSO-$d_6$): δ [ppm] = 0.68-0.73 (m, 2H), 0.96-1.09 (m, 2H), 1.27 (t, 3H), 1.63-1.79 (m, 2H), 2.10-2.29 (m, 6H), 3.79-3.91 (m, 1H), 3.93-4.05 (m, 3H), 4.20-4.31 (m, 1H), 5.33 (s, 2H), 6.72-6.81 (m, 2H), 7.91-8.05 (m, 2H), 8.18 (s, 1H), 8.29 (s, 1H), 8.33-8.40 (m, 2H), 8.75 (s, 1H). α = −68.8° (8.4 mg/mL DMSO) |
| 2-3-7 | 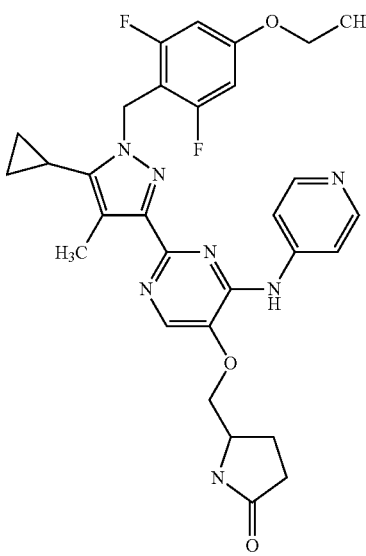 | 5-[({2-5-cyclopropyl-1-(4-ethoxy-2,6-difluorobenzyl)-4-methyl-1H-pyrazol-3-yl]-4-(pyridin-4-ylamino)pyrimidin-5-yl}oxy)-methyl]-pyrrolidin-2-one enantiomer 2 | $^1$H-NMR (300 MHz, DMSO-$d_6$): δ [ppm] = 0.68-0.73 (m, 2H), 0.96-1.09 (m, 2H), 1.27 (t, 3H), 1.63-1.79 (m, 2H), 2.10-2.29 (m, 6H), 3.79-3.91 (m, 1H), 3.93-4.05 (m, 3H), 4.20-4.31 (m, 1H), 5.33 (s, 2H), 6.72-6.81 (m, 2H), 7.91-8.05 (m, 2H), 8.18 (s, 1H), 8.29 (s, 1H), 8.33-8.40 (m, 2H), 8.75 (s, 1H). α = 81.9° (9.1 mg/mL DMSO) |
| 2-3-8 | 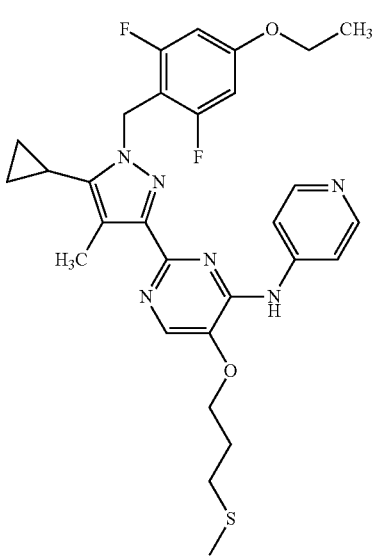 [SMILES: CCOc1cc(F)c(Cn2nc(-c3ncc(OCCCSC)c(Nc4ccncc4)n3)c(C)c2C2CC2)c(F)c1] | 2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)-pyrimidin-4-amine | $^1$H-NMR (300 MHz, DMSO-$d_6$): δ [ppm] = 0.65-0.84 (m, 2H), 0.99-1.13 (m, 2H), 1.31 (t, 3H), 1.65-1.83 (m, 1H), 1.98-2.17 (m, 5H), 2.29 (s, 3H), 2.73 (t, 2H), 4.05 (q, 2H), 4.25 (t, 2H), 5.36 (s, 2H), 6.71-6.95 (m, 2H), 7.99-8.17 (m, 2H), 8.23 (s, 1H), 8.29-8.41 (m, 2H), 8.96 (s, 1H). |

| | | | |
|---|---|---|---|
| 2-3-9 | 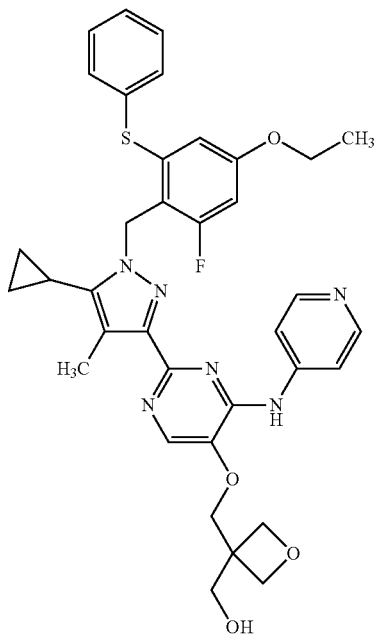 [SMILES: CCOc1cc(F)c(Cn2nc(-c3ncc(OCC4(CO)COC4)c(Nc4ccncc4)n3)c(C)c2C2CC2)c(Sc2ccccc2)c1] | [3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}-methyl)oxetan-3-yl]methanol | $^1$H-NMR (300 MHz, DMSO-$d_6$): δ [ppm] = 0.0.65-0.73 (m, 2H), 0.93-1.05 (m, 2H), 1.22 (t, 3H), 1.70-1.86 (m, 1H), 2.23 (s, 3H), 3.81 (d, 2H), 3.93 (q, 2H), 4.36 (s, 2H), 4.42 (s, 4H), 5.05 (t, 1H), 5.48 (s, 2H), 6.58 (d, 1H), 6.91 (dd, 1H), 7.16-7.32 (m, 5H), 7.88-8.03 (m, 2H), 8.22-8.37 (m, 3H), 8.73 (s, 1H). |
| 2-3-10 | 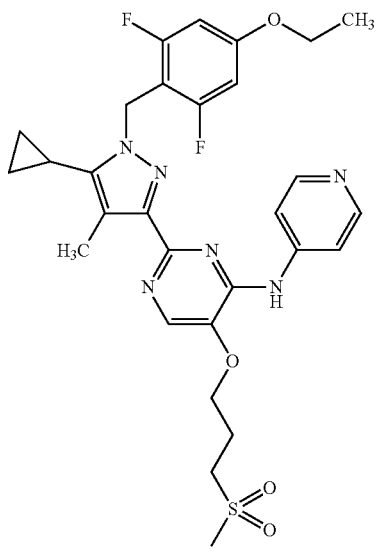 [SMILES: CCOc1cc(F)c(Cn2nc(-c3ncc(OCCCS(C)(=O)=O)c(Nc4ccncc4)n3)c(C)c2C2CC2)c(F)c1] | 2-[5-cyclopropyl-1-(4-ethoxy-2,6-difluorobenzyl)-4-methyl-1H-pyrazol-3-yl]-5-[3-(methylsulfonyl)-propoxy]-N-(pyridin-4-yl)-pyrimidin-4-amine | $^1$H-NMR (300 MHz, DMSO-$d_6$): δ [ppm] = 0.69-0.82 (m, 2H), 1.00-1.12 (m, 2H), 1.31 (t, 3H), 1.65-1.85 (m, 1H), 2.19-2.28 (m, 2H), 2.29 (s, 3H), 3.04 (s, 3H), 3.45 (t, 2H), 4.05 (q, 2H), 4.28 (t, 2H), 5.37 (s, 2H), 6.68-6.93 (m, 2H), 7.99-8.13 (m, 2H), 8.22 (s, 1H), 8.30-8.49 (m, 2H), 8.97 (s, 1H). |

Example 2-4-1

Preparation of 4-({2-[1-(2-fluorobenzyl)-5-methoxy-1H-pyrazol-3-yl]-5-methoxypyrimidin-4-yl}amino)pyridine-3-carboxamide

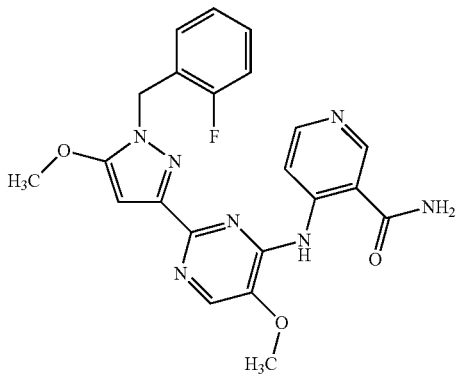 [SMILES: COc1cnc(-c2cc(OC)n(Cc3ccccc3F)n2)nc1Nc1ccncc1C(N)=O]

To 126 mg of 4-({2-[1-(2-fluorobenzyl)-5-methoxy-1H-pyrazol-3-yl]-5-methoxypyrimidin-4-yl}amino)pyridine-3-carbonitrile 2-1-7 (0.294 mmol, 1.0 eq.) were given at rt with caution 0.446 mL of sulfuric acid. The mixture was stirred for 24 hours at rt. Then the reaction mixture was dropped into ice water and set with aqueous 2 M sodium hydroxide solution to an alkaline pH. This aqueous layer was extracted three times with DCM/propan-2-ol 4:1. The combined organic layers were dried over magnesium sulfate and concentrated in vacuo. The crystallization from methanol provided 37.0 mg (0.08 mmol, 28%) of analytically pure target compound.

$^1$H-NMR (300 MHz, DMSO-$d_6$): δ [ppm]=3.95 (d, 6H), 5.22 (s, 2H), 6.26 (s, 1H), 7.10-7.26 (m, 3H), 7.29-7.40 (m, 1H), 7.73-7.86 (m, 1H), 8.22 (s, 1H), 8.34-8.43 (m, 1H), 8.46-8.54 (m, 1H), 8.84-8.91 (m, 1H), 9.08-9.16 (m, 1H), 12.04-12.16 (m, 1H).

The following compound was prepared according to the same procedure:

| | | | |
|---|---|---|---|
| 2-4-2 | 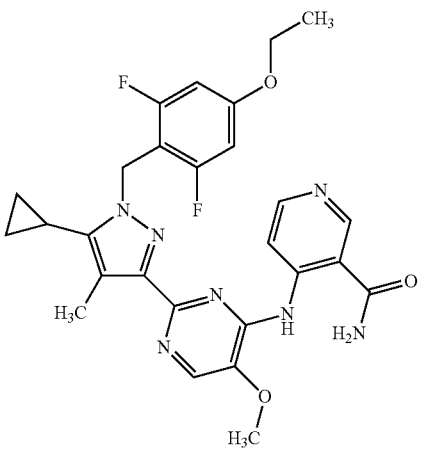 [SMILES: CCOc1cc(F)c(Cn2nc(-c3ncc(OC)c(Nc4ccncc4C(N)=O)n3)c(C)c2C2CC2)c(F)c1] | 4-({2-[5-cyclopropyl-1-(4-ethoxy-2,6-difluorobenzyl)-4-methyl-1H-pyrazol-3-yl]-5-methoxy-pyrimidin-4-yl}amino) nicotinamide | $^1$H-NMR (300 MHz, DMSO-$d_6$): δ [ppm] = 0.67-0.77 (m, 2H), 0.98-1.10 (m, 2H), 1.27 (t, 3H), 1.67-1.79 (m, 1H), 2.28 (s, 3H), 3.94 (s, 3H), 4.02 (q, 2H), 5.34 (s, 2H), 6.70-6.85 (m, 2H), 7.79 (s, 1H), 8.24 (s, 1H), 8.33-8.45 (m, 2H), 8.86 (s, 1H), 9.05-9.18 (m, 1H), 12.06 (s, 1H). |
| 2-4-3 | 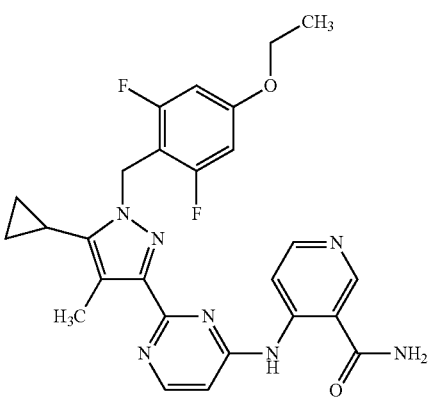 [SMILES: CCOc1cc(F)c(Cn2nc(-c3nccc(Nc4ccncc4C(N)=O)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino) nicotinamide | $^1$H-NMR (300 MHz, DMSO-$d_6$): δ [ppm] = 0.73 (m, 2H), 1.04 (m, 2H), 1.27 (t, 3H), 1.73 (m, 1H), 2.30 (s, 3H), 4.02 (q, 2H), 5.36 (s, 2H), 6.76 (m, 2H), 6.81 (d, 1H), 7.83 (s br, 1H), 8.35-8.41 (m, 2H), 8.44 (d, 1H), 8.85 (s, 1H), 8.93 (d, 1H), 11.71 (s, 1H). |

Example 2-5-1

Preparation of 2,4-dichloro-3-({5-cyclopropyl-3-[5-methoxy-4-(pyridin-4-ylamino) pyrimidin-2-yl]-4-methyl-1H-pyrazol-1-yl}methyl)benzoic acid

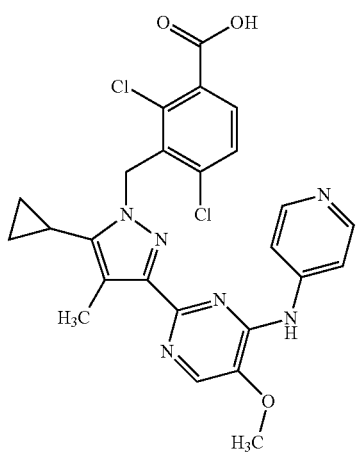 [SMILES: COc1cnc(-c2nn(Cc3c(Cl)ccc(C(=O)O)c3Cl)c(C3CC3)c2C)nc1Nc1ccncc1]

200 mg of 2-(5-cyclopropyl-4-methyl-1H-pyrazol-3-yl)-5-methoxy-N-(pyridin-4-yl)pyrimidin-4-amine 1-16-1 (0.62 mmol, 1.0 eq.), 184.86 mg of methyl 3-(bromomethyl)-2,4-dichlorobenzoate (0.62 mmol, 1.0 eq.) and 31.0 mg of 60% sodium hydride in paraffin oil were suspended in 6.3 mL of dry THF and stirred for 20 hours at rt. The reaction mixture was partitioned between water and DCM/propan-2-ol 4:1. The separated aqueous layer was extracted three times with DCM/propan-2-ol 4:1. The combined organic layers were dried over sodium sulfate and concentrated in vacuo. The purification by flash chromatography and preparative HPLC of the residue provided 37.5 mg (0.07 mmol, 11%) of analytically pure target compound.

$^1$H-NMR (400 MHz, DMSO-$d_6$): δ [ppm]=0.67-0.74 (m, 2H), 0.79-0.87 (m, 2H), 1.75-1.86 (m, 1H), 2.33 (s, 3H), 4.01 (s, 3H), 5.82 (s, 2H), 7.38 (d, 1H), 7.45 (d, 1H), 8.44-8.52 (m, 5H).

Example 2-6-1

Preparation of 2-[5-cyclopropyl-1-(4-methoxybenzyl)-4-methyl-1H-pyrazol-3-yl]-5-methoxy-N-(pyridin-4-yl)pyrimidin-4-amine

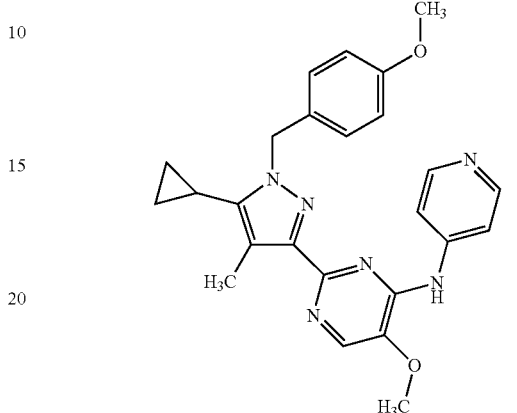

1.03 g of 2-[5-cyclopropyl-1-(4-methoxybenzyl)-4-methyl-1H-pyrazol-3-yl]-5-methoxypyrimidin-4-amine (2.82 mmol, 1.00 eq.), 603 mg of 4-bromopyridine hydrochloride (1:1) (3.10 mmol, 1.10 eq.), 245 mg of (9,9-dimethyl-9H-xanthene-4,5-diyl)bis(diphenylphosphine) (0.423 mmol, 0.15 eq.), 2.76 g of cesium carbonate (8.46 mmol, 3.00 eq.) and 63 mg of palladium diacetate (0.282 mmol, 0.1 eq.) were suspended in 10.8 mL of dry DMF and stirred under nitrogen atmosphere at 105° C. bath temperature for two hours. The reaction mixture was diluted with water and the crude product was extracted with DCM. The combined organic layers were dried over a silicon filter and concentrated in vacuo. The residue was purified by flash chromatography yielding 930 mg (1.95 mmol, 69%) of analytically pure target compound.

$^1$H-NMR (300 MHz, DMSO-$d_6$): δ [ppm]=0.55-0.65 (m, 2H), 0.92-0.98 (m, 2H), 1.47-1.63 (m, 1H), 2.25 (s, 3H), 3.68 (s, 3H), 3.96 (s, 3H), 5.32 (s, 2H), 6.79-6.93 (m, 2H), 7.17-7.22 (m, 2H), 8.01-8.12 (m, 2H), 8.22 (s, 1H), 8.29-8.38 (m, 2H), 9.27 (s, 1H)

The following compound was prepared according to the same procedure:

| | | | |
|---|---|---|---|
| 2-6-2 | 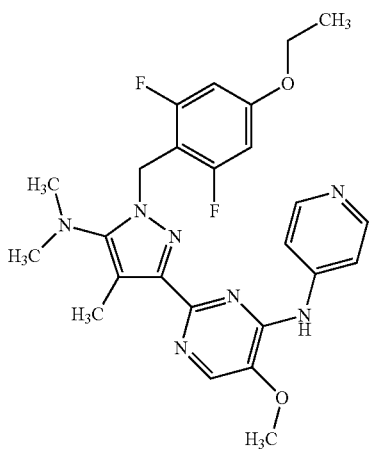 [SMILES: CCOc1cc(F)c(Cn2nc(-c3ncc(OC)c(Nc4ccncc4)n3)c(C)c2N(C)C)c(F)c1] | 2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine | $^1$H-NMR (600 MHz, DMSO-$d_6$): δ [ppm] = 1.37 (t, 3H), 2.40 (s, 3H), 2.89 (s, 6H), 4.04 (s, 3H), 4.08-4.13 (m, 2H), 5.26 (s, 2H), 6.79-6.87 (m, 2H), 8.19 (d, 2H), 8.30 (s, 1H), 8.41 (d, 2H), 9.36 (br. s., 1H). |

| | | | |
|---|---|---|---|
| 2-6-3 | 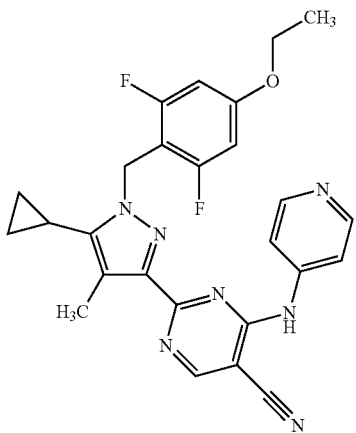 [SMILES: CCOc1cc(F)c(Cn2nc(-c3ncc(C#N)c(Nc4ccncc4)n3)c(C)c2C2CC2)c(F)c1] | 2-[5-cyclopropyl-1-(4-ethoxy-2,6-difluorobenzyl)-4-methyl-1H-pyrazol-3-yl]-4-(pyridin-4-ylamino)pyrimidine-5-carbonitrile | $^1$H-NMR (300 MHz, DMSO-d$_6$): δ [ppm] = 0.62-0.77 (m, 2H), 0.97-1.11 (m, 2H), 1.27 (t, 3H), 1.63-1.78 (m, 1H), 2.25 (s, 3H), 4.02 (q, 2H), 5.38 (s, 2H), 6.74 (d, 2H), 7.81-7.96 (m, 2H), 8.37 (d, 2H), 8.87 (s, 1H), 9.96 (br. s., 1H). |
| 2-6-4 | 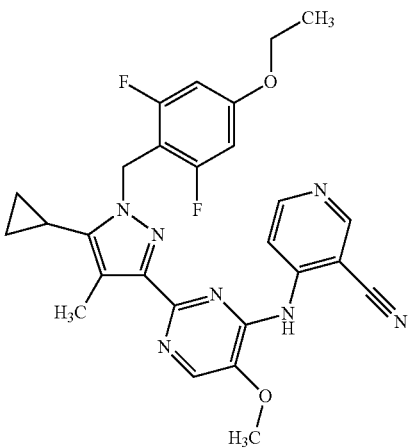 [SMILES: CCOc1cc(F)c(Cn2nc(-c3ncc(OC)c(Nc4ccncc4C#N)n3)c(C)c2C2CC2)c(F)c1] | 4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile | $^1$H-NMR (300 MHz, DMSO-d$_6$): δ [ppm] = 0.69-0.76 (m, 2 H), 1.01-1.10 (m, 2 H), 1.27-1.34 (m, 3 H), 1.67-1.76 (m, 1 H), 2.23 (s, 3 H) 3.99-4.09 (m, 5 H), 5.35 (s, 2 H), 6.73-6.81 (m, 2 H), 8.35 (s, 1 H) 8.50 (d, 1 H), 8.60 (s, 1 H), 8.76 (s, 1 H), 8.85 (s, 1 H). |
| 2-6-5 | 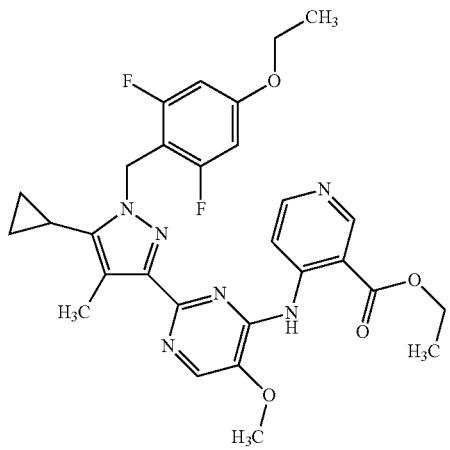 [SMILES: CCOC(=O)c1cnccc1Nc1nc(-c2nn(Cc3c(F)cc(OCC)cc3F)c(C3CC3)c2C)ncc1OC] | ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate | $^1$H-NMR (300 MHz, DMSO-d$_6$): δ [ppm] = 0.67-0.78 (m, 2H), 0.98-1.10 (m, 2H), 1.27 (t, 3H), 1.34 (t, 3H), 1.65-1.81 (m, 1H), 2.29 (s, 3H), 3.92-4.09 (m, 5H), 4.38 (q, 2H), 5.34 (s, 2H), 6.70-6.85 (m, 2H), 8.32 (s, 1H), 8.43-8.53 (m, 1H), 9.02 (s, 1H), 9.17-9.28 (m, 1H), 11.17 (s, 1H). |

| | | | |
|---|---|---|---|
| 2-6-6 | 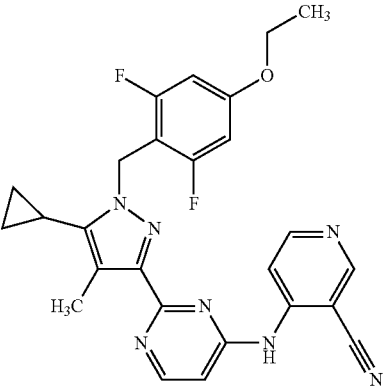 [SMILES: CCOc1cc(F)c(Cn2nc(-c3nccc(Nc4ccncc4C#N)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino)nicotinonitrile | $^{1}$H-NMR (300 MHz, DMSO-d$_{6}$): δ [ppm] = 0.70-0.78 (m, 2 H), 1.01-1.12 (m, 2 H), 1.31 (t, 3 H), 11.68-1.70 (s, 1 H), 2.27 (s, 3 H), 4.05 (q, 2 H), 5.38 (s, 2 H), 6.78 (d, 2 H), 7.11 (d, Hz, 1 H), 8.54 (d, 2 H), 8.57-8.62 (m, 1 H), 8.83 (s, 1 H), 9.99 (s, 1 H). |
| 2-6-7 | 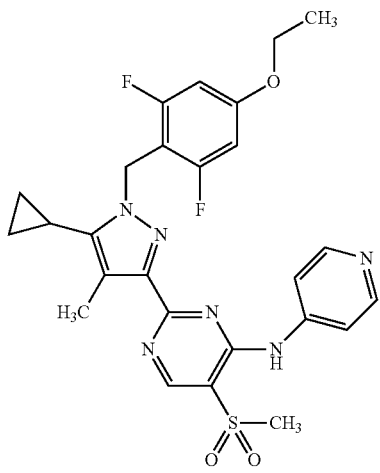 [SMILES: CCOc1cc(F)c(Cn2nc(-c3ncc(S(C)(=O)=O)c(Nc4ccncc4)n3)c(C)c2C2CC2)c(F)c1] | 2-[5-cyclopropyl-1-(4-ethoxy-2,6-difluorobenzyl)-4-methyl-1H-pyrazol-3-yl]-5-(methylsulfonyl)-N-(pyridin-4-yl)pyrimidin-4-amine | $^{1}$H-NMR (400 MHz, DMSO-d$_{6}$): δ [ppm] = 0.73 (m, 2 H), 1.05 (m, 2 H), 1.27 (t, 3 H), 1.72 (m, 1 H), 2.29 (s, 3 H), 3.41 (s, 3 H), 4.02 (q, 2 H), 5.40 (s, 2 H), 6.76 (m, 2 H), 7.85 (d, 2 H), 8.41 (d, 2 H), 8.83 (s, 1 H), 9.15 (s, 1 H). |
| 2-6-9 | 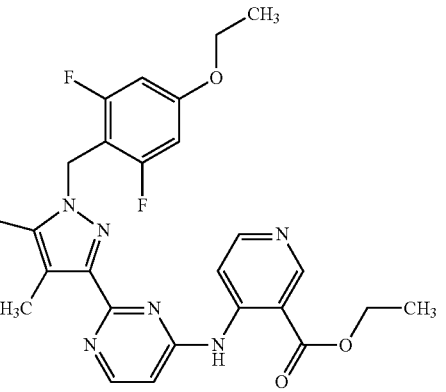 | ethyl 4-({2-[5-cyclopropyl-1-(4-ethoxy-2,6-difluorobenzyl)-4-methyl-1H-pyrazol-3-yl]pyrimidin-4-yl}amino)nicotinate | $^{1}$H-NMR (300 MHz, DMSO-d$_{6}$): δ [ppm] = 0.71-0.81 (m, 2 H), 1.02-1.13 (m, 2 H), 1.26-1.39 (m, 6 H), 1.81-1.73 (m, 1 H), 2.32 (s, 3 H), 4.05 (q, 2 H), 4.37 (q, 2 H), 5.40 (s, 2 H), 6.80 (d, 2 H), 6.99 (d, 1 H), 8.51 (dd, 2 H), 8.96-9.03 (m, 2 H), 10.64 (s, 1 H). |
| 2-6-10 | 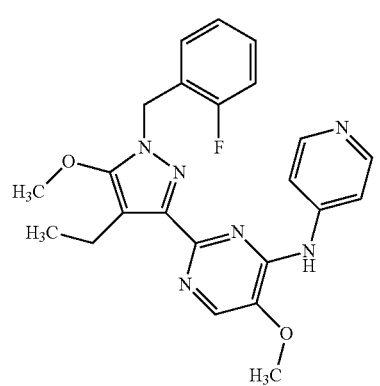 [SMILES: CCc1c(-c2ncc(OC)c(Nc3ccncc3)n2)nn(Cc2ccccc2F)c1OC] | 2-[4-ethyl-1-(2-fluorobenzyl)-5-methoxy-1H-pyrazol-3-yl]-5-methoxy-N-(pyridin-4-yl)pyrimidin-4-amine | |

| | |
|---|---|
| 2-6-11 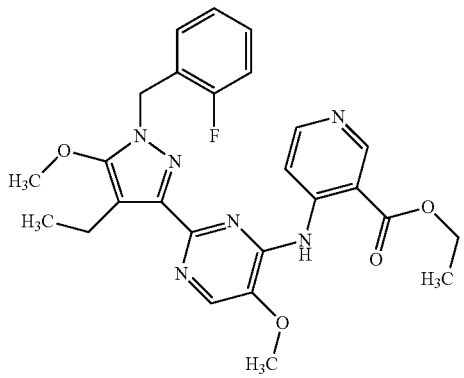 [SMILES: CCOC(=O)c1cnccc1Nc1nc(-c2nn(Cc3ccccc3F)c(OC)c2CC)ncc1OC] | ethyl 4-({2-[4-ethyl-1-(2-fluorobenzyl)-5-methoxy-1H-pyrazol-3-yl]-5-methoxypyrimidin-4-yl}amino)nicotinate |

Example 2-7-1

Preparation of 2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine

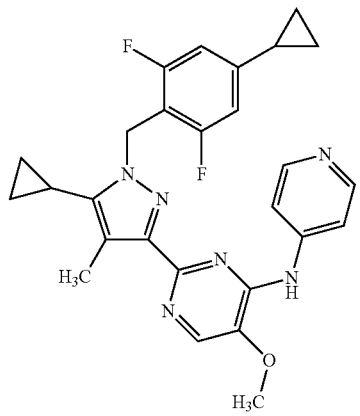 [SMILES: COc1cnc(-c2nn(Cc3c(F)cc(C4CC4)cc3F)c(C3CC3)c2C)nc1Nc1ccncc1]

16.5 mg of 2-[5-cyclopropyl-1-(4-cyclopropyl-2,6-difluorobenzyl)-4-methyl-1H-pyrazol-3-yl]-5-methoxypyrimidin-4-amine 1-17-3 (0.040 mmol, 1.0 eq.) and 16.1 mg 4-Fluoropyridine hydrochlorid (0.120 mmol, 3.0 eq.) were suspended in 0.19 mL dry DMF under a nitrogen atmosphere. 19.2 mg of sodium hydride (60% purity) were added and stirred at 90° C. for 2 h. Then the mixture was partitioned between half water and ethyl acetate. The aqueous layer was washed with ethyl acetate twice. The combined organic layers were washed with brine, dried over sodium sulfate and concentrated in vacuo. The crude product was purified by flash chromatography to obtain 5.7 mg (0.01 mmol, 20%) of the analytical pure target compound.

$^1$H-NMR (400 MHz, DMSO-$d_6$): δ [ppm]=0.69-0.74 (m, 4H), 0.92-1.08 (m, 4H), 1.66-1.78 (m, 1H), 1.89-2.01 (m, 1H), 2.26 (s, 3H), 3.94 (s, 3H), 5.36 (s, 2H), 6.73-6.96 (m, 2H), 8.06 (d, 2H), 8.18 (s, 1H), 8.30 (d, 2H), 9.21 (s, 1H).

Example 2-8-1

Preparation of 2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine

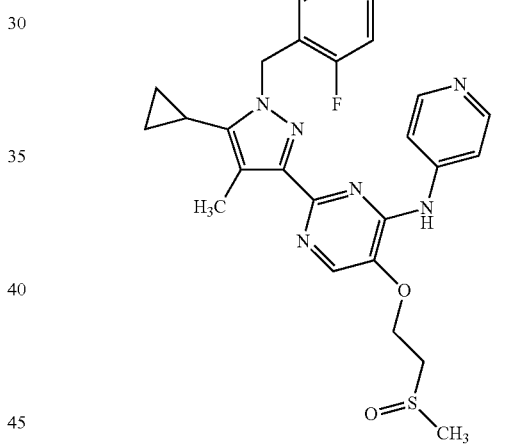

180 mg 2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine (0.326 mmol, 1.0 eq.) were dissolved in 1.7 mL chloroform and cooled to 0° C. 80.3 mg 3-chlorobenzenecarboperoxoic acid and the reaction mixture was stirred at 0° C. for 30 minutes. The reaction mixture was diluted with DCM and a solution of sodium thiosulfate (10% in water) was added and stirred for 5 minutes. The layers were separated and the aqueous layer was washed with DCM twice. The combined organic layers were washed with saturated sodium hydrogencarbonate solution, was dried over a silicon filter and concentrated in vacuo. The crude product was purified by flash chromatography to provide 136 mg of the analytically pure target compound as a racemate.

$^1$H-NMR (300 MHz, DMSO-$d_6$): δ [ppm]=0.69-0.81 (m, 2H), 1.01-1.13 (m, 2H), 1.31 (t, 3H), 1.70-1.83 (m, 1H), 2.30 (s, 3H), 2.70 (s, 3H), 3.15-3.25 (m, 1H), 3.31-3.41 (m, 1H), 4.06 (q, 2H), 4.51-4.70 (m, 2H), 5.37 (s, 2H), 6.71-6.85 (m, 2H), 7.93-8.08 (m, 2H), 8.28-8.44 (m, 3H), 9.25 (s, 1H).

Example 2-8-2 and 2-8-3

The racemate 2-8-1 was separated into both enantiomers by chiral HPLC:

$^1$H-NMR (300 MHz, DMSO-d$_6$): δ [ppm]=0.69-0.74 (m, 2H), 1.00-1.09 (m, 2H), 1.27 (t, 3H), 1.60-1.80 (m, 1H), 2.27 (s, 3H), 2.66 (s, 3H), 3.08-3.23 (m, 1H), 3.28-3.42 (m, 1H), 4.01 (q, 2H), 4.49-4.63 (m, 2H), 5.33 (s, 2H), 6.72-6.79 (m, 2H), 7.89-8.12 (m, 2H), 8.17-8.45 (m, 3H), 9.23 (s, 1H).

α=−21.3° (10.0 mg/mL DMSO)

$^1$H-NMR (300 MHz, DMSO-d$_6$): δ [ppm]=0.69-0.74 (m, 2H), 1.00-1.09 (m, 2H), 1.27 (t, 3H), 1.60-1.80 (m, 1H), 2.27 (s, 3H), 2.66 (s, 3H), 3.08-3.23 (m, 1H), 3.28-3.42 (m, 1H), 4.01 (q, 2H), 4.49-4.63 (m, 2H), 5.33 (s, 2H), 6.72-6.79 (m, 2H), 7.89-8.12 (m, 2H), 8.17-8.45 (m, 3H), 9.23 (s, 1H).

α=20.6° (10.3 mg/mL DMSO)

The following compound was prepared according to the same procedure as used in the preparation of Example 2-8-1

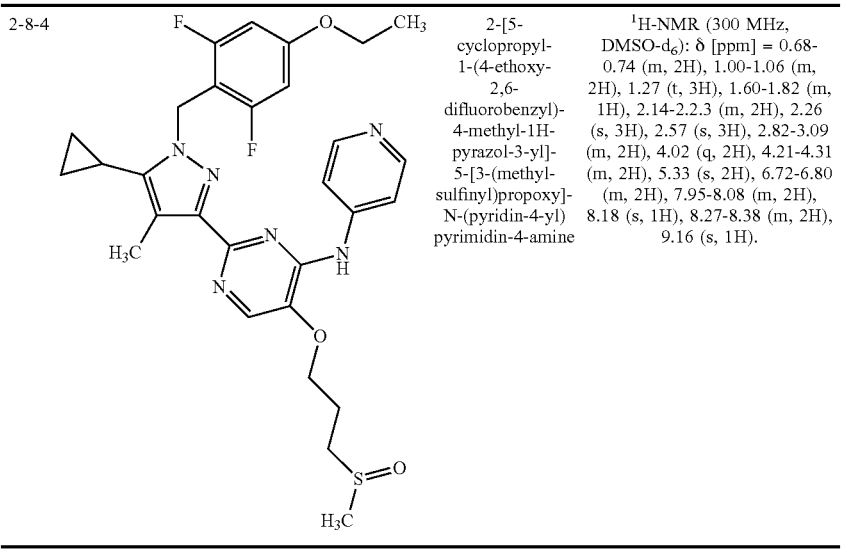

| 2-8-4 | 2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine | $^1$H-NMR (300 MHz, DMSO-d$_6$): δ [ppm] = 0.68-0.74 (m, 2H), 1.00-1.06 (m, 2H), 1.27 (t, 3H), 1.60-1.82 (m, 1H), 2.14-2.2.3 (m, 2H), 2.26 (s, 3H), 2.57 (s, 3H), 2.82-3.09 (m, 2H), 4.02 (q, 2H), 4.21-4.31 (m, 2H), 5.33 (s, 2H), 6.72-6.80 (m, 2H), 7.95-8.08 (m, 2H), 8.18 (s, 1H), 8.27-8.38 (m, 2H), 9.16 (s, 1H). |

Example 2-9-1

Preparation of 2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine

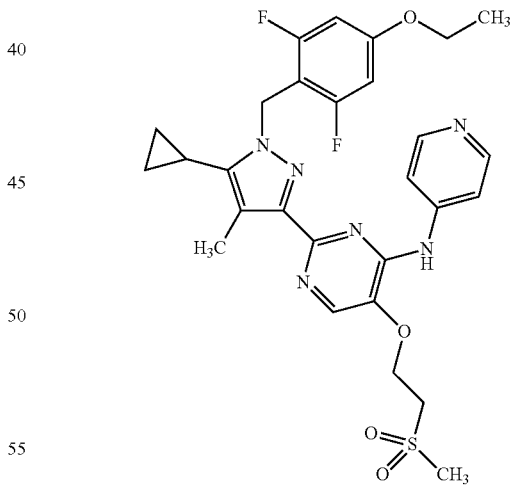

100 mg of 2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine (2-8-1, 0.176 mmol, 1.0 eq.) were suspended in 0.93 mL dry tetrahydrofuran under a nitrogen atmosphere. 90 μL hydrogen peroxide (30%, 0.879 mmol, 5.0 eq.) and 33 μL diethyl azodicarboxylate (0.211 mmol, 1.2 eq.) were added. The reaction mixture was stirred at 50° C. for 2 hours and concentrated in vacuo. The crude product was purified by flashcromatography to provide 31.9 mg (0.05 mmol, 31%) of the analytically pure target compound.

¹H-NMR (400 MHz, DMSO-d₆): δ [ppm]=0.68-0.81 (m, 2H), 1.03-1.11 (m, 2H), 1.31 (t, 3H), 1.70-1.83 (m, 1H), 2.30 (s, 3H), 3.12 (s, 3H), 3.75 (t, 2H), 4.06 (q, 2H), 4.60 (t, 2H), 5.37 (s, 2H), 6.69-6.88 (m, 2H), 7.91-8.07 (m, 2H), 8.33 (s, 1H), 8.34-8.40 (m, 2H), 8.89 (s, 1H).

Example 2-10-1

Preparation of 2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine

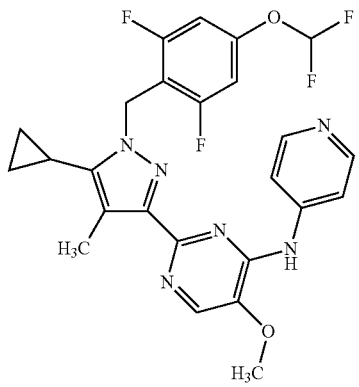 [SMILES: COc1cnc(-c2nn(Cc3c(F)cc(OC(F)F)cc3F)c(C3CC3)c2C)nc1Nc1ccncc1]

70 mg 2-(5-cyclopropyl-4-methyl-1H-pyrazol-3-yl)-5-methoxy-N-(pyridin-4-yl)pyrimidin-4-amine 1-16-1 (0-217 mmol, 1.0 eq) were dissolved in 0.52 mL THF and cooled to 0° C. 10.4 mg sodiumhydride (60%, 0.261 mmol, 1.2 eq) were added. The mixture stirred for 5 minutes, then the ice bath was removed and 65.2 mg 2-(bromomethyl)-5-(difluoromethoxy)-1,3-difluorobenzene (0.239 mmol, 1.1 eq) were added. The reaction stirred at rt for 4 days. Again 5 mg sodiumhydride (60%, 0.130 mmol, 0.6 eq) and 33 mg 2-(bromomethyl)-5-(difluoromethoxy)-1,3-difluorobenzene (0.120 mmol, 0.55 eq) were added. The reaction stirred at rt for 2 hours. Water was added and the aqueous layer was extracted by ethylacetate twice. The collected organic layers were washed with brine, dried with a silicon filter and concentrated in vacuo The crude product was purified by flashcromatography and HPLC to provide 10 mg (0.02 mmol, 8%) of the analytically pure target compound.

¹H-NMR (300 MHz, CHLOROFORM-d): δ [ppm]=0.64-0.77 (m, 2H), 0.97-1.10 (m, 2H), 1.66-1.81 (m, 1H), 2.26 (s, 3H), 3.94 (s, 3H), 5.40 (s, 2H), 7.03-7.15 (m, 2H), 7.32 (t, 1H), 7.98-8.10 (m, 2H), 8.19 (s, 1H), 8.26-8.36 (m, 2H), 9.20 (s, 1H).

The following compound was prepared according to the same procedure:

| | | | |
|---|---|---|---|
| 2-10-2 | 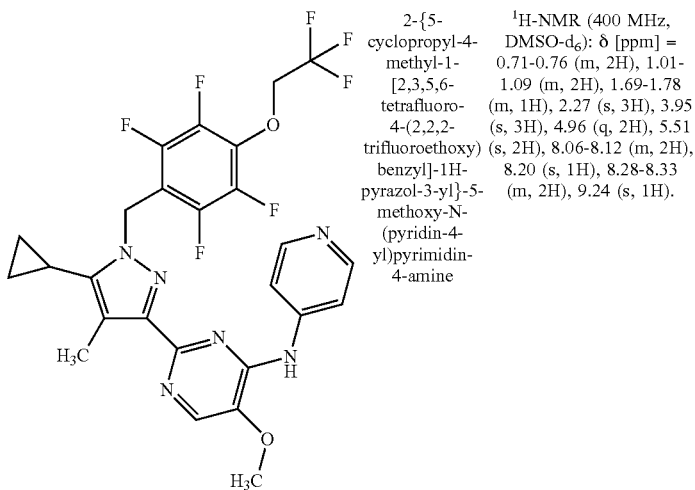 | 2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine | ¹H-NMR (400 MHz, DMSO-d₆): δ [ppm] = 0.71-0.76 (m, 2H), 1.01-1.09 (m, 2H), 1.69-1.78 (m, 1H), 2.27 (s, 3H), 3.95 (s, 3H), 4.96 (q, 2H), 5.51 (s, 2H), 8.06-8.12 (m, 2H), 8.20 (s, 1H), 8.28-8.33 (m, 2H), 9.24 (s, 1H). |

Example 2-11-1

Preparation of 4-({2-[5-cyclopropyl-1-(4-ethoxy-2,6-difluorobenzyl)-4-methyl-1H-pyrazol-3-yl]-5-methoxypyrimidin-4-yl}amino)nicotinic acid

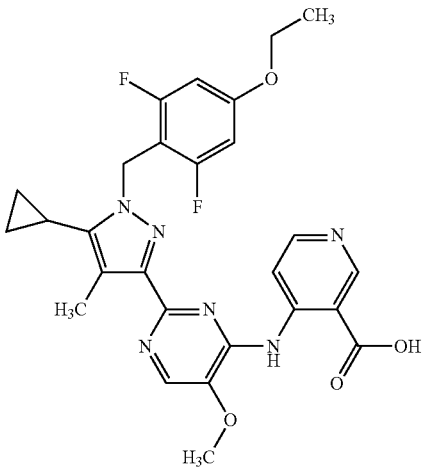 [SMILES: CCOc1cc(F)c(Cn2nc(-c3ncc(OC)c(Nc4ccncc4C(=O)O)n3)c(C)c2C2CC2)c(F)c1]

To a solution of 722 mg of ethyl 4-({2-[5-cyclopropyl-1-(4-ethoxy-2,6-difluorobenzyl)-4-methyl-1H-pyrazol-3-yl]-5-methoxypyrimidin-4-yl}amino)-pyridine-3-carboxylate 2-6-5 (1.28 mmol, 1.0 eq) in 13 mL THF and 1.6 mL methanol were added 256 mg sodium hydroxide (6.39 mmol, 5.0 eq). The mixture was stirred for 45 minutes at rt. Using 10% aqueous citric acid the pH of the mixture was adjusted to 3.5. The resulting suspension was filtered. The precipitate was washed with water and ethanol and subsequently dried to provide 660 mg of the desired product (1.11 mmol, 87%) as 90% pure target compound.

$^1$H-NMR (300 MHz, DMSO-$d_6$): δ [ppm]=0.76 (d, 2H), 1.03-1.14 (m, 2H), 1.30 (t, 3H), 1.69-1.84 (m, 1H), 2.32 (s, 3H), 4.05 (q, 5H), 5.38 (s, 2H), 6.80 (d, 2H), 8.34 (s, 1H), 8.45 (d, 1H), 9.00 (s, 1H), 9.27 (d, 1H), 12.59 (br. s., 1H).

The following compound was prepared according to the same procedure:

| | | | |
|---|---|---|---|
| 2-11-2 | 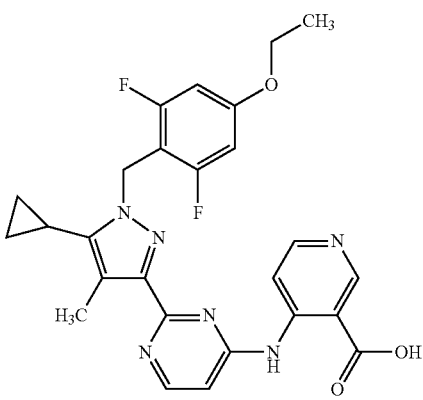 [SMILES: CCOc1cc(F)c(Cn2nc(-c3nccc(Nc4ccncc4C(=O)O)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino)nicotinic acid | $^1$H-NMR (300 MHz, DMSO-$d_6$): δ [ppm] = 0.77 (m, 2 H), 1.08 (m, 2 H), 1.31 (t, 3 H), 1.72-1.82 (m, 1 H), 2.34 (s, 3 H), 4.06 (q, 2 H), 5.40 (s, 2 H), 6.79 (d, 3 H), 8.31 (d, 1 H), 8.45 (d, 1 H), 8.92-9.00 (m, 2 H), 12.76 (br. s, 1H). |
| 2-11-3 | 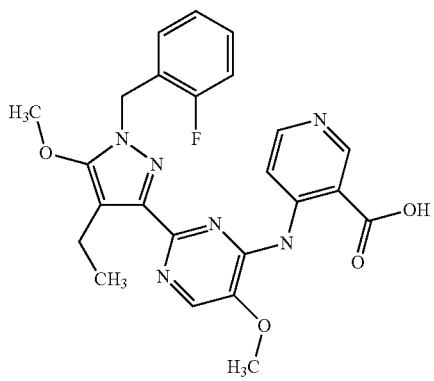 [SMILES: CCc1c(-c2ncc(OC)c(Nc3ccncc3C(=O)O)n2)nn(Cc2ccccc2F)c1OC] | 4-({2-[4-ethyl-1-(2-fluorobenzyl)-5-methoxy-1H-pyrazol-3-yl]-5-methoxy-pyrimidin-4-yl}amino)nicotinic acid | |

Example 2-12-1

Preparation of 4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide

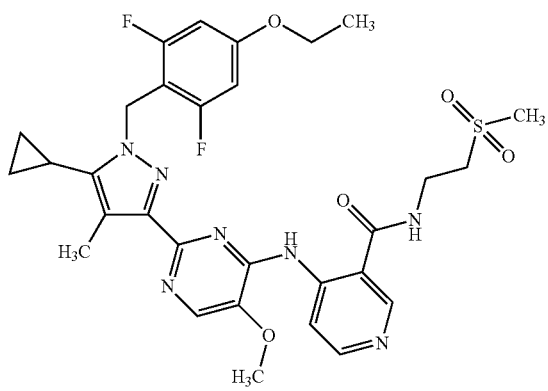 [SMILES: CCOc1cc(F)c(Cn2nc(-c3ncc(OC)c(Nc4ccncc4C(=O)NCCS(C)(=O)=O)n3)c(C)c2C2CC2)c(F)c1]

To a suspension of 147 mg 4-({2-[5-cyclopropyl-1-(4-ethoxy-2,6-difluorobenzyl)-4-methyl-1H-pyrazol-3-yl]-5-methoxypyrimidin-4-yl}amino)nicotinic acid 2-11-1 (0.27 mmol, 1.0 eq) and 67.5 mg 2-aminoethylmethyl sulfone (0.55 mmol, 2.0 eq) in 2.1 mL DMF were added 191 μL N,N-diisopropylethylamine (1.10 mmol, 4.0 eq) and 157 mg (benzotriazol-1-yloxy)tripyrrolidinophosphonium hexafluorophosphate (0.30 mmol, 1.1 eq). The resulting solution was stirred over night at rt and afterwards diluted with water. The precipitate was collected by filtration, washed with water and dried. The crude product was purified by preparative HPLC yielding 40 mg of analytically pure target compound (62 μmol, 22%).

$^1$H-NMR (300 MHz, DMSO-$d_6$): δ [ppm]=0.71-0.80 (m, 2H), 1.03-1.11 (m, 2H), 1.31 (t, 3H), 1.69-1.81 (m, 1H), 2.32 (s, 3H), 3.07 (s, 3H), 3.43 (t, 2H), 3.69-3.79 (m, 2H), 4.00 (s, 3H), 4.06 (q, 2H), 5.38 (s, 2H), 6.80 (d, 2H), 8.30 (s, 1H), 8.44 (d, 1H), 8.85 (s, 1H), 9.14 (d, 2H), 11.65 (s, 1H).

The following compounds were prepared according to the same procedure:

| | | | |
|---|---|---|---|
| 2-12-2 | 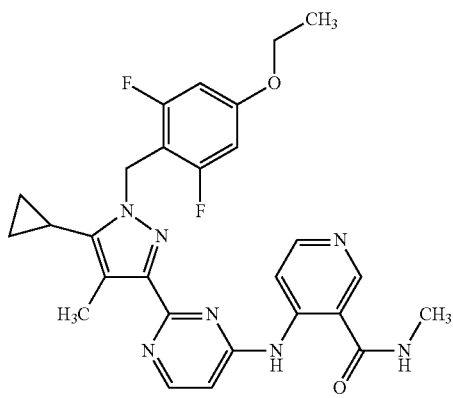 [SMILES: CCOc1cc(F)c(Cn2nc(-c3nccc(Nc4ccncc4C(=O)NC)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino)-N-methyl-nicotinamide | $^1$H-NMR (400 MHz, DMSO-$d_6$): δ [ppm] = 0.72-0.80 (m, 2 H), 1.07 (m, 2 H), 1.31 (t, 3 H), 1.70-1.84 (m, 1 H), 2.33 (s, 3 H), 2.83 (d, 3 H), 4.06 (q, 2 H), 5.40 (s, 2 H), 6.79 (d, 2 H), 6.88 (d, 1 H), 8.42 (s, 1 H) 8.48 (d, 1 H), 8.80 (s, 1H), 8.89 (br. s., 1 H) 8.94 (d, 1 H), 11.42 (s, 1 H). |
| 2-12-3 | 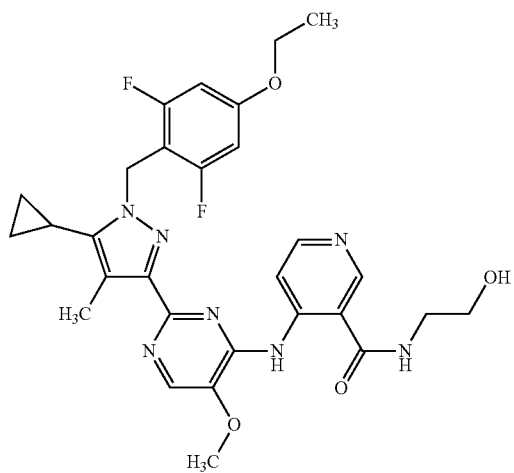 [SMILES: CCOc1cc(F)c(Cn2nc(-c3ncc(OC)c(Nc4ccncc4C(=O)NCCO)n3)c(C)c2C2CC2)c(F)c1] | 4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide | $^1$H-NMR (500 MHz, DMSO-$d_6$): δ [ppm] = 0.71-0.79 (m, 2 H), 1.71-1.83 (m, 1 H), 2.31 (s, 3 H), 3.37 (q, 2 H), 3.55 (q, 2 H), 3.99 (s, 3 H), 4.06 (q, 2 H), 4.78 (t, 1 H), 5.38 (s, 2 H), 6.80 (d, 2 H), 8.28 (s, 1 H), 8.42 (d, 1 H), 8.83-8.92 (m, 2 H), 9.13 (d, 1 H), 11.79 (s, 1 H). |

| | | | |
|---|---|---|---|
| 2-12-4 | 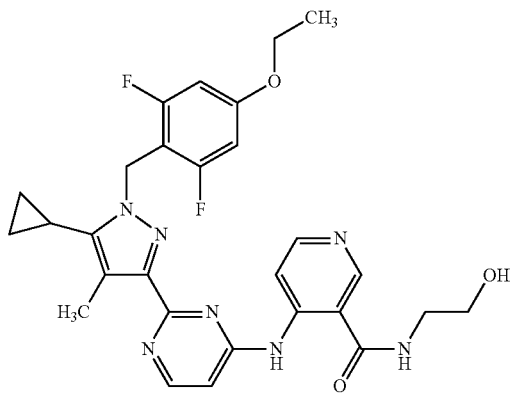 [SMILES: CCOc1cc(F)c(Cn2nc(-c3nccc(Nc4ccncc4C(=O)NCCO)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide | $^1$H-NMR (400 MHz, DMSO-d$_6$): δ [ppm] = 0.76 (m, 2 H), 1.08 (m, 2 H), 1.31 (t, 3 H), 1.72-1.81 (m, 1 H), 2.33 (s, 3 H), 3.37 (q, 2 H), 3.56 (q, 2 H), 4.06 (q, 2 H), 4.78 (t, 1 H), 5.40 (s, 2 H), 6.79 (m, 2 H), 6.88 (d, 1 H), 8.41 (d, 1 H), 8.48 (d, 1 H), 8.85 (s, 1 H), 8.89 (t, 1 H), 8.94 (d, 1 H), 11.34 (s, 1 H). |
| 2-12-5 | 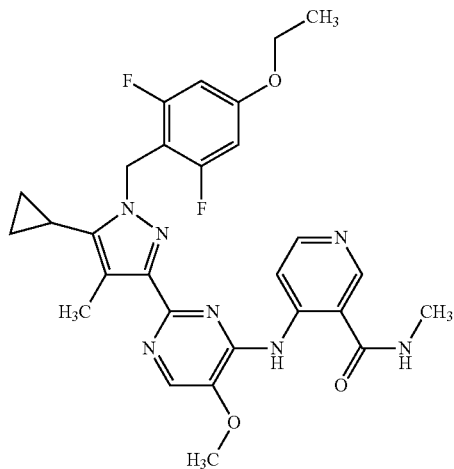 [SMILES: CCOc1cc(F)c(Cn2nc(-c3ncc(OC)c(Nc4ccncc4C(=O)NC)n3)c(C)c2C2CC2)c(F)c1] | 4-({2-[5-cyclopropyl-1-(4-ethoxy-2,6-difluorobenzyl)-4-methyl-1H-pyrazol-3-yl]-5-methoxy-pyrimidin-4-yl}amino)-N-methyl-nicotinamide | $^1$H-NMR (500 MHz, DMSO-d$_6$): δ [ppm] = 0.73-0.79 (m, 2 H), 1.05-1.10 (m, 2 H), 1.31 (t, 3 H), 1.73-1.80 (m, 1 H), 2.31 (s, 3 H), 2.83 (d, 3 H), 3.99 (s, 3 H), 4.06 (q, 2 H), 5.37 (s, 2 H), 6.80 (m, 2 H), 8.28 (s, 1 H), 8.42 (d, 1 H), 8.84 (s, 1 H), 8.87 (q, 1 H), 9.13 (d, 1 H), 11.86 (s, 1 H). |
| 2-12-6 | 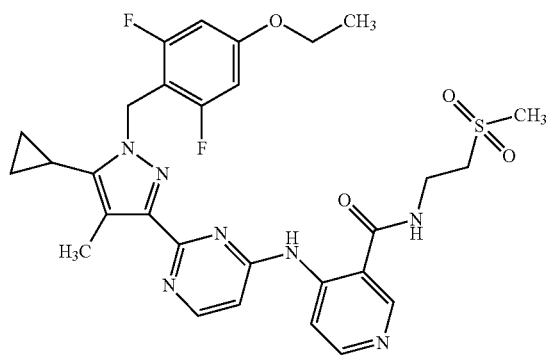 [SMILES: CCOc1cc(F)c(Cn2nc(-c3nccc(Nc4ccncc4C(=O)NCCS(C)(=O)=O)n3)c(C)c2C2CC2)c(F)c1] | 4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide | $^1$H-NMR (400 MHz, DMSO-d$_6$): δ [ppm] = 0.74-0.79 (m, 2 H), 1.05-1.11 (m, 2 H), 1.31 (t, 3 H), 1.74-1.78 (m, 1 H), 2.33 (s, 3 H), 3.06 (s, 3 H), 3.43 (t, 2 H), 3.72 (q, 2 H), 4.06 (q, 2 H), 5.40 (s, 2 H), 6.79 (d, 2 H), 6.90 (d, 1 H), 8.46 (dd, 2 H), 8.80 (s, 1 H), 8.94 (d, 1 H), 9.14 (br. s., 1 H), 11.08 (s, 1 H). |
| 2-12-7 | 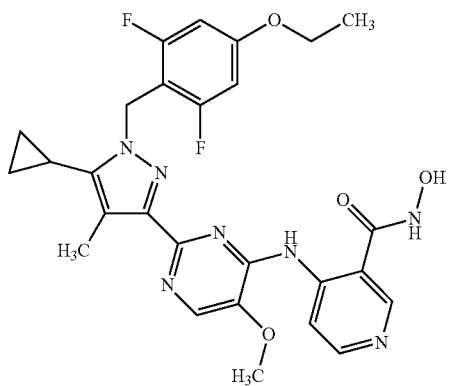 [SMILES: CCOc1cc(F)c(Cn2nc(-c3ncc(OC)c(Nc4ccncc4C(=O)NO)n3)c(C)c2C2CC2)c(F)c1] | 4-({2-[5-cyclopropyl-1-(4-ethoxy-2,6-difluorobenzyl)-4-methyl-1H-pyrazol-3-yl]-5-methoxy-pyrimidin-4-yl}amino)-N-hydroxy-nicotinamide | $^1$H-NMR (500 MHz, DMSO-d$_6$): δ [ppm] = 0.72-0.79 (m, 2 H), 1.03-1.11 (m, 2 H), 1.31 (t, 3 H), 1.76 (dd, 1 H), 2.31 (s, 3 H), 3.98 (s, 3 H), 4.02-4.10 (m, 2 H), 5.37 (s, 2 H), 6.79 (m, 2 H), 8.27-8.29 (m, 1 H), 8.40 (d, 1 H), 8.68-8.72 (m, 1 H), 9.10 (d, 1 H), 11.39-11.70 (m, 1 H). |

| | | |
|---|---|---|
| 2-12-8 | 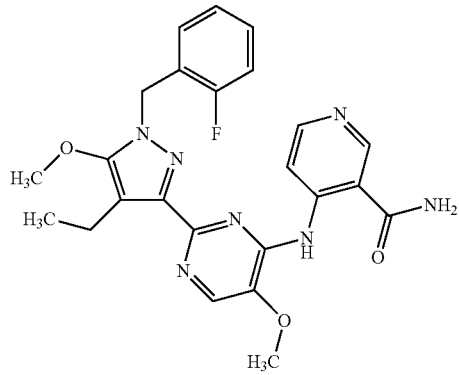 [SMILES: CCc1c(-c2ncc(OC)c(Nc3ccncc3C(N)=O)n2)nn(Cc2ccccc2F)c1OC] | 4-({2-[4-ethyl-1-(2-fluorobenzyl)-5-methoxy-1H-pyrazol-3-yl]-5-methoxy-pyrimidin-4-yl}amino) nicotinamide |

Biological Investigations

The following assays can be used to illustrate the commercial utility of the compounds according to the present invention.

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Biological Assay 1.0:
Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity-(Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 µl of Bub1 (the final concentration of Bub1 was adjusted depending on the activity of the enzyme lot in order to be within the linear dynamic range of the assay: typically ~200 µg/ml were used) in aqueous assay buffer [50 mM Tris/HCl pH 7.5, 10 mM magnesium chloride (MgCl2), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 µl 1.67-fold concentrated solution (in assay buffer) of adenosine-tri-phosphate (ATP, 10 µM final concentration) and peptide substrate (1 µM final concentration). The resulting mixture (5 µl final volume) was incubated at 22° C. during 60 min., and the reaction was stopped by the addition of 5 µl of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phosho-Serine antibody [Merck Millipore, cat. #35-001] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of (typically 32—) control wells for high—(=enzyme reaction without inhibitor=0%=Minimum inhibition) and low—(=all assay components without enzyme=100%=Maximum inhibition) Bub1 activity. $IC_{50}$ values were calculated by fitting the normalized inhibition data to a 4-parameter logistic equation (Minimum, Maximum, $IC_{50}$, Hill; Y=Max+(Min−Max)/(1+(X/$IC_{50}$)Hill)).

Biological Assay 2.0:
Proliferation Assay

Cultivated tumor cells (cells were ordered from ATCC, except HeLa-MaTu and HeLa-MaTu-ADR, which were ordered from EPO-GmbH, Berlin) were plated at a density of 1000 to 5000 cells/well, depending on the growth rate of the respective cell line, in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. Absorption was determined by photometry at a wavelength of 595 nm. The change of cell number, in percent, was calculated by normalization of the measured values to the absorption values of the zero-point plate (=0%) and the absorption of the untreated (0 µm) cells (=100%). The $IC_{50}$ values were determined by means of a 4 parameter fit.

TABLE 1

| Compounds had been evaluated in the following cell lines, which examplify the sub-indications listed | |
|---|---|
| Tumor indication | Cell line |
| Cervical cancer | HeLa |
|  | HeLa-MaTu-ADR |
| Non-small cell lung cancer (NSCLC) | NCl-H460 |
| Prostate cancer | DU145 |
| Colon cancer | Caco2 |
| Melanoma | B16F10 |

The following table gives the data for the examples of the present invention for the biological assays 1 and 2:

| Example Nr. | Biological Assay 1: Bub1 kinase assay median $IC_{50}$ [mol/l] | Biological Assay 2: Proliferation assay (HeLa cell line) median $IC_{50}$ [mol/l] |
|---|---|---|
| 2-1-1 | 6.14E−9 | 7.38E−6 |
| 2-1-2 | 1.15E−6 | >1.0E−5 |
| 2-1-3 | 3.81E−7 | >1.0E−5 |
| 2-1-4 | 6.38E−7 | >1.0E−5 |
| 2-1-5 | 5.16E−7 | >1.0E−5 |
| 2-1-6 | 5.17E−7 | >1.0E−5 |
| 2-1-7 | 1.42E−6 | >1.0E−5 |
| 2-1-8 | 7.38E−8 | >1.0E−5 |
| 2-1-9 | 5.76E−9 | >1.0E−5 |
| 2-1-10 | 3.65E−8 | 3.49E−6 |
| 2-1-11 | 7.86E−9 | 2.74E−6 |
| 2-1-12 | 6.03E−9 | 4.38E−6 |
| 2-2-1 | 6.20E−9 | nd |
| 2-2-2 | 5.39E−8 | 4.97E−6 |
| 2-3-1 | 7.45E−9 | 3.45E−6 |
| 2-3-2 | 5.23E−9 | 6.00E−6 |
| 2-3-3 | 7.86E−9 | 3.59E−6 |
| 2-3-4 | 1.08E−8 | 5.57E−6 |
| 2-3-5 | 5.55E−9 | 3.20E−6 |
| 2-3-6 | 8.14E−9 | 2.97E−6 |
| 2-3-7 | 1.21E−8 | 2.89E−6 |
| 2-3-8 | 1.37E−8 | 2.96E−6 |
| 2-3-9 | 2.49E−7 | 6.46E−6 |
| 2-3-10 | 9.49E−9 | 1.13E−6 |
| 2-4-1 | 4.15E−8 | >1.0E−5 |
| 2-4-2 | 1.05E−8 | 3.23E−6 |
| 2-4-3 | 9.32E−9 | 4.46E−6 |
| 2-5-1 | nd | nd |
| 2-6-1 | 1.51E−8 | nd |
| 2-6-2 | 1.26E−8 | nd |
| 2-6-3 | nd | 9.35E−6 |
| 2-6-4 | 4.86E−8 | nd |
| 2-6-5 | 2.74E−8 | nd |
| 2-6-6 | 8.77E−9 | >1.00E−5 |
| 2-6-7 | nd | nd |
| 2-6-8 | nd | nd |
| 2-6-9 | nd | nd |
| 2-6-10 | nd | nd |
| 2-6-11 | nd | nd |
| 2-7-1 | 8.62E−9 | nd |
| 2-8-1 | 4.19E−9 | 3.93E−6 |
| 2-8-2 | 3.96E−9 | nd |
| 2-8-3 | 6.17E−9 | nd |
| 2-8-4 | 7.90E−9 | 4.31E−6 |
| 2-9-1 | 7.87E−9 | 5.17E−6 |
| 2-10-1 | 6.79E−9 | nd |
| 2-10-2 | 6.13E−8 | 5.28E−6 |
| 2-11-1 | 2.68E−8 | nd |
| 2-11-2 | nd | nd |
| 2-11-3 | nd | nd |
| 2-12-1 | nd | nd |
| 2-12-2 | nd | nd |
| 2-12-3 | nd | nd |
| 2-12-4 | nd | nd |
| 2-12-5 | nd | nd |
| 2-12-6 | nd | nd |
| 2-12-7 | nd | nd |
| 2-12-8 | nd | nd |

Inhibition of proliferation of HeLa-MaTu-ADR, MCF7, NCI-H460, DU145, Caco-2 and B16F10 cells by compounds according to the present invention, determined as described under Biological Assays 2.0. All $IC_{50}$ (inhibitory concentration at 50% of maximal effect) values are indicated in [mol/L].

| Example Nr. | Biological Assay 2: Proliferation assay (HeLa-MaTu-ADR cell line) median IC50 [mol/l] | Biological Assay 2: Proliferation assay (H460 cell line) median IC50 [mol/l] | Biological Assay 2: Proliferation assay (DU145 cell line) median IC50 [mol/l] | Biological Assay 2: Proliferation assay (Caco2 cell line) median IC50 [mol/l] | Biological Assay 2: Proliferation assay (B16F10 cell line) median IC50 [mol/l] |
|---|---|---|---|---|---|
| 2-1-12 | 3.08E−6 | 2.62E−6 | 3.09E−6 | 2.13E−6 | 2.24E−6 |
| 2-3-1 | 1.26E−6 | 1.46E−6 | 3.2E−6 | 1.94E−6 | 4.22E−7 |
| 2-3-10 | 7.55E−7 | 1.55E−6 | 1.61E−6 | 1.41E−6 | 1.18E−6 |

Thus an additional aspect of the invention is the use of the compounds of claim 1-5 and especially of the compounds as specified in the table above for the treatment of cervix cancer, NSCLC, prostate cancer, colon cancer and melanoma.

The invention claimed is:
1. A compound of formula (I)

(I)

wherein
R¹ and R² are independently from each other hydrogen, halogen or phenyl-S—; R³ is independently from each other hydrogen, 1-6C-alkoxy, halogen, 2-6C-alkenyl, 3-6C-cycloalkyl, 1-6C-haloalkoxy or C(O)OH;
n is 1, 2, or 3;
R⁴ is
  (a) hydrogen,
  (b) hydroxy,
  (c) 1-6C-alkoxy optionally substituted with
    (c1) 1-2 OH,
    (c2) NR⁹R¹⁰,
    (c3) 1-4C-alkyl-S—,
    (c4) 1-4C-alkyl-S(O)—,
    (c5) 1-4C-alkyl-S(O)₂—, or
    (c6) —S(O)₂NR⁹R¹⁰,
  (d)

wherein the * is the point of attachment,
  (e)

wherein the * is the point of attachment,
  (f) cyano, or
  (g) 1-4C-alkyl-S(O)₂—;
R⁵ is
  (a) hydrogen,
  (b) 2-6C-hydroxyalkyl,
  (c)

wherein the * is the point of attachment, (d) —C(O)-(1-6C-alkyl),
  (e) —C(O)-(1-6C-alkylen)-O-(1-6C-alkyl), or
  (f) —C(O)-(1-6C-alkylen)-O-(1-6C-alkylen)-O-(1-6C-alkyl);
R⁶ is hydrogen, halogen, cyano, C(O)NR¹¹R¹², C(O)OR¹³ or C(O)NHOH;
R⁷ is hydrogen, 1-6C-alkyl, 2-6C-alkenyl, 1-6C-alkoxy, 3-6C-cycloalkyl, or NR⁹R¹⁰;
R⁸ is hydrogen or 1-6C-alkyl;
m is 1, 2, 3, or 4;
R⁹ and R¹⁰ are independently from each other hydrogen or 1-6C-alkyl;
R¹¹ and R¹² are independently from each other hydrogen, 1-6C-alkyl, 2-6C-hydroxyalkyl or (1-4C-alkyl)-SO₂-(1-4C-alkyl); and
R¹³ is hydrogen or 1-4C-alkyl,
or an N-oxide, a salt, a tautomer or a stereoisomer of said compound, or a salt of said N-oxide, tautomer or stereoisomer.

2. The compound according to claim 1,
wherein:
R¹ and R² are independently from each other hydrogen, halogen or phenyl-S—;
R³ is independently hydrogen, halogen, 1-4C-alkoxy, 3-6C-cycloalkyl, 1-4C-haloalkoxy or C(O)OH;
n is 1, 2, or 3;
R⁴ is
  (a) hydrogen,
  (b) hydroxy,
  (c) 1-4C-alkoxy optionally substituted with
    (c1) 1-2 OH,
    (c2) NR⁹R¹⁰,
    (c3) 1-4C-alkyl-S—,
    (c4) 1-4C-alkyl-S(O)—,
    (c5) 1-4C-alkyl-S(O)₂—, or
    (c6) S(O)₂NR⁹R¹⁰,
  (d)

wherein the * is the point of attachment,
  (e)

wherein the * is the point of attachment,
  (f) cyano, or
  (g) 1-4C-alkyl-S(O)₂—;
R⁵ is hydrogen;
R⁶ is hydrogen, cyano, C(O)NR¹¹R¹², C(O)OR¹³ or C(O)NHOH;
R⁷ is 2-4C-alkenyl, 1-4C-alkoxy, 3-6C-cycloalkyl or NR⁹R¹⁰;
R⁸ is hydrogen or 1-4C-alkyl;
m is 1, 2, 3, or 4;
R⁹ and R¹⁰ are independently from each other hydrogen or 1-4C-alkyl;

$R^{11}$ and $R^{12}$ are independently from each other hydrogen, 1-4C-alkyl, 2-6C-hydroxyalkyl or (1-4C-alkyl)-SO$_2$-(1-4C-alkyl); and $R^{13}$ is hydrogen or 1-4C-alkyl, or an N-oxide, a salt, a tautomer or a stereoisomer of said compound, or a salt of said N-oxide, tautomer or stereoisomer.

3. The compound according to claim 1, wherein:

$R^1$ and $R^2$ are independently from each other hydrogen, halogen or phenyl-S—;

$R^3$ is independently hydrogen, halogen, 1-4C-alkoxy, 3-6C-cycloalkyl, 1-4C-haloalkoxy or C(O)OH;

n is 1, 2, or 3;

$R^4$ is
(a) hydrogen,
(b) hydroxy,
(c) 1-4C-alkoxy optionally substituted with
  (c1) OH,
  (c2) NR$^9$R$^{10}$,
  (c3) 1-4C-alkyl-S—,
  (c4) 1-4C-alkyl-S(O)—,
  (c5) 1-4C-alkyl-S(O)$_2$—, or
  (c6) S(O)$_2$NR$^9$R$^{10}$,
(d)

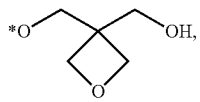

wherein the * is the point of attachment,
(e)

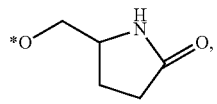

wherein the * is the point of attachment,
(f) cyano, or
(g) 1-4C-alkyl-S(O)$_2$—;

$R^5$ is hydrogen;

$R^6$ is hydrogen, cyano, C(O)NR$^{11}$R$^{12}$, C(O)OR$^{13}$ or C(O)NHOH;

$R^7$ is 2-4C-alkenyl, 1-4C-alkoxy, 3-6C-cycloalkyl or NR$^9$R$^{10}$;

$R^8$ is hydrogen or 1-4C-alkyl;

m is 1;

$R^9$ and $R^{10}$ are independently from each other hydrogen or 1-4C-alkyl;

$R^{11}$ and $R^{12}$ are independently from each other hydrogen, 1-4C-alkyl, 2-4C-hydroxyalkyl or (1-4C-alkyl)-SO$_2$-(1-4C-alkyl); and $R^{13}$ is hydrogen or 1-4C-alkyl, or an N-oxide, a salt, a tautomer or a stereoisomer of said compound, or a salt of said N-oxide, tautomer or stereoisomer.

4. The compound according to claim 1, wherein:

$R^1$ and $R^2$ are independently from each other hydrogen, fluorine, chlorine or phenyl-S—;

$R^3$ is hydrogen, fluorine, methoxy, ethoxy, cyclopropyl, difluoromethoxy, 2,2,2-trifluoroethoxy or C(O)OH;

n is 1, 2, or 3;

$R^4$ is
(a) hydrogen,
(b) hydroxy,
(c) methoxy optionally substituted with S(O)$_2$NH$_2$,
(d) ethoxy optionally substituted with hydroxy, —N(CH$_3$)$_2$, —SCH$_3$, —S(O)CH$_3$ or —S(O)$_2$CH$_3$,
(e) propoxy substituted with —SCH$_3$, —S(O)CH$_3$ or —S(O)$_2$CH$_3$,
(f)

wherein the * is the point of attachment,
(g)

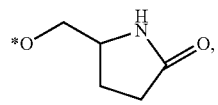

wherein the * is the point of attachment,
(h) cyano,
(i) —S(O)$_2$CH$_3$, or
(k) —S(O)$_2$CH(CH$_3$)$_2$;

$R^5$ is hydrogen;

$R^6$ is hydrogen, cyano, C(O)NH$_2$, C(O)NR$^{11}$R$^{12}$, C(O)OR$^{13}$ or C(O)NHOH;

$R^7$ is vinyl, methoxy, ethoxy, cyclopropyl or —N(CH$_3$)$_2$;

$R^8$ is hydrogen, methyl or ethyl;

m is 1;

$R^9$ and $R^{10}$ are independently from each other hydrogen or methyl;

$R^{11}$ is hydrogen;

$R^{12}$ is methyl, —CH$_2$—CH$_2$—OH, or —CH$_2$—CH$_2$—SO$_2$—CH$_3$; and $R^{13}$ is hydrogen or ethyl, or an N-oxide, a salt, a tautomer or a stereoisomer of said compound, or a salt of said N-oxide, tautomer or stereoisomer.

5. The compound according to claim 1, which is selected from the group consisting of:

2-[1-(4-ethoxy-2,6-difluorobenzyl)-5-methoxy-4-methyl-1H-pyrazol-3-yl]-5-methoxy-N-(pyridin-4-yl)pyrimidin-4-amine;

2-[5-(dimethylamino)-1-(2-fluorobenzyl)-1H-pyrazol-3-yl]-5-methoxy-N-(pyridin-4-yl)pyrimidin-4-amine;

2-[1-(2-fluorobenzyl)-5-methoxy-1H-pyrazol-3-yl]-5-methoxy-N-(pyridin-4-yl)pyrimidin-4-amine;

2-[5-ethoxy-1-(2-fluorobenzyl)-1H-pyrazol-3-yl]-5-methoxy-N-(pyridin-4-yl)pyrimidin-4-amine;

2-(1-benzyl-5-cyclopropyl-1H-pyrazol-3-yl)-5-methoxy-N-(pyridin-4-yl)pyrimidin-4-amine;

2-(1-benzyl-5-ethenyl-1H-pyrazol-3-yl)-5-methoxy-N-(pyridin-4-yl)pyrimidin-4-amine;

4-({2-[1-(2-fluorobenzyl)-5-methoxy-1H-pyrazol-3-yl]-5-methoxypyrimidin-4-yl}amino)pyridine-3-carbonitrile;

2-[5-cyclopropyl-1-(4-methoxybenzyl)-1H-pyrazol-3-yl]-5-methoxy-N-(pyridin-4-yl)pyrimidin-4-amine;

2-[5-cyclopropyl-1-(2,6-dichlorobenzyl)-4-methyl-1H-pyrazol-3-yl]-5-methoxy-N-(pyridin-4-yl)pyrimidin-4-amine;

2-[5-cyclopropyl-1-(2-fluorobenzyl)-4-methyl-1H-pyrazol-3-yl]-5-methoxy-N-(pyridin-4-yl)pyrimidin-4-amine;
2-[1-(2,6-dichlorobenzyl)-5-methoxy-4-methyl-1H-pyrazol-3-yl]-5-methoxy-N-(pyridin-4-yl)pyrimidin-4-amine;
2-[5-cyclopropyl-1-(4-ethoxy-2,6-difluorobenzyl)-4-methyl-1H-pyrazol-3-yl]-5-methoxy-N-(pyridin-4-yl)pyrimidin-4-amine;
2-[5-cyclopropyl-1-(4-ethoxy-2,6-difluorobenzyl)-4-methyl-1H-pyrazol-3-yl]-4-(pyridin-4-ylamino)pyrimidin-5-ol;
2-[5-cyclopropyl-1-(4-ethoxy-2,6-difluorobenzyl)-4-methyl-1H-pyrazol-3-yl]-5-[2-(dimethylamino)ethoxy]-N-(pyridin-4-yl)pyrimidin-4-amine;
{3-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]oxetan-3-yl}methanol;
2-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)ethanol;
4-({2-[1-(2-fluorobenzyl)-5-methoxy-1H-pyrazol-3-yl]-5-methoxypyrimidin-4-yl}amino)pyridine-3-carboxamide;
2,4-dichloro-3-({5-cyclopropyl-3-[5-methoxy-4-(pyridin-4-ylamino)pyrimidin-2-yl]-4-methyl-1H-pyrazol-1-yl}methyl)benzoic acid;
2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-ol;
2-[5-cyclopropyl-1-(4-ethoxy-2,6-difluorobenzyl)-4-methyl-1H-pyrazol-3-yl]-5-[2-(methylsulfanyl)ethoxy]-N-(pyridin-4-yl)pyrimidin-4-amine;
1-({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methanesulfonamide;
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 1;
5-[({2-[5-cyclopropyl-1-(4-ethoxy-2,6-difluorobenzyl)-4-methyl-1H-pyrazol-3-yl]-4-(pyridin-4-ylamino)pyrimidin-5-yl}oxy)methyl]pyrrolidin-2-one enantiomer 2;
2-[5-cyclopropyl-1-(4-ethoxy-2,6-difluorobenzyl)-4-methyl-1H-pyrazol-3-yl]-5-[3-(methylsulfanyl)propoxy]-N-(pyridin-4-yl)pyrimidin-4-amine;
[3-({[2-{5-cyclopropyl-1-[4-ethoxy-2-fluoro-6-(phenylsulfanyl)benzyl]-4-methyl-1H-pyrazol-3-yl}-4-(pyridin-4-ylamino)pyrimidin-5-yl]oxy}methyl)oxetan-3-yl]-methanol;
2-[5-cyclopropyl-1-(4-ethoxy-2,6-difluorobenzyl)-4-methyl-1H-pyrazol-3-yl]-5-[3-(methylsulfonyl)propoxy]-N-(pyridin-4-yl)pyrimidin-4-amine;
4-({2-[5-cyclopropyl-1-(4-ethoxy-2,6-difluorobenzyl)-4-methyl-1H-pyrazol-3-yl]-5-methoxypyrimidin-4-yl}amino)nicotinamide;
4-({2-[5-cyclopropyl-1-(4-ethoxy-2,6-difluorobenzyl)-4-methyl-1H-pyrazol-3-yl]pyrimidin-4-yl}amino)nicotinamide;
2-[5-cyclopropyl-1-(4-methoxybenzyl)-4-methyl-1H-pyrazol-3-yl]-5-methoxy-N-(pyridin-4-yl)pyrimidin-4-amine;
2-[5-(dimethylamino)-1-(4-ethoxy-2,6-difluorobenzyl)-4-methyl-1H-pyrazol-3-yl]-5-methoxy-N-(pyridin-4-yl)pyrimidin-4-amine;
2-[5-cyclopropyl-1-(4-ethoxy-2,6-difluorobenzyl)-4-methyl-1H-pyrazol-3-yl]-4-(pyridin-4-ylamino)pyrimidine-5-carbonitrile;
4-({2-[5-cyclopropyl-1-(4-ethoxy-2,6-difluorobenzyl)-4-methyl-1H-pyrazol-3-yl]-5-methoxypyrimidin-4-yl}amino)nicotinonitrile;
ethyl 4-({2-[5-cyclopropyl-1-(4-ethoxy-2,6-difluorobenzyl)-4-methyl-1H-pyrazol-3-yl]-5-methoxypyrimidin-4-yl}amino)nicotinate;
4-({2-[5-cyclopropyl-1-(4-ethoxy-2,6-difluorobenzyl)-4-methyl-1H-pyrazol-3-yl]pyrimidin-4-yl}amino)nicotinonitrile;
2-[5-cyclopropyl-1-(4-ethoxy-2,6-difluorobenzyl)-4-methyl-1H-pyrazol-3-yl]-5-(methylsulfonyl)-N-(pyridin-4-yl)pyrimidin-4-amine;
2-[5-cyclopropyl-1-(4-ethoxy-2,6-difluorobenzyl)-4-methyl-1H-pyrazol-3-yl]-5-(isopropylsulfonyl)-N-(pyridin-4-yl)pyrimidin-4-amine;
ethyl 4-({2-[5-cyclopropyl-1-(4-ethoxy-2,6-difluorobenzyl)-4-methyl-1H-pyrazol-3-yl]pyrimidin-4-yl}amino)nicotinate;
2-[4-ethyl-1-(2-fluorobenzyl)-5-methoxy-1H-pyrazol-3-yl]-5-methoxy-N-(pyridin-4-yl)pyrimidin-4-amine;
ethyl 4-({2-[4-ethyl-1-(2-fluorobenzyl)-5-methoxy-1H-pyrazol-3-yl]-5-methoxypyrimidin-4-yl}amino)nicotinate;
2-[5-cyclopropyl-1-(4-cyclopropyl-2,6-difluorobenzyl)-4-methyl-1H-pyrazol-3-yl]-5-methoxy-N-(pyridin-4-yl)pyrimidin-4-amine;
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine;
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 1;
2-[5-cyclopropyl-1-(4-ethoxy-2,6-difluorobenzyl)-4-methyl-1H-pyrazol-3-yl]-5-[2-(methylsulfinyl)ethoxy]-N-(pyridin-4-yl)pyrimidin-4-amine enantiomer 2;
2-[5-cyclopropyl-1-(4-ethoxy-2,6-difluorobenzyl)-4-methyl-1H-pyrazol-3-yl]-5-[3-(methylsulfinyl)propoxy]-N-(pyridin-4-yl)pyrimidin-4-amine;
2-[5-cyclopropyl-1-(4-ethoxy-2,6-difluorobenzyl)-4-methyl-1H-pyrazol-3-yl]-5-[2-(methylsulfonyl)ethoxy]-N-(pyridin-4-yl)pyrimidin-4-amine;
2-{5-cyclopropyl-1-[4-(difluoromethoxy)-2,6-difluorobenzyl]-4-methyl-1H-pyrazol-3-yl}-5-methoxy-N-(pyridin-4-yl)pyrimidin-4-amine;
2-{5-cyclopropyl-4-methyl-1-[2,3,5,6-tetrafluoro-4-(2,2,2-trifluoroethoxy)benzyl]-1H-pyrazol-3-yl}-5-methoxy-N-(pyridin-4-yl)pyrimidin-4-amine;
4-({2-[5-cyclopropyl-1-(4-ethoxy-2,6-difluorobenzyl)-4-methyl-1H-pyrazol-3-yl]-5-methoxypyrimidin-4-yl}amino)nicotinic acid;
4-({2-[5-cyclopropyl-1-(4-ethoxy-2,6-difluorobenzyl)-4-methyl-1H-pyrazol-3-yl]pyrimidin-4-yl}amino)nicotinic acid;
4-({2-[4-ethyl-1-(2-fluorobenzyl)-5-methoxy-1H-pyrazol-3-yl]-5-methoxypyrimidin-4-yl}amino)nicotinic acid;
4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide;
4-({2-[5-cyclopropyl-1-(4-ethoxy-2,6-difluorobenzyl)-4-methyl-1H-pyrazol-3-yl]pyrimidin-4-yl}amino)-N-methylnicotinamide;

4-({2-[5-cyclopropyl-1-(4-ethoxy-2,6-difluorobenzyl)-4-methyl-1H-pyrazol-3-yl]-5-methoxypyrimidin-4-yl}amino)-N-(2-hydroxyethyl)nicotinamide;

4-({2-[5-cyclopropyl-1-(4-ethoxy-2,6-difluorobenzyl)-4-methyl-1H-pyrazol-3-yl]pyrimidin-4-yl}amino)-N-(2-hydroxyethyl)nicotinamide;

4-({2-[5-cyclopropyl-1-(4-ethoxy-2,6-difluorobenzyl)-4-methyl-1H-pyrazol-3-yl]-5-methoxypyrimidin-4-yl}amino)-N-[2-(methylsulfonyl)ethyl]nicotinamide;

4-({2-[5-cyclopropyl-1-(4-ethoxy-2,6-difluorobenzyl)-4-methyl-1H-pyrazol-3-yl]pyrimidin-4-yl}amino)-N-[2-(methylsulfonyl)ethyl]nicotinamide;

4-({2-[5-cyclopropyl-1-(4-ethoxy-2,6-difluorobenzyl)-4-methyl-1H-pyrazol-3-yl]-5-methoxypyrimidin-4-yl}amino)-N-hydroxynicotinamide; and 4-({2-[4-ethyl-1-(2-fluorobenzyl)-5-methoxy-1H-pyrazol-3-yl]-5-methoxypyrimidin-4-yl}amino)nicotinamide, or an N-oxide, a salt, a tautomer or a stereoisomer of said compound, or a salt of said N-oxide, tautomer or stereoisomer.

6. A method for the treatment of cervical cancer, NSCLC, prostate cancer, colon cancer or melanoma, comprising administering to a patient in need thereof a therapeutically effective amount of the compound according to claim 1.

7. A pharmaceutical composition comprising at least one compound according to claim 1, together with at least one pharmaceutically acceptable auxiliary.

8. A combination comprising one or more first active ingredients selected from compounds according to claim 1, and one or more second active ingredients selected from chemotherapeutic anti-cancer agents and target-specific anti-cancer agents.

9. The compound according to claim 1, wherein:
$R^6$ is hydrogen, cyano, C(O)NH$_2$, C(O)NR$^{11}$R$^{12}$, C(O)OR$^{13}$ or C(O)NHOH, or a salt thereof.

10. The compound according to claim 1, wherein:
$R^7$ is vinyl, methoxy, ethoxy, cyclopropyl or —N(CH$_3$)$_2$; and
$R^8$ is hydrogen, methyl or ethyl,
or a salt thereof.

* * * * *